(12) United States Patent
Wood et al.

(10) Patent No.: US 8,183,008 B2
(45) Date of Patent: May 22, 2012

(54) EVALUATING MMP EXPRESSION IN PATIENT STRATIFICATION AND OTHER THERAPEUTIC, DIAGNOSTIC AND PROGNOSTIC METHODS FOR CANCER

(75) Inventors: Clive R. Wood, Boston, MA (US); Daniel T. Dransfield, Hanson, MA (US); Laetitia Devy, Somerville, MA (US)

(73) Assignee: Dyax Corp., Burlington, MA (US)

( * ) Notice: Subject to any disclaimer, the term of this patent is extended or adjusted under 35 U.S.C. 154(b) by 480 days.

(21) Appl. No.: 12/337,218

(22) Filed: Dec. 17, 2008

(65) Prior Publication Data

US 2009/0203060 A1 Aug. 13, 2009

Related U.S. Application Data

(60) Provisional application No. 61/025,017, filed on Jan. 31, 2008, provisional application No. 61/008,153, filed on Dec. 17, 2007.

(51) Int. Cl.
*C12Q 1/37* (2006.01)
(52) U.S. Cl. ........................................................ 435/24
(58) Field of Classification Search ........................ None
See application file for complete search history.

(56) References Cited

U.S. PATENT DOCUMENTS

| | | | |
|---|---|---|---|
| 6,984,619 | B1 | 1/2006 | Grdina et al. |
| 7,745,587 | B2 | 6/2010 | Devy et al. |
| 2004/0096899 | A1 | 5/2004 | Aoki et al. |
| 2005/0058725 | A1 | 3/2005 | McKearn et al. |
| 2005/0129615 | A1 | 6/2005 | Rozga et al. |
| 2006/0036076 | A1 | 2/2006 | Dransfield et al. |
| 2006/0275294 | A1 | 12/2006 | Omoigui |
| 2007/0117848 | A1 | 5/2007 | Puerta et al. |
| 2007/0172482 | A1 | 7/2007 | Sagi |
| 2007/0217997 | A1 | 9/2007 | Devy et al. |
| 2008/0076120 | A1 | 3/2008 | Donaldson et al. |
| 2009/0150315 | A1* | 6/2009 | Wirtz et al. ............... 706/46 |
| 2009/0186031 | A1 | 7/2009 | Wood et al. |
| 2009/0297449 | A1 | 12/2009 | Devy |
| 2009/0311245 | A1 | 12/2009 | Devy et al. |
| 2010/0266490 | A1 | 10/2010 | Devy et al. |

FOREIGN PATENT DOCUMENTS

| | | |
|---|---|---|
| EP | 1981538 | 7/2007 |
| WO | 2006065533 | 6/2006 |
| WO | 2007079218 | 7/2007 |
| WO | 2009079581 | 6/2009 |
| WO | 2009079585 | 6/2009 |
| WO | 2009111450 | 9/2009 |
| WO | 2009111508 | 9/2009 |
| WO | 2010048432 | 4/2010 |

OTHER PUBLICATIONS

Vizoso et al. Study or Matrix Metalloproteinases and Their Inhibitors in Breast Cancer; British Journal of Cancer, vol. 96 (2007) pp. 903-911.*

Gonzalez et al. Overexpression of Matrix Metalloproteinases in Their Inhibitors in Mononuclear Inflammatory Cells in Breast Cancer Correlates With Metastasis-Relapse; British Journal of Cancer, vol. 97 (2007) pp. 957-963.*
Ochaoenrat et al. Expression of Matrix Metalloproteinases and Their Inhibitors Correlates With Invasion and Metastasis in Squamous Cell Carcinoma of the Head and Neck; Arch. Otolaryngol. Head. Neck. Surg. vol. 127 (2001) pp. 813-820.*
Sakata et al. Expression of Matrix Metalloproteinases (MMP-2, MMP-9, MT1-MMP) and Their Inhibitors (TIMP-1, TIMP-2) in Common Epithelial Tumors of the Ovary; International Journal of Oncology, vol. 17 (2000) pp. 673-681.*
Sier et al. Tissue Levels of Matrix Metalloproteinases MMP-2 and MMP-9 Are Related to the Overall Survival of Patients With Gastric Carcinoma; British Journal of Cancer, vol. 74 (1996) pp. 413-417.*
Li et al., "Immunological Characterization of Cell-Surface and Soluble Forms of Membrane Type I Matrix Metalloproteinase in Human Breast Cancer Cells and in Fibroblasts," Molecular Carcinogeneiss, vol. 22, No. 2, pp. 84-94, Jun. 1, 1998.
Liu et al., "Eradication of large colon tumor xenografts by targeted delivery of maytansinoids", Proc. Natl. Acad. Sci. USA, Aug. 1996, vol. 93, pp. 8618-8623.
Llano et al., "Identification and Characterization of Human MT5-MMP, A New Membrane-bound Activator of Progelatinase A Overexpressed in Brain Tumors," Cancer Research, 59, pp. 2570-2576, Jun. 1, 1999.
Lopez et al., "Human Carcinoma Cell Growth and Invasiveness Is Impaired by the Propeptide of the Ubiquitous Proprotein Convertase Furin," Cancer Research, 65(10), pp. 4162-4171, May 15, 2005.
Antibody Antigen Interactions: Contact Analysis and Binding Site Topography, MacCallum et al., J. Mol. Biol. 1996, 262:732-745.
Manes et al., "Identification of Insulin-like Growth Factor-binding Protein-1 as a Potential Physiological Substrate for Human Stromelysin-3," The Journal of Biological Chemistry, 272(41), pp. 25706-25712, Oct. 10, 1997.
Maquoi et al., "Membrane Type 1 Matrix Metalloproteinase-associated Degradation of Tissue Inhibitor of Metalloproteinase 2 in Human Tumor Cell Lines," The Journal of Biological Chemistry, 275(15), pp. 11368-11378, Apr. 14, 2000.
May et al., "Plasminogen and matrix metalloproteinase activation by enzymatically modified low density lipoproteins in monocytes and smooth muscle cells," Thromb. Haemost., 93, pp. 710-715, 2005.
Minond et al., "Matrix Metalloproteinase Triple-Helical Peptidase Activities Are Differentially Regulated by Substrate Stability," Biochemistry, 43, pp. 11474-11481, 2004.
Munshi et al., "Differential Regulation of Membrane Type 1-Matrix Metalloproteinase Activity by ERK ½- and p38 MAPK-modulated Tissue Inhibitor of Metalloproteinases 2 Expression Controls Transforming Growth Factor-β1-induced Pericellular Collagenolysis," The Journal of Biological Chemistry, 279(37), pp. 39042-39050, Sep. 10, 2004.

(Continued)

*Primary Examiner* — Rebecca Prouty
*Assistant Examiner* — Paul Martin
(74) *Attorney, Agent, or Firm* — Lando & Anastasi, LLP

(57) ABSTRACT

Provided are compositions, methods and kits for quantifying the expression and/or activity of MMP-14 and other biomarkers of cancer, which may be used diagnostically and prognostically, e.g., in patient stratification and evaluation of appropriate therapeutic regimens.

19 Claims, 5 Drawing Sheets

OTHER PUBLICATIONS

Murphy et al., "Role of TIMPs (tissue inhibitors of metalloproteinases) in pericellular proteolysis: the specificity is in the detail," Biochem. Soc. Symp., 70, pp. 65-80, 2003.

Nuttall et al., "Elevated Membrane-Type Matrix Metalloproteinases in Gliomas Revealed by Profiling Proteases and Inhibitors in Human Cancer Cells," Molecular Cancer Research, vol. 1, pp. 333-345, Mar. 2003.

Ohnishi et al., "Coordinate expression of membrane type-matrix metalloproteinases-2 and 3 (MT2-MMP and MT3-MMP) and matrix metalloproteinase-2 (MMP-2) in primary and metastatic melanoma cells," European Journal of Dermatology, 11(5), pp. 420-423, Sep.-Oct. 2001.

Osenkowski et al., "Processing, Shedding, and Endocytosis of Membrane Type 1-Matrix Metalloproteinase (MT1-MMP)," Journal of Cellular Physiology, 200, pp. 2-10, 2004.

Structure of an antibody-antigen complex: Crystal Structure of the HyHEL-10 FAB-Lysozyme Complex, Padlan et al., PNAS, 1989, 86:5938-5942.

Pap et al., "Differential Expression Pattern of Membrane-Type Matrix Metalloproteinases in Rheumatoid Arthritis," Arthritis & Rheumatism, 43(6), pp. 1226-1232, Jun. 2000.

Pei, "Identification and Characterization of the Fifth Membrane-type Matrix Metalloproteinase MT5-MMP," The Journal of Biological Chemistry, 274(13), pp. 8925-8932, Mar. 26, 1999.

Peterson et al., "Monoclonal antibody form and function: Manufacturing the right antibodies 13-14 for treating drug abuse," The AAPS Journal, 2006, vol. 8, No. 2, pp. E383-E390.

Philip et al., "Matrix metalloproteinase-2: Mechanism and regulation of NF-κB-mediated activation and its role in cell motility and ECM-invasion," Glycoconjugate Journal, 21, pp. 429-441, 2004.

Pilorget et al., "Inhibition of angiogenic properties of brain endothelial cells by platelet-derived sphingosine-1-phosphate," Journal of Cerebral Blood Flow & Metabolism, 25, pp. 1171-1182, 2005.

Plaisier et al., "Involvement of Membrane-Type Matrix Metalloproteinases (MT-MMPs) in Capillary Tube Formation by Human Endometrial Microvascular Endothelial Cells: Role of MT3-MMP," The Journal of Clinical Endocrinology & Metabolism, 89(11), pp. 5828-5836, 2004.

Rajavashisth et al., "Membrane Type 1 Matrix Metalloproteinase Expression in Human Atherosclerotic Plaques: Evidence for Activation by Proinflammatory Mediators," Circulation, 99, pp. 3103-3109, 1999.

Ray et al., "Induction of the MMP-14 Gene in Macrophages of the Atherosclerotic Plaque: Role of SAF-1 in the Induction Process," Circulation Research, 95, pp. 1082-1090, 2004.

Raymond et al., "Recanalization of arterial thrombus, and inhibition with β-radiation in a new murine carotid occlusion model: mRNA expression of angiopoietins, metalloproteinases, and their inhibitors," Journal of Vascular Surgery, 40 (6), pp. 1190-1198, Dec. 2004.

Roebuck et al., Matrix Metalloproteinase Expression Is Related to Angiogenesis and Histologic Grade in Spindle Cell Soft Tissue Neoplasms of the Extremities, American Journal of Clinical Pathology, 123(3), pp. 405-414, Mar. 2005.

Romanic et al., "Upregulated expression of human membrane type-5 matrix metalloproteinase in kidneys from diabetic patients," Am J Physiol Renal Physiol, 281, F309-317, 2001.

Single amino acid substitution altering antigen-binding specificity, Rudikoff et al., PNAS, 1982, 79:1979.

Sato et al., "Roles of membrane-type matrix metalloproteinase-1 in tumor invasion and metastasis," Cancer Sci, 96 (4), pp. 212-217, Apr. 2005.

Sato et al., "Identification of the membrane-type matrix metalloproteinase MT1-MMP in osteoclasts," J. Cell Sci. (1997) vol. 110:589-596.

Savinov et al., "Inhibition of Membrane Type-1 Matrix Metalloproteinase by Cancer Drugs Interferes with the Homing of Diabetogenic T Cells into the Pancreas," The Journal of Biological Chemistry, 280(30), pp. 27755-27758, Jul. 29, 2005.

Sekine-Aizawa et al., "Matrix metalloproteinase (MMP) system in brain: identification and characterization of brain-specific MMP highly expressed in cerebellum," European Journal of Neuroscience, 13, pp. 935-948, 2001.

Sanchez-Sweatman et al., "Human Metastatic Prostate PC3 Cell Lines Degrade Bone Using Matrix Metalloproteinases," Invasion Metastasis (1998/1999) vol. 18:297-305.

Shinoda et al., "A Novel Matrix Metalloproteinase Inhibitor, FYK-1388 Suppresses Tumor Growth, Metastatis and Angiotenesis by Human Fibrasarcoma Cell Line," International Journal of Oncology, vol. 22, No. 2, pp. 281-288, Feb. 1, 2003.

Shofuda et al., "Expression of Three Membrane-type Matrix Metalloproteinases (MT-MMPs) in Rat Vascular Smooth Muscle Cells and Characterization of MT3-MMPs with and without Transmembrane Domain," The Journal of Biological Chemistry, 272(15), pp. 9749-9754, Apr. 11, 1997.

Sounni et al., "Up-regulation of Vascular Endothelial Growth Factor-A by Active Membrane-type 1 Matrix Metalloproteinase through Activation of Src-Tyrosine Kinases,", The Journal of Biological Chemistry, 279(14), pp. 13564-13574, Apr. 2, 2004.

Stadlmann et al., "Cytokine-regulated expression of collagenase-2 (MMP-8) is involved in the progression of ovarian cancer," European Journal of Cancer, 39, pp. 2499-2505, 2003.

Stawowy et al., "Furin-Like Proprotein Convertases Are Central Regulators of the Membrane Type Matrix Metalloproteinase-Pro-Matrix Metalloproteinase-2 Proteolytic Cascade in Atherosclerosis," Circulation, 111, pp. 2820-2827, 2005.

Strongin et al., "Mechanism of Cell Surface Activation of 72-κDA Type IV Collagenase," The Journal of Biological Chemistry, 270(10), pp. 5331-5338, Mar. 10, 1995.

Suenaga et al., "CD44 binding through the hemopexin-like domain is critical for its shedding by membrane-type 1 matrix metalloproteinase," Oncogene, 24, pp. 859-868, 2005.

Sun et al., "Expression of mRNA for Membrane-Type 1, 2, and 3 Matrix Metalloproteinases in Human Laryngeal Cancer," Chinese Medical Sciences Journal, 19(3), pp. 170-173, Sep. 2004.

Szabova et al., "Expression Pattern of Four Membrane-Type Matrix Metalloproteinases in the Normal and Diseased Mouse Mammary Gland," Journal of Cellular Physiology, 205, pp. 123-132, 2005.

Takino et al., "Identification of the Second Membrane-type Matrix Metalloproteinase (MT-MMP-2) Gene from a Human Placenta cDNA Library," The Journal of Biological Chemistry, 270(39), pp. 23013-23020, Sep. 29, 1995.

Tanimura et al., "Specific blockade of the ERK pathway inhibits the invasiveness of tumor cells: down-regulation of matrix metalloproteinase-3/-9/-14 and CD 44," Biochemical and Biophysical Research Communications, 304, pp. 801-806, 2003.

Tchetina et al., "Increased Type II Collagen Degradation and Very Early Focal Cartilage Degeneration Is Associated with Upregulation of Chondrocyte Differentiation Related Genes in Early Human Articular Cartilage Lesions," The Journal of Rheumatology, 32(5), pp. 876-886, 2005.

Tornetta et al., "Isolated of human anti-idiotypic antibodies by phage display for clinical immune response assays" Journal of Immunological Methods, vol. 328, pp. 34-44, 2007.

Toth et al., "Pro-MMP-9 activation by the MT1-MMP/MMP-2 axis and MMP-3: role of TIMP-2 and plasma membranes," Biochemical and Biophysical Research Communications, 308, pp. 386-395, 2003.

Udayakumar et al., "Fibroblast Growth Factor-I Transcriptionally Induces Membrane Type-I Matrix Metalloproteinase Expression in Prostate Carcinoma Cell Line," The Prostate, 58, pp. 66-75, 2004.

Ueno et al., "Expression and Tissue Localization of Membrane-Types 1, 2, and 3 Matrix Metalloproteinases in Human Invasive Breast Carcinomas," Cancer Research, 57, pp. 2055-2060, May 15, 1997.

Uzui et al., "Increased Expression of Membrane Type 3-Matrix Metalloproteinase in Human Atherosclerotic Plaque: Role of Activated Macrophages and Inflammatory Cytokines," Circulation, 106, pp. 3024-3030, 2002.

Van Meter et al., "Induction of membrane-type-1 matrix metalloproteinase by epidermal growth factor-mediated signaling in gliomas," Neuro-Oncology, pp. 188-199, Jul. 2004.

Wan et al., "Effects of losartan on MT3-MMP and TIMP2 mRNA expressions in diabetic rat kidney," Journal of First Military Medical University, 24(12), pp. 1391-1394, Dec. 2004, abstract only.

Wang et al., "Expression, purification and characterization of recombinant mouse MT5-MMP protein products," FEBS Letters, 462, pp. 261-266, 1999.

Wang et al., "The Hemopexin Domain of Membrane-type Matrix Metalloproteinase-1 (MT1-MMP) Is Not Required for Its Activation of proMMP2 on Cell Surface but Is Essential for MT1-MMP-mediated Invasion in Three-dimensional Type I Collagen," The Journal of Biological Chemistry, 279(49), pp. 51148-51155, Dec. 3, 2004.

Winding et al., "Synthetic Matrix Metalloproteinase Inhibitors Inhibit Growth of Established Breast Cancer Osteolytic Lesions and Prolong Survival in Mice," Clinical Cancer Research, Jun. 2002, vol. 8:1932-1939.

Yoshiyama et al., "Expression of the membrane-type 3 matrix metalloproteinase (MT3-MMP) in human brain tissue," Acta Neuropathol, 96, pp. 347-350, 1998.

Zhao et al., "Differential Inhibition of Membrane Type 3 (MT3)-Matrix Metalloproteinase (MMP) and MT1-MMP by Tissue Inhibitor of Metalloproteinase (TIMP)-2 and TIMP-3 Regulates Pro-MMP-2 Activation," The Journal of Biological Chemistry, 279(10), pp. 8592-8601, Mar. 5, 2004.

Zucker et al., "Imaging metalloproteinase activity in vivo," Nature Medicine, 7(6), pp. 655-656, Jun. 2001.

Zucker et al., "Membrane Type-Matrix Metalloproteinases (MT-MMP)," Current Topics in Developmental Biology, 54, pp. 1-74, 2003.

Zucker et al., "Role of matrix metalloproteinases (MMPs) in colorectal cancer," Cancer and Metastasis Reviews, vol. 23, pp. 101-117, 2004.

OMIM Accession No. 600754; Matrix Metalloproteinase 14; Aug. 28, 1995.

International Search Report dated May 14, 2008 from corresponding International PCT Application PCT/US2006/049556.

International Preliminary Report on Patentability and Written Opinion dated Jul. 1, 2008 from corresponding International PCT Application PCT/US2006/049556.

International Search Report dated May 15, 2009 from International Application No. PCT/US09/32384.

International Search Report including Written Opinion dated Oct. 8, 2009 from International Application No. PCT/US09/41632.

International Search Report including Written Opinion dated Jun. 1, 2009 from International Application No. PCT/US08/87236.

Extended European Search Report dated Apr. 8, 2010 from European Application No. EP06848335.3.

Anilkumar et al., "Palmitoylation at Cys574 is essential for MT1-MMP to promote cell migration,"The FASEB Journal, pp. 1-18, Jun. 9, 2005.

Aoki et al., "Cleavage of Apolipoprotein E by Membrane-Type Matrix Metalloproteinase-1 Abrogates Suppression of Cell Proliferation," J. Biochem. 137, pp. 95-99 (2005).

Bauvois, "Transmembrane proteases in cell growth and invasion: new contributors to angiogenesis?," Oncogene, 23, pp. 317-329, 2004.

Berno et al., "The 67 κDa laminin receptor increases tumor aggressiveness by remodeling laminin-1," Endocrine-Related Cancer, 12, pp. 393-406 (2005).

Humanization of Rodent Monoclonal Antibodies by CDR Grafting, Bendig Methods: A Companion to Methods in Enzymology 1995:8:83-93.

Butler et al., "The TIMP2 Membrane Type 1 Metalloproteinase "Receptor" Regulates the Concentration and Efficient Activation of Progelatinase A," The Journal of Biological Chemistry, 273(2), pp. 871-880, Jan. 9, 1998.

Cao et al., "Membrane type I-matrix metalloproteinase promotes human prostate cancer invasion and metastasis," Thromb Haemost, 93, p. 770-778, 2005.

Cao et al., "Membrane Type Matrix Metalloproteinase 1 Activates Pro-gelatinase A without Furin Cleavage of the N-terminal Domain," The Journal of Biochemistry, 271(47), pp. 30174-30180, Nov. 22, 1996.

Chang et al., "Activation Systems for Latent Matrix Metalloproteinase-2 Are Upregulated Immediately After Focal Cerebral Ischemia," Journal of Cerebral Blood Flow & Metabolism, 23, pp. 1408-1419, 2003.

Deryugina et al., "Unexpected Effect of Matrix Metalloproteinase Down-Regulation on Vascular Intravasation and Metastasis of Human Fibrosarcoma Cells Selected in vivo for High Rates of Dissemination," Cancer Res., 65(23), pp. 10959-10969, Dec. 1, 2005.

Devy et al., "Potent and selective antibody inhibitor of human matrix metalloproteinase-14 (MMP-14) inhibits tumor growth, invasion and angiogenesis," American Society of Clinical Oncology [Online], 2007 (retrieved online on Sep. 29, 2009), retrieved from the internet at URL:http://www.asco.org/ASCOv2IMeetings/Abstracts &vmview=abst_detail_view&confID=52&abstractID=40128; abstract.

Distler et al., "The induction of matrix metalloproteinase and cytokine expression in synovial fibroblasts stimulated with immune cell microparticles," PNAS, 102(8), pp. 2892-2897, Feb. 22, 2005.

Dong et al., "Expression of Membrane-Type Matrix Metalloproteinases 4, 5, and 6 in Mouse Corneas Infected with P. aeruginosa," Investigative Ophthalmology & Visual Science, 42(13), pp. 3223-3227, Dec. 2001.

Dong et al., "Matrix Metalloproteinase Activity and Osteoclasts in Experimental Prostate Cancer Bone Metastasis Tissue," American Journal of Pathology, 166(4), pp. 1173-1186, Apr. 2005.

El Bedoui et al., "Catechins prevent vascular smooth muscle cell invasion by inhibiting MT1-MMP activity and MMP-2 expression," Cardiovascular Research, 67, pp. 317-315, 2005.

Folgueras et al., "Matrix metalloproteinases in cancer: from new functions to improved inhibition strategies," Int. J. Dev. Biol., 48, pp. 411-424 (2004).

Galvez et al., "Membrane Type 1-Matrix Metalloproteinase Is Regulated by Chemokines Monocyte-Chemoattractant Protein-1/CCL2 and Interleukin-8/CXCL8 in Endothelial Cells during Angiogenesis," The Journal of Biological Chemistry, 280(2), pp. 1292-1298, Jan. 14, 2005.

Galvez et al., "Membrane Type 1-Matrix Metalloproteinase Is Activated during Migration of Human Endothelial Cells and Modulates Endothelial Motility and Matrix Remodeling," The Journal of Biological Chemistry, 276(40), pp. 37491-37500, Oct. 5, 2001.

Giebel et al., "Matrix metalloproteinases in early diabetic retinopathy and their role in alteration of the blood-retinal barrier," Laboratory Investigation, 85, pp. 597-607, 2005.

Gilles et al., "Contribution of MT1-MMP and of human laminin-5 □2 chain degradation to mammary epithelial cell migration," Journal of Cell Science, 114, pp. 2967-2976, 2001.

Gilles et al., "Implication of Collagen Type I-Induced Membrane-Type 1-Matrix Metalloproteinase Expression and Matrix Metalloproteinase-2 Activation in the Metastatic Progression of Breast Carcinoma," Laboratory Investigation, 76 (5), pp. 651-660, 1997.

Goldbach-Mansky et al., "Active synovial matrix metalloproteinase-2 is associated with radiographic erosions in patients with early synovitis," Arthritis Res., 2, pp. 145-153, 2000.

Grossman, "Profiling the evolution of human metastatic bladder cancer," Urologic Oncology: Seminars and Original Investigations, 23, p. 222, 2005.

Grossman, "Small cell carcinoma of the urinary bladder: a clinicopathologic analysis of 64 patients," Urologic Oncology: Seminars and Original Investigations, 23, p. 222-223, 2005.

Guo et al., "Up-Regulation of Angiopoietin-2, Matrix Metalloprotease-2, Membrane Type 1 Metalloprotease, and Laminin 5 □2 Correlates with the Invasiveness of Human Glioma," American Journal of Pathology, 166(3), pp. 877-890, Mar. 2005.

Haas, "Endothelial cell regulation of matrix metalloproteinases," Can. J. Physiol. Pharmacol., 83, pp. 1-7, 2005.

Handsley et al., "Metalloproteinases and their inhibitors in tumor angiogenesis," Int. J. Cancer, 115, pp. 849-860, 2005.

Harrison et al., "The influence of CD44v3-v10 on adhesion, invasion and MMP-14 expression in prostate cancer cells," Oncology Reports, 15, pp. 199-206, 2006.

Hayashita-Kinoh et al., "Membrane-Type 5 Matrix Metalloproteinase Is Expressed in Differentiated Neurons and Regulates Axonal Growth," Cell Growth & Differentiation, 12, pp. 573-580, Nov. 2001.

Hernandez-Barrantes et al., "Regulation of membrane type-matrix metalloproteinases," Cancer Biology, 12, pp. 131-138, 2002.

Holmbeck et al., "MT1-MMP-Deficient Mice Develop Dwarfism, Osteopenia, Arthritis, and Connective Tissue Disease due to Inadequate Collagen Turnover," Cell, 99, pp. 81-92, Oct. 1, 1999.

Hotary et al., "Matrix Metalloproteinases (MMPs) Regulate Fibrin-invasive Activity via MT1-MMP-dependent and—independent Processes," J. Exp. Med., 195(3), pp. 295-308, Feb. 4, 2002.

Hwang et al., "A proteomic approach to identify substrates of matrix metalloproteinase-14 in human plasma," Biochimica et Biophysica Acta, 1702, pp. 79-87, 2004.

Iida et al., "Melanoma Chondroitin Sulfate Proteoglycan Regulates Matrix Metalloproteinase-dependent Human Melanoma Invasion into Type I Collagen," The Journal of Biological Chemistry, 276(22), pp. 18786-18794, Jun. 1, 2001.

Itoh et al., "MT1-MMP: A Potent Modifier of Pericellular Microenvironment," Journal of Cellular Physiology, 206, pp. 1-8, 2006.

Jaworski et al., "Developmental regulation of membrane type-5 matrix metalloproteinase (MT5-MMP) expression in the rat nervous system," Brain Research, 860, pp. 174-177, 2000.

Kang et al., "Functional characterization of MT3-MMP in transfected MDCK cells: progelatinase A activation and tubulogenesis in 3-D collagen lattice," The FASEB Journal, 14, pp. 2559-2568, Dec. 2000.

Kevorkian et al., "Expression Profiling of Metalloproteinases and Their Inhibitors in Cartilage," Arthritis & Rheumatism, 50(1), pp. 131-141, Jan. 2004.

Kinoshita et al., "TIMP-2 Promotes Activation of Progelatinase A by Membrane-type 1 Matrix Metalloproteinase Immobilized on Agarose Beads," The Journal of Biological Chemistry, 273(26), pp. 16098-16103, Jun. 26, 1998.

Kitagawa et al., "Expression of Messenger RNAs for Membrane-Type 1, 2, and 3 Matrix Metalloproteinases in Human Renal Cell Carcinomas," The Journal of Urology, 162, pp. 905-909, Sep. 1999.

Kluft, "The Fibrinolytic System and Thrombotic Tendency," Pathophysiology of Haemostasis and Thrombosis, vol. 33, No. 5-6, pp. 425-429, Sep.-Oct. 2003/2004.

Knauper et al., "Cellular Mechanisms for Human Procollagenase-3 (MMP-13) Activation," The Journal of Biological Chemistry, 271(29), pp. 17124-17131, Jul. 19, 1996.

Komori et al., "Absence of mechanical allodynia and Aβ-fiber sprouting after sciatic nerve injury in mice lacking membrane-type 5 matrix metalloproteinase," FEBS Letters, 557, pp. 125-128, 2004.

Konaka et al., "A Human Seminoma Xenograft Model With Regional Lymph Node Metastasis," The Journal of Urology, 161, pp. 342-248, Jan. 1999.

Koshida et al., "Correlation Between Expression of Metastasis-Related Genes and Lymph Node Metastasis in Testicular Cancer," Acta Urol. Jpn., 46(10), pp. 775-781, Oct. 2000.

Kousidou et al., "Genistein suppresses the invasive potential of human breast cancer cells through transcriptional regulation of metalloproteinases and their tissue inhibitors," International Journal of Oncology, 26(4), pp. 1101-1109, Apr. 2005.

Lafleur et al., "Endothelial tubulogenesis within fibrin gels specifically requires the activity of membrane-type-matrix metalloproteinases (MT-MMPs)," Journal of Cell Science, 115(17), pp. 3427-3438, 2002.

Lafleur et al., "Upregulation of matrix metalloproteinases (MMPs) in breast cancer xenografts: a major induction of stromal MMP-13," Int. J. Cancer, 114, pp. 544-554 (2005).

Lee et al., "Unveiling the Surface Epitopes That Render Tissue Inhibitor of Metalloproteinase-1 Inactive against Membrane Type 1-Matrix Metalloproteinase," The Journal of Biological Chemistry, 278(41), pp. 40224-40230, Oct. 10, 2003.

Lee et al., "A matrix metalloproteinase inhibitor, batimastat, retards the development of osteolytic bone metastase by MDA-MB-231 human breast cancer cells in Balb C nu/nu mice," Eur. J. Cancer, Jan. 2001, 37(1):106-13.

International Search Report including Written Opinion from corresponding International Application No. PCT/US08/87230, mailed Feb. 24, 2009.

Bergers et al., "Extrinsic Regulators of Epithelial Tumor Progression: Metalloproteinases", Current Opinion in Genetics and Development, 10:120-127, 2000.

Itoh, "MT1-MMP: A Key Regulator of Cell Migration in Tissue", IUBMB Life, 58(10):589-596, Oct. 2006.

Jiang et al., "Expression of Membrane Type-1 Matrix Metalloproteinase, MT1-MMP in Human Breast Cancer and its Impact on Invasiveness of Breast Cancer Cells", Int. J. Mol. Med., 17:583-590, 2006.

Paquette et al., "In Vitro Irradiation of Basement Membrane Enhances the Invasiveness of Breast Cancer Cells", British Journal of Cancer, 97:1505-1512, 2007.

Trisciuoglio et al., "Bcl-2 Overexpression in Melanoma Cells Increases Tumor Progression-Associated Properties and in Vivo Tumor Growth," Journal of Cellular Physiology, 205, pp. 414-421, 2005.

Choi et al., "Expression of Matrix Metalloproteinases in the Muscle of Patients with Inflammatory Myopathies", Neurology, vol. 54, Issue 1, Jan. 2000.

* cited by examiner

FIGURE 1: Expression of Select MMPs in Different Cancer Cell Lines

| Cell line | TGI (%) DX-2400 (10mg/kg) | *MMP-14 (GUAVA) | *MMP-15 (GUAVA) | MMP-2 activity (zymo) | MMP-9 activity (zymo) |
|---|---|---|---|---|---|
| BxPC-3 | 0 | ++ | - | - | +++ |
| MCF-7 | 25 | ++ | +++ | - | + |
| MDA-MB-435 | 35 | +++ | +++ | ND | - |
| BT-474 | 50 | +++ | +++ | - | - |
| MDA-MB-231 | >50% | +++ | - | +++ | - |
| PC-3 | >50% | +++ | - | - | - |
| B16-F1 | 35-40% | ++ | + | ND | - |

* +++: positive cells > 50%; ++: 20% < positive cells < 50%; +: positive cells > 20%

FIGURE 2: Effect of DX-2400 on Tumor Progression in Different Breast Cancer Xenograft Models

| Human Tumor Xenograft | Tumor Type | Treatment | % of Tumor Growth Inhibition (TGI) |
|---|---|---|---|
| MDA-MB-231 Orthotopic implantation | ER neg. HER2 neg. | DX-2400 10mg/kg IP Q2D for 28 days | 75% ($p<0.001$) |
| | | DX-2400 0.1, 1, and 10mg/kg IP Q2D for 28 days | 24% at 0.1mg/kg ($p<0.05$) 29% at 1mg/kg ($p<0.05$) 54% at 10mg/kg ($p<0.001$) |
| | | DX-2400 10mg/kg IP Q2D for 57 days | 70% |
| | | DX-2400 10mg/kg IP Q2D in combo with Bevacizumab 1 or 5mg/kg twice per week for 57 days | >70% in combo with Bevacizumab |
| MDA-MB-435 Orthotopic implantation | ER neg. HER2 neg. | DX-2400 0.1, 1, and 10mg/kg IP Q2D for 61 days | 34% at 1 and 10mg/kg ($p<0.05$) |
| MCF7 | ER positive HER2 neg. | DX-2400 0.1, 1, and 10mg/kg IP Q2D for 28 days | 30% at 10mg/kg ($p<0.05$) |
| BT-474 1 mm³ tumor fragments s.c. | ER pos. HER2 pos. | DX-2400 0.1, 1, and 10mg/kg IP Q2D for 35 days | 8% at 0.1mg/kg ($p<0.05$) 22% at 1mg/kg ($p<0.05$) 48% at 10mg/kg ($p<0.001$) |

FIGURE 3: Effect of DX-2400 on Tumor Progression in Different Xenograft Models

| Tumor Xenograft | Tumor Type | Treatment | % of Tumor Growth Inhibition (TGI) |
|---|---|---|---|
| PC-3 (s.c.) | Human, prostate ADC Grade IV Androgen-independent, HER2 neg. | DX-2400 0.1, 1, and 10mg/kg IP Q2D for 42 days | 29% at 0.1mg/kg<br>48% at 1mg/kg ($p<0.001$)<br>82% at 10mg/kg ($p<0.001$) |
| B16F1 (s.c.) | Mouse Melanoma (s.c.) | DX-2400 0.1, 1, and 10mg/kg IP Q2D for 14 days | 25% at 0.1mg/kg ($p<0.05$)<br>38% at 1mg/kg ($p<0.05$)<br>28% at 10mg/kg ($p<0.05$) |
| BxPC-3 (s.c.) | Human, Pancreatic cancer | DX-2400 0.1, 1, and 10mg/kg IP Q2D for 32 days | No response<br>Being repeated |

FIGURE 4: Effect of DX-2400 on Metastasis Incidence in Different Xenograft Models

| Tumor model | Tumor Type | Treatment | % inhibition of Metastases |
|---|---|---|---|
| B16-F1 (i.v.) | Mouse Melanoma | DX-2400 0.1, 1, and 10mg/kg IP Q2D for 14 days | 23% inhibition of lung nodules at 1mg/kg (p<0.05) 70% inhibition of lung nodules at 10mg/kg (p<0.001) |
| MDA-MB-231 Orthotopic Implantation | Human breast cancer ER neg. HER2 neg. | DX-2400 10mg/kg IP Q2D for 28 days | 60% inhibition of lung nodules (p<0.05) 25% inhibition of liver nodules (p<0.05) |
| MDA-MB-435 Orthotopic Implantation | Human breast cancer ER neg. HER2 neg. | DX-2400 (0.1, 1 and 10mg/kg IP) Q2D for 61 days | No significant differences in metastasis incidence in axillary lymph nodes and lung between the treatment groups and PBS control |
| PC-3 (intratibial) | Human, prostate ADC Grade IV Androgen-independent | DX-2400 (10mg/kg IP) Q2D for 14 days | 63% inhibition of bone lesions |

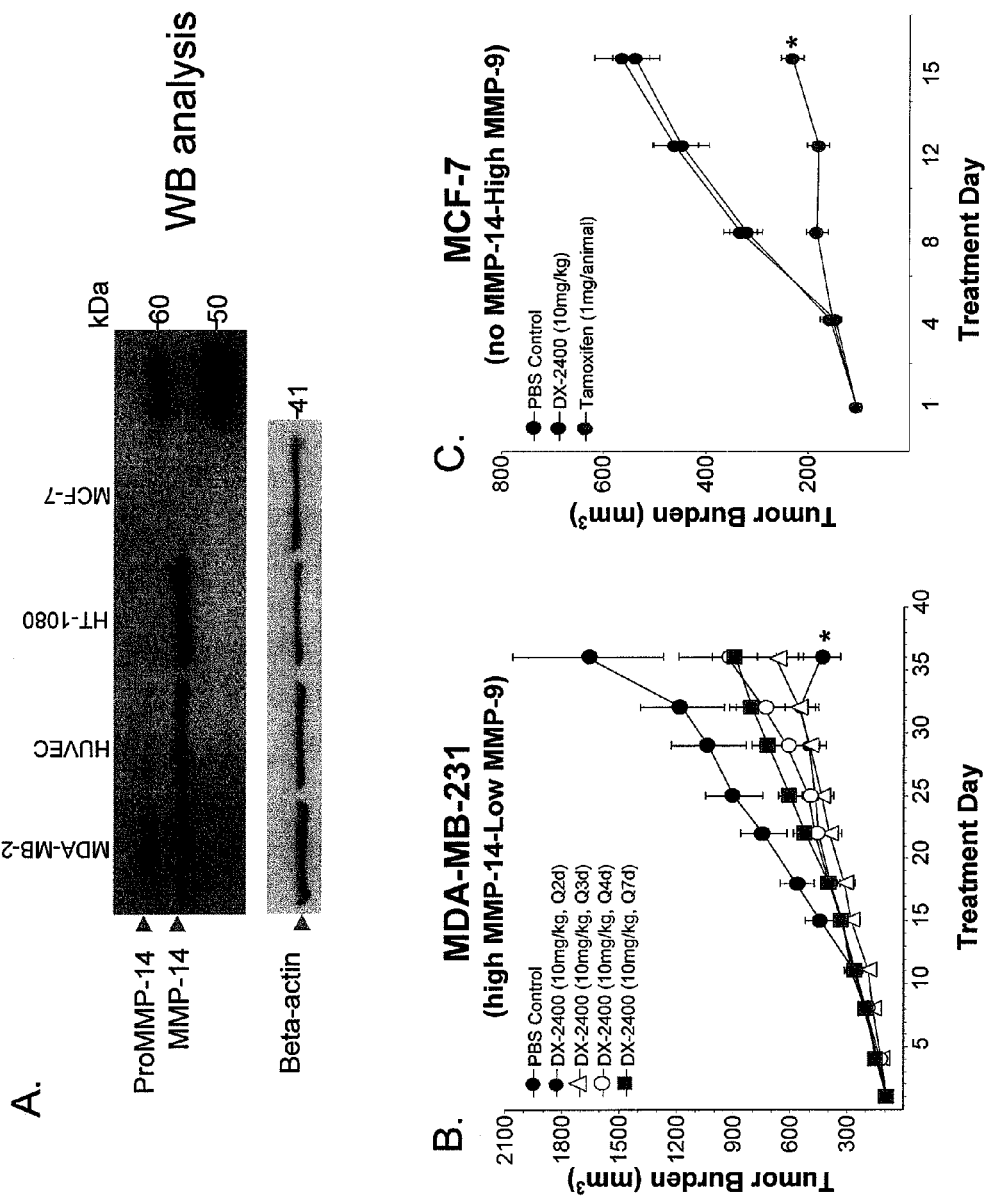

SEQUENCE LISTING

```
<160> NUMBER OF SEQ ID NOS: 46

<210> SEQ ID NO 1
<211> LENGTH: 582
<212> TYPE: PRT
<213> ORGANISM: Homo sapiens

<400> SEQUENCE: 1

Met Ser Pro Ala Pro Arg Pro Pro Arg Cys Leu Leu Leu Pro Leu Leu
1               5                   10                  15

Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

Asp Leu Arg Thr His Thr Gln Arg Ser Pro Gln Ser Leu Ser Ala Ala
    50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
            260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
    290                 295                 300
```

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
            325                 330                 335

Lys Glu Arg Trp Phe Trp Arg Val Arg Asn Asn Gln Val Met Asp Gly
        340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Leu Arg Ala Val Asp Ser Glu
        435                 440                 445

Tyr Pro Lys Asn Ile Lys Val Trp Glu Gly Ile Pro Glu Ser Pro Arg
450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Thr Glu Val Ile Ile Ile Glu
        515                 520                 525

Val Asp Glu Glu Gly Gly Gly Ala Val Ser Ala Ala Ala Val Val Leu
530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
            580

<210> SEQ ID NO 2
<211> LENGTH: 582
<212> TYPE: PRT
<213> ORGANISM: Mus musculus

<400> SEQUENCE: 2

Met Ser Pro Ala Pro Arg Pro Ser Arg Ser Leu Leu Pro Leu Leu
1               5                   10                  15

Thr Leu Gly Thr Ala Leu Ala Ser Leu Gly Trp Ala Gln Gly Ser Asn
                20                  25                  30

Phe Ser Pro Glu Ala Trp Leu Gln Gln Tyr Gly Tyr Leu Pro Pro Gly
            35                  40                  45

Asp Leu Arg Thr His Thr Gln Arg Ser Pro Gln Ser Leu Ser Ala Ala
        50                  55                  60

Ile Ala Ala Met Gln Lys Phe Tyr Gly Leu Gln Val Thr Gly Lys Ala
65                  70                  75                  80

Asp Leu Ala Thr Met Met Ala Met Arg Arg Pro Arg Cys Gly Val Pro
                85                  90                  95

Asp Lys Phe Gly Thr Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
            115                 120                 125

Gln Asn Tyr Thr Pro Lys Val Gly Glu Tyr Ala Thr Phe Glu Ala Ile
            130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                    165                 170                 175

Ile Met Ile Leu Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
            195                 200                 205

Ile Gly Gly Asp Thr His Phe Asp Ser Ala Glu Pro Trp Thr Val Gln
            210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Asn Asp Pro Ser Ala Ile
                    245                 250                 255

Met Ser Pro Phe Tyr Gln Trp Met Asp Thr Glu Asn Phe Val Leu Pro
            260                 265                 270

Asp Asp Asp Arg Arg Gly Ile Gln Gln Leu Tyr Gly Ser Lys Ser Gly
            275                 280                 285

Ser Pro Thr Lys Met Pro Pro Gln Pro Arg Thr Thr Ser Arg Pro Ser
            290                 295                 300

Val Pro Asp Lys Pro Lys Asn Pro Ala Tyr Gly Pro Asn Ile Cys Asp
305                 310                 315                 320

Gly Asn Phe Asp Thr Val Ala Met Leu Arg Gly Glu Met Phe Val Phe
                    325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
            355                 360                 365

Asn Thr Ala Tyr Glu Arg Lys Asp Gly Lys Phe Val Phe Phe Lys Gly
            370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                    405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Phe Arg Ala Val Asp Ser Glu
            435                 440                 445

Tyr Pro Lys Asn Ile Lys Val Trp Glu Gly Ile Pro Glu Ser Pro Arg
            450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                    485                 490                 495

Tyr Pro Lys Ser Ala Leu Arg Asp Trp Met Gly Cys Pro Ser Gly Arg
            500                 505                 510

Arg Pro Asp Glu Gly Thr Glu Glu Glu Thr Glu Val Ile Ile Ile Glu
            515                 520                 525

```
Val Asp Glu Glu Gly Ser Gly Ala Val Ser Ala Ala Val Val Leu
    530                 535                 540
Pro Val Leu Leu Leu Leu Val Leu Ala Val Gly Leu Ala Val Phe
545                 550                 555                 560
Phe Phe Arg Arg His Gly Thr Pro Lys Arg Leu Leu Tyr Cys Gln Arg
            565                 570                 575
Ser Leu Leu Asp Lys Val
            580

<210> SEQ ID NO 3
<211> LENGTH: 3437
<212> TYPE: DNA
<213> ORGANISM: Homo sapiens

<400> SEQUENCE: 3
aagttcagtg cctaccgaag acaaaggcgc cccgagggag tggcggtgcg accccagggc      60
gtgggcccgg ccgcggagcc cacactgccc ggctgacccg gtggtctcgg accatgtctc     120
ccgccccaag accccccgt tgtctcctgc tcccctgct cacgctcggc accgcgctcg      180
cctccctcgg ctcggcccaa agcagcagct tcagccccga agcctggcta cagcaatatg     240
gctacctgcc tcccggggac ctacgtaccc acacacagcg ctcacccag tcactctcag      300
cggccatcgc tgccatgcag aagttttacg gcttgcaagt aacaggcaaa gctgatgcag     360
acaccatgaa ggccatgagg cgccccgat gtggtgttcc agacaagttt ggggctgaga      420
tcaaggccaa tgttcgaagg aagcgctacg ccatccaggg tctcaaatgg caacataatg     480
aaatcacttt ctgcatccag aattacaccc caaggtgggc gagtatgcc acatacgagg      540
ccattcgcaa ggcgttccgc gtgtgggaga gtgccacacc actgcgcttc cgcgaggtgc     600
cctatgccta catccgtgag ggccatgaga agcaggccga catcatgatc ttctttgccg      660
agggcttcca tggcgacagc acgccccttcg atggtgaggg cggcttcctg cccatgcct     720
acttcccagg ccccaacatt ggaggagaca cccactttga ctctgccgag ccttggactg     780
tcaggaatga ggatctgaat ggaaatgaca tcttcctggt ggctgtgcac gagctgggcc     840
atgccctggg gctcgagcat ccagtgacc cctcggccat catggcaccc ttttaccagt      900
ggatggacac ggagaatttt gtgctgcccg atgatgaccg ccggggcatc cagcaacttt     960
atgggggtga gtcagggttc cccaccaaga tgcccctca acccaggact acctcccggc    1020
cttctgttcc tgataaaccc aaaaacccca cctatgggcc caacatctgt gacgggaact     1080
ttgacaccgt ggccatgctc cgaggggaga tgtttgtctt caaggagcgc tggttctggc    1140
gggtgaggaa taccaagtg atggatggat acccaatgcc cattggccag ttctggcggg    1200
gcctgcctgc gtccatcaac actgcctacg agaggaagga tggcaaattc gtcttcttca    1260
aggagacaa gcattgggtg tttgatgagg cgtcccctgga acctggctac cccaagcaca    1320
ttaaggagct gggccgaggg ctgcctaccg acaagattga tgctgctctc ttctggatgc    1380
ccaatgaaaa gacctacttc ttccgtggaa acaagtactac cgtttcaac gaagagctca    1440
gggcagtgga tagcgagtac cccaagaaca tcaaagtctg gaagggatcc ctgagtctc    1500
ccagagggtc attcatgggc agcgatgaag tcttcactta cttctacaag gggaacaaat    1560
actgaaaatt caacaaccag aagctgaagg tagaaccggg ctaccccaag tcagccctga    1620
gggactggat gggctgccca tcgggaggcc ggccggatga ggggactgag gaggagacgg    1680
aggtgatcat cattgaggtg gacgaggagg gcggcggggc ggtgagcgcg gctgccgtgg    1740
tgctgcccgt gctgctgctg ctcctggtgc tggcggtggg ccttgcagtc ttcttcttca    1800
```

```
gacgccatgg gaccccagg cgactgctct actgccagcg ttccctgctg gacaaggtct    1860
gacgcccacc gccggcccgc ccactcctac acaaggact ttgcctctga aggccagtgg    1920
cagcaggtgg tggtgggtgg gctgctccca tcgtcccgag ccccctcccc gcagcctcct    1980
tgcttctctc tgtcccctgg ctggcctcct tcaccctgac cgcctccctc cctcctgccc    2040
cggcattgca tcttccctag ataggtcccc tgagggctga gtgggagggc ggccctttcc    2100
agcctctgcc cctcagggga accctgtagc tttgtgtctg tccagcccca tctgaatgtg    2160 ttggggctc tgcacttgaa ggcaggaccc tcagacctcg ctggtaaagg tcaaatgggg     2220
tcatctgctc cttttccatc ccctgacata ccttaacctc tgaactctga cctcaggagg    2280
ctctgggcac tccagccctg aaagcccag gtgtacccaa ttggcagcct ctcactactc     2340
tttctggcta aaaggaatct aatcttgttg agggtagaga ccctgagaca gtgtgagggg    2400
gtggggactg ccaagccacc ctaagacctt ggaggaaaa ctcagagagg gtcttcgttg     2460
ctcagtcagt caagttcctc ggagatctgc ctctgcctca cctaccccag gaacttcca    2520 aggaaggagc ctgagccact ggggactaag tgggcagaag aaaccttgg cagccctgtg     2580 cctctcgaat gttagccttg gatgggctt tcacagttag aagagctgaa accagggtg     2640 cagctgtcag gtagggtggg gccggtggga gaggcccggg tcagagccct gggggtgagc    2700
ctgaaggcca cagagaaaga accttgccca aactcaggca gctggggctg aggcccaaag    2760
gcagaacagc cagaggggc aggagggac caaaaggaa aatgaggacg tgcagcagca      2820
ttggaaggct gggccgggc aggccaggcc aagccaagca gggggccaca gggtgggctg     2880
tggagctctc aggaagggcc ctgaggaagg cacacttgct cctgttggtc cctgtccttg    2940
ctgcccaggc agcgtggagg ggaagggtag ggcagccaga gaaaggagca gagaaggcac    3000
acaaacgagg aatgaggggc ttcacgagag gccacagggc ctggctggcc acgctgtccc    3060
ggcctgctca ccatctcagt gaggggcagg agctggggct cgcttaggct gggtccacgc    3120
ttccctggtg ccagcacccc tcaagcctgt ctcaccagtg gcctgccctc tcgctccccc    3180
acccagccca cccattgaag tctccttggg ccaccaaagg tggtggccat ggtaccgggg    3240
acttgggaga gtgagaccca gtggagggag caagaggaga gggatgtcgg gggggtgggg    3300
cacggggtag gggaaatggg gtgaacggtg ctggcagttc ggctagattt ctgtcttgtt    3360 tgttttttg ttttgtttaa tgtatatttt tattataatt attatatatg aattccaaaa    3420
aaaaaaaaaa aaaaaaa                                                   3437
```

<210> SEQ ID NO 4
<211> LENGTH: 2583
<212> TYPE: DNA
<213> ORGANISM: Mus musculus

<400> SEQUENCE: 4

```
caaaggagag cagagagggc ttccaactca gttcgccgac taagcagaag aaagatcaaa      60
aacggaaaag agaagagcaa acagacattt ccaggagcaa ttccctcacc tccaagccga    120
ccgcgctcta ggaatccaca ttccgttcct ttagaagaca aaggcgcccc aagagaggcg    180
gcgcgacccc agggcgtggg ccccgccgcg gagcccgcac cgcccggcgc ccgacgccg     240 gggaccatgt ctcccgcccc tcgaccctcc cgcagcctcc tgctcccct gctcacgctt    300 ggcacggcgc tcgcctccct cggctgggcc caaggcagca acttcagccc cgaagcctgg    360
ctgcagcagt atggctacct acctccaggg gacctgcgta cccacacaca acgctcaccc    420
cagtcactct cagctgccat tgccgccatg caaaagttct atggtttaca agtgacaggc    480
```

```
aaggctgatt tggcaaccat gatggccatg aggcgccctc gctgtggtgt tccggataag      540
tttgggactg agatcaaggc caatgttcgg aggaagcgct atgccattca gggcctcaag      600
tggcagcata atgagatcac tttctgcatt cagaattaca cccctaaggt gggcgagtat      660
gccacattcg aggccattcg aaggccttc cgagtatggg agagtgccac gccactgcgc       720
ttccgagaag tgccctatgc ctacatccgg gagggacatg agaagcaggc tgacatcatg      780
atcttatttg ctgagggttt ccacggcgac agtacaccct tgatggtga aggagggttc       840 ctggctcatg cctacttccc aggccccaat attggagggg atacccactt tgattctgcc      900
gagccctgga ctgtccaaaa tgaggatcta aatgggaatg acatcttctt ggtggctgtg     960
catgagttgg ggcatgccct aggcctggaa cattctaacg atccctccgc catcatgtcc     1020 ccctttacc agtggatgga cacagagaac ttcgtgttgc ctgatgacga tcgccgtggc      1080
atccagcaac tttatggaag caagtcaggg tcacccacaa agatgccccc tcaacccaga     1140
actacctctc ggccctctgt cccagataag cccaaaaacc ccgcctatgg gcccaacatc     1200
tgtgacggga actttgacac cgtggccatg ctccgaggag agatgtttgt cttcaaggag     1260
cgatggttct ggcgggtgag gaataaccaa gtgatggatg atacccaat gcccattggc      1320 caattctgga ggggcctgcc tgcatccatc aatactgcct acgaaaggaa ggatggcaaa     1380
tttgtcttct tcaaaggaga taagcactgg gtgtttgacg aagcctccct ggaacccggg     1440
taccccaagc acattaagga gcttggccga gggctgccca cggacaagat cgatgcagct     1500
ctcttctgga tgcccaatgg gaagacctac ttcttccggg caataagta ctaccggttc      1560 aatgaagaat tcagggcagt ggacagcgag tacctaaaa acatcaaagt ctgggaagga     1620
atccctgaat ctcccagggg gtcattcatg ggcagtgatg aagtcttcac atacttctac     1680
aagggaaaca atactggaa gttcaacaac cagaagctga aggtagagcc agggtacccc      1740
aagtcagctc tgcgggactg gatgggctgc ccttcggggc gccggcccga tgaggggact     1800
gaggaggaga cagaggtgat catcattgag gtggatgagg agggcagtgg agctgtgagt     1860
gcggccgccg tggtcctgcc ggtactactg ctgctcctgg tactggcagt gggcctcgct     1920
gtcttcttct tcagacgcca tgggacgccc aagcgactgc tttactgcca gcgttcgctg     1980
ctggacaagg tctgaccccc accactggcc caccgcttc taccacaagg actttgcctc      2040
tgaaggccag tggctacagg tggtagcagg tgggctgctc tcacccgtcc tgggctccct    2100
ccctccagcc tcccttctca gtccctaatt ggcctctccc accctcaccc cagcattgct    2160
tcatccataa gtgggtccct tgagggctga gcagaagacg gtcggcctct ggccctcaag    2220
ggaatctcac agctcagtgt gtgttcagcc ctagttgaat gttgtcaagg ctcttattga    2280
aggcaagacc ctctgacctt ataggcaacg gccaaatggg gtcatctgct tctttttccat    2340 ccccctaact acataccttaaatctctgaa ctctgacctc aggaggctct gggcatatga      2400
gccctatatg taccaagtgt acctagttgg ctgcctcccg ccactctgac taaaaggaat    2460
cttaagagtg tacatttgga ggtggaaaga ttgttcagtt taccctaaag actttgataa    2520
gaaagagaaa gaaagaaaga aagaaagaaa gaaagaaaga aagaaagaaa gaaaaaaaaa    2580
aaa                                                                   2583
```

<210> SEQ ID NO 5
<211> LENGTH: 660
<212> TYPE: PRT
<213> ORGANISM: Homo sapiens

<400> SEQUENCE: 5

```
Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Ala Pro Ser
            20                  25                  30

Pro Ile Ile Lys Phe Pro Gly Asp Val Ala Pro Lys Thr Asp Lys Glu
            35                  40                  45

Leu Ala Val Gln Tyr Leu Asn Thr Phe Tyr Gly Cys Pro Lys Glu Ser
50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
                100                 105                 110

Phe Pro Arg Lys Pro Lys Trp Asp Lys Asn Gln Ile Thr Tyr Arg Ile
                115                 120                 125

Ile Gly Tyr Thr Pro Asp Leu Asp Pro Glu Thr Val Asp Asp Ala Phe
            130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
                180                 185                 190

His Ala Phe Ala Pro Gly Thr Gly Val Gly Gly Asp Ser His Phe Asp
            195                 200                 205

Asp Asp Glu Leu Trp Thr Leu Gly Glu Gly Gln Val Val Arg Val Lys
            210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
                260                 265                 270

Phe Cys Pro His Glu Ala Leu Phe Thr Met Gly Gly Asn Ala Glu Gly
            275                 280                 285

Gln Pro Cys Lys Phe Pro Phe Arg Phe Gln Gly Thr Ser Tyr Asp Ser
            290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
                340                 345                 350

Phe Thr Phe Leu Gly Asn Lys Tyr Glu Ser Cys Thr Ser Ala Gly Arg
            355                 360                 365

Ser Asp Gly Lys Met Trp Cys Ala Thr Thr Ala Asn Tyr Asp Asp Asp
        370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
```

```
                420             425             430
Leu Ser Gln Asp Asp Ile Lys Gly Ile Gln Glu Leu Tyr Gly Ala Ser
        435                 440                 445
Pro Asp Ile Asp Leu Gly Thr Gly Pro Thr Pro Thr Leu Gly Pro Val
    450                 455                 460
Thr Pro Glu Ile Cys Lys Gln Asp Ile Val Phe Asp Gly Ile Ala Gln
465                 470                 475                 480
Ile Arg Gly Glu Ile Phe Phe Lys Asp Arg Phe Ile Trp Arg Thr
                485                 490                 495
Val Thr Pro Arg Asp Lys Pro Met Gly Pro Leu Leu Val Ala Thr Phe
        500                 505                 510
Trp Pro Glu Leu Pro Glu Lys Ile Asp Ala Val Tyr Glu Ala Pro Gln
        515                 520                 525
Glu Glu Lys Ala Val Phe Phe Ala Gly Asn Glu Tyr Trp Ile Tyr Ser
        530                 535                 540
Ala Ser Thr Leu Glu Arg Gly Tyr Pro Lys Pro Leu Thr Ser Leu Gly
545                 550                 555                 560
Leu Pro Pro Asp Val Gln Arg Val Asp Ala Ala Phe Asn Trp Ser Lys
                565                 570                 575
Asn Lys Lys Thr Tyr Ile Phe Ala Gly Asp Lys Phe Trp Arg Tyr Asn
        580                 585                 590
Glu Val Lys Lys Lys Met Asp Pro Gly Phe Pro Lys Leu Ile Ala Asp
        595                 600                 605
Ala Trp Asn Ala Ile Pro Asp Asn Leu Asp Ala Val Val Asp Leu Gln
    610                 615                 620
Gly Gly Gly His Ser Tyr Phe Phe Lys Gly Ala Tyr Tyr Leu Lys Leu
625                 630                 635                 640
Glu Asn Gln Ser Leu Lys Ser Val Lys Phe Gly Ser Ile Lys Ser Asp
                645                 650                 655
Trp Leu Gly Cys
            660

<210> SEQ ID NO 6
<211> LENGTH: 662
<212> TYPE: PRT
<213> ORGANISM: Mus musculus

<400> SEQUENCE: 6

Met Glu Ala Arg Val Ala Trp Gly Ala Leu Ala Gly Pro Leu Arg Val
1               5                   10                  15
Leu Cys Val Leu Cys Cys Leu Leu Gly Arg Ala Ile Ala Ala Pro Ser
            20                  25                  30
Pro Ile Ile Lys Phe Pro Gly Asp Val Ala Pro Lys Thr Asp Lys Glu
        35                  40                  45
Leu Ala Val Gln Tyr Leu Asn Thr Phe Tyr Gly Cys Pro Lys Glu Ser
    50                  55                  60
Cys Asn Leu Phe Val Leu Lys Asp Thr Leu Lys Lys Met Gln Lys Phe
65                  70                  75                  80
Phe Gly Leu Pro Gln Thr Gly Asp Leu Asp Gln Asn Thr Ile Glu Thr
                85                  90                  95
Met Arg Lys Pro Arg Cys Gly Asn Pro Asp Val Ala Asn Tyr Asn Phe
            100                 105                 110
Phe Pro Arg Lys Pro Lys Trp Asp Lys Asn Gln Ile Thr Tyr Arg Ile
        115                 120                 125
Ile Gly Tyr Thr Pro Asp Leu Asp Pro Glu Thr Val Asp Asp Ala Phe
```

-continued

```
                130                 135                 140
Ala Arg Ala Leu Lys Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
                180                 185                 190

His Ala Phe Ala Pro Gly Thr Gly Val Gly Gly Asp Ser His Phe Asp
                195                 200                 205

Asp Asp Glu Leu Trp Thr Leu Gly Glu Gly Gln Val Val Arg Val Lys
210                 215                 220

Tyr Gly Asn Ala Asp Gly Glu Tyr Cys Lys Phe Pro Phe Leu Phe Asn
225                 230                 235                 240

Gly Arg Glu Tyr Ser Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
                260                 265                 270

Phe Cys Pro His Glu Ala Leu Phe Thr Met Gly Gly Asn Ala Asp Gly
                275                 280                 285

Gln Pro Cys Lys Phe Pro Phe Arg Phe Gln Gly Thr Ser Tyr Asn Ser
                290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
                340                 345                 350

Phe Thr Phe Leu Gly Asn Lys Tyr Glu Ser Cys Thr Ser Ala Gly Arg
                355                 360                 365

Asn Asp Gly Lys Val Trp Cys Ala Thr Thr Asn Tyr Asp Asp Asp
                370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
                420                 425                 430

Leu Ser His Asp Asp Ile Lys Gly Ile Gln Glu Leu Tyr Gly Pro Ser
                435                 440                 445

Pro Asp Ala Asp Thr Asp Thr Gly Thr Gly Pro Thr Pro Thr Leu Gly
                450                 455                 460

Pro Val Thr Pro Glu Ile Cys Lys Gln Asp Ile Val Phe Asp Gly Ile
465                 470                 475                 480

Ala Gln Ile Arg Gly Glu Ile Phe Phe Phe Lys Asp Arg Phe Ile Trp
                485                 490                 495

Arg Thr Val Thr Pro Arg Asp Lys Pro Thr Gly Pro Leu Leu Val Ala
                500                 505                 510

Thr Phe Trp Pro Glu Leu Pro Glu Lys Ile Asp Ala Val Tyr Glu Ala
                515                 520                 525

Pro Gln Glu Glu Lys Ala Val Phe Phe Ala Gly Asn Glu Tyr Trp Val
                530                 535                 540

Tyr Ser Ala Ser Thr Leu Glu Arg Gly Tyr Pro Lys Pro Leu Thr Ser
545                 550                 555                 560
```

```
Leu Gly Leu Pro Pro Asp Val Gln Gln Val Asp Ala Ala Phe Asn Trp
            565                 570                 575

Ser Lys Asn Lys Lys Thr Tyr Ile Phe Ala Gly Asp Lys Phe Trp Arg
        580                 585                 590

Tyr Asn Glu Val Lys Lys Lys Met Asp Pro Gly Phe Pro Lys Leu Ile
    595                 600                 605

Ala Asp Ser Trp Asn Ala Ile Pro Asp Asn Leu Asp Ala Val Val Asp
610                 615                 620

Leu Gln Gly Gly His Ser Tyr Phe Phe Lys Gly Ala Tyr Tyr Leu
625                 630                 635                 640

Lys Leu Glu Asn Gln Ser Leu Lys Ser Val Lys Phe Gly Ser Ile Lys
            645                 650                 655

Ser Asp Trp Leu Gly Cys
            660

<210> SEQ ID NO 7
<211> LENGTH: 3546
<212> TYPE: DNA
<213> ORGANISM: Homo sapiens

<400> SEQUENCE: 7
```

| | | | | | |
|---|---|---|---|---|---|
| gcggctgccc | tcccttgttt | ccgctgcatc | cagacttcct | caggcggtgg | ctggaggctg | 60 |
| cgcatctggg | gctttaaaca | tacaaaggga | ttgccaggac | ctgcggcggc | ggcggcggcg | 120 |
| gcggggctg | gggcgcgggg | gccggaccat | gagccgctga | gccgggcaaa | ccccaggcca | 180 |
| ccgagccagc | ggaccctcgg | agcgcagccc | tgcgccgcgg | agcaggctcc | aaccaggcgg | 240 |
| cgaggcggcc | acacgcaccg | agccagcgac | ccccgggcga | cgcgcggggc | cagggagcgc | 300 |
| tacgatggag | gcgctaatgg | cccggggcgc | gctcacgggt | ccctgaggg | cgctctgtct | 360 |
| cctgggctgc | ctgctgagcc | acgccgccgc | cgcgccgtcg | cccatcatca | agttccccgg | 420 |
| cgatgtcgcc | cccaaaacgg | acaaagagtt | ggcagtgcaa | tacctgaaca | ccttctatgg | 480 |
| ctgccccaag | gagagctgca | acctgtttgt | gctgaaggac | acactaaaga | agatgcagaa | 540 |
| gttctttgga | ctgccccaga | caggtgatct | tgaccagaat | accatcgaga | ccatgcggaa | 600 |
| gccacgctgc | ggcaacccag | atgtggccaa | ctacaacttc | ttccctcgca | gcccaagtg | 660 |
| ggacaagaac | cagatcacat | acaggatcat | tggctacaca | cctgatctgg | acccagagac | 720 |
| agtggatgat | gcctttgctc | gtgccttcca | agtctggagc | gatgtgaccc | cactgcggtt | 780 |
| ttctcgaatc | catgatggag | aggcagacat | catgatcaac | tttggccgct | gggagcatgg | 840 |
| cgatggatac | cccttttgacg | gtaaggacgg | actcctggct | catgccttcg | ccccaggcac | 900 |
| tggtgttggg | ggagactccc | attttgatga | cgatgagcta | tggaccttgg | gagaaggcca | 960 |
| agtggtccgt | gtgaagtatg | gaacgccga | tggggagtac | tgcaagttcc | ccttcttgtt | 1020 |
| caatggcaag | gagtacaaca | gctgcactga | taccggccgc | agcgatggct | tcctctggtg | 1080 |
| ctccaccacc | tacaactttg | agaaggatgg | caagtacggc | ttctgtcccc | atgaagccct | 1140 |
| gttcaccatg | ggcggcaacg | ctgaaggaca | gccctgcaag | tttccattcc | gcttccaggg | 1200 |
| cacatcctat | gacagctgca | ccactgaggg | ccgcacggat | ggctaccgct | ggtgcggcac | 1260 |
| cactgaggac | tacgaccgcg | acaagaagta | tggcttctgc | cctgagaccg | ccatgtccac | 1320 |
| tgttggtggg | aactcagaag | gtgccccctg | tgtcttcccc | ttcactttcc | tgggcaacaa | 1380 |
| atatgagagc | tgcaccagcg | ccggccgcag | tgacggaaag | atgtggtgtg | cgaccacagc | 1440 |
| caactacgat | gatgaccgca | gtggggcttt | ctgccctgac | caagggtaca | gcctgttcct | 1500 |
| cgtggcagcc | cacgagtttg | ccacgccat | ggggctggag | cactcccaag | accctgggc | 1560 |

| | |
|---|---|
| cctgatggca cccatttaca cctacaccaa gaacttccgt ctgtcccagg atgacatcaa | 1620 |
| gggcattcag gagctctatg gggcctctcc tgacattgac cttggcaccg gccccacccc | 1680 |
| cacgctgggc cctgtcactc ctgagatctg caaacaggac attgtatttg atggcatcgc | 1740 |
| tcagatccgt ggtgagatct tcttcttcaa ggaccggttc atttggcgga ctgtgacgcc | 1800 |
| acgtgacaag cccatggggc ccctgctggt ggccacattc tggcctgagc tcccggaaaa | 1860 |
| gattgatgcg gtatacgagg ccccacagga ggagaaggct gtgttctttg cagggaatga | 1920 |
| atactggatc tactcagcca gcaccctgga gcgagggtac cccaagccac tgaccagcct | 1980 |
| gggactgccc cctgatgtcc agcgagtgga tgccgccttt aactggagca aaaacaagaa | 2040 |
| gacatacatc tttgctggag acaaattctg gagatacaat gaggtgaaga gaaaatgga | 2100 |
| tcctggcttc cccaagctca tcgcagatgc ctggaatgcc atccccgata acctggatgc | 2160 |
| cgtcgtggac ctgcagggcg gcggtcacag ctacttcttc aagggtgcct attacctgaa | 2220 |
| gctggagaac caaagtctga gagcgtgaa gtttggaagc atcaaatccg actggctagg | 2280 |
| ctgctgagct ggccctggct cccacaggcc cttcctctcc actgccttcg atacaccggg | 2340 |
| cctggagaac tagagaagga cccggagggg cctggcagcc gtgccttcag ctctacagct | 2400 |
| aatcagcatt ctcactccta cctggtaatt taagattcca gagagtggct cctcccggtg | 2460 |
| cccaagaata gatgctgact gtactcctcc caggcgcccc ttcccctcc aatcccacca | 2520 |
| accctcagag ccaccccta agagatactt tgatattttc aacgcagccc tgctttgggc | 2580 |
| tgccctggtg ctgccacact tcaggctctt ctcctttcac aaccttctgt ggctcacaga | 2640 |
| acccttggag ccaatggaga ctgtctcaag agggcactgg tggcccgaca gcctggcaca | 2700 |
| gggcagtggg acagggcatg gccaggtggc cactccagac ccctggcttt tcactgctgg | 2760 |
| ctgccttaga acctttctta cattagcagt ttgctttgta tgcactttgt ttttttcttt | 2820 |
| gggtcttgtt ttttttttcc acttagaaat tgcatttcct gacagaagga ctcaggttgt | 2880 |
| ctgaagtcac tgcacagtgc atctcagccc acatagtgat ggttcccctg ttcactctac | 2940 |
| ttagcatgtc cctaccgagt ctcttctcca ctggatggag gaaaaccaag ccgtggcttc | 3000 |
| ccgctcagcc ctccctgccc ctcccttcaa ccattcccca tgggaaatgt caacaagtat | 3060 |
| gaataaagac acctactgag tggccgtgtt tgccatctgt tttagcagag cctagacaag | 3120 |
| ggccacagac ccagccagaa gcggaaactt aaaaagtccg aatctctgct ccctgcaggg | 3180 |
| cacaggtgat ggtgtctgct ggaaaggtca gagcttccaa agtaaacagc aagagaacct | 3240 |
| cagggagagt aagctctagt ccctctgtcc tgtagaaaga gccctgaaga atcagcaatt | 3300 |
| ttgttgcttt attgtggcat ctgttcgagg tttgcttcct cttttaagtct gtttcttcat | 3360 |
| tagcaatcat atcagtttta atgctactac taacaatgaa cagtaacaat aatatccccc | 3420 |
| tcaattaata gagtgctttc tatgtgcaag gcacttttca cgtgtcacct atttttaacct | 3480 |
| ttccaaccac ataaataaaa aaggccatta ttagttgaat cttattgatg aagagaaaaa | 3540 |
| aaaaaa | 3546 |

<210> SEQ ID NO 8
<211> LENGTH: 3070
<212> TYPE: DNA
<213> ORGANISM: Mus musculus

<400> SEQUENCE: 8

| | |
|---|---|
| ccagccggcc acatctggcg tctgcccgcc cttgtttccg ctgcatccag acttccctgg | 60 |
| tggctggagg ctctgtgtgc atccaggagt ttagatatac aaagggattg ccaggacctg | 120 |

```
caagcacccg cggcagtggt gtgtattggg acgtgggacc ccgttatgag ctcctgagcc    180
ccgagaagca gaggcagtag agtaagggga tcgccgtgca gggcaggcgc cagccgggcg    240
gaccccaggg cacagccaga gacctcaggg tgacacgcgg agcccgggag cgcaacgatg    300
gaggcacgag tggcctgggg agcgctggcc ggacctctgc gggttctctg cgtcctgtgc    360
tgcctgttgg gccgcgccat cgctgcacca tcgcccatca tcaagttccc cggcgatgtc    420
gcccctaaaa cagacaaaga gttggcagtg caatacctga acactttcta tggctgcccc    480
aaggagagtt gcaacctctt tgtgctgaaa gataccctca agaagatgca gaagttcttt    540
gggctgcccc agacaggtga ccttgaccag aacaccatcg agaccatgcg gaagccaaga    600
tgtggcaacc cagatgtggc caactacaac ttcttccccc gcaagcccaa gtgggacaag    660
aaccagatca catacaggat cattggttac acacctgacc tggaccctga accgtggat     720 gatgcttttg ctcgggcctt aaaagtatgg agcgacgtca ctccgctgcg ctttctcga     780 atccatgatg gggaggctga catcatgatc aactttggac gctgggagca tggagatgga    840
tacccatttg atggcaagga tggactcctg gcacatgcct ttgccccggg cactggtgtt    900
gggggagatt ctcactttga tgatgatgag ctgtggaccc tgggagaagg acaagtggtc    960
cgcgtaaagt atgggaacgc tgatggcgag tactgcaagt tccccttcct gttcaacggt   1020
cgggaataca gcagctgtac agacactggt cgcagtgatg gcttcctctg gtgctccacc   1080
acatacaact ttgagaagga tggcaagtat ggcttctgcc ccatgaagc cttgtttacc    1140 atgggtggca atgcagatgg acagccctgc aagttcccgt tccgcttcca gggcacctcc   1200
tacaacagct gtaccaccga gggccgcacc gatggctacc gctggtgtgg caccaccgag   1260
gactatgacc gggataagaa gtatggattc tgtcccgaga ccgctatgtc cactgtgggt   1320
ggaaattcag aaggtgcccc atgtgtcttc cccttcactt tcctgggcaa caagtatgag   1380
agctgcacca cgcgccggcg caacgatggc aaggtgtggt gtgcgaccac aaccaactac   1440
gatgatgacc ggaagtgggg cttctgtcct gaccaaggat atagcctatt cctcgtggca   1500
gcccatgagt tcggccatgc catggggctg aacactctc aggaccctgg agctctgatg    1560
gccccgatct acacctacac aagaacttc gattatcccc atgatgacat caaggggatc   1620
caggagctct atgggccctc ccccgatgct gatactgaca ctggtactgg ccccacacca   1680
acactgggac ctgtcactcc ggagatctgc aaacaggaca ttgtctttga tggcatcgct   1740
cagatccgtg gtgagatctt cttcttcaag gaccggttta tttggcggac agtgacacca   1800
cgtgacaagc ccacaggtcc cttgctggtg gccacattct ggcctgagct cccagaaaag   1860
attgacgctg tgtatgaggc cccacaggag gagaaggctg tgttcttcgc agggaatgag   1920
tactgggtct attctgctag tactctggag cgaggatacc ccaagccact gaccagcctg   1980
gggttgcccc ctgatgtcca gcaagtagat gctgcccttta actggagtaa gaacaagaag   2040
acatacatct ttgcaggaga caagttctgg agatacaatg aagtgaagaa gaaaatggac   2100
cccggttccc ctaagctcat cgcagactcc tggaatgcca tccctgataa cctggatgcc   2160
gtcgtggacc tgcagggtgg tggtcatagc tacttcttca aggggctta ttacctgaag   2220 ctggagaacc aaaagtctca gagcgtgaag tttggaagca tcaaatcaga ctggctgggc   2280
tgctgagctg gccctgttcc cacgggccct atcatcttca tcgctgcaca ccaggtgaag   2340
gatgtgaagc agcctggcgg ctctgtcctc ctctgtagtt aaccagcctt ctccttcacc   2400
tggtgacttc agatttaaga gggtggcttc ttttgtgcc caaagaaagg tgctgactgt    2460
accctcccgg gtgctgcttc tccttcctgc ccacccctagg ggatgcttgg atatttgcaa   2520
```

-continued

```
tgcagccctc ctctgggctg ccctggtgct ccactcttct ggttcttcaa catctatgac      2580 cttttatgg  ctttcagcac tctcagagtt aatagagact ggcttaggag ggcactggtg      2640
gccctgttaa cagcctggca tggggcagtg gggtacaggt gtgccaaggt ggaaatcaga      2700
gacacctggt ttcacccttt ctgctgccca gacacctgca ccaccttaac tgttgctttt      2760
gtatgccctt cgctcgtttc cttcaacctt ttcagttttc cactccactg catttcctgc      2820
ccaaaggact cgggttgtct gacatcgctg catgatgcat ctcagcccgc ctagtgatgg      2880
ttcccctcct cactctgtgc agatcatgcc cagtcacttc ctccactgga tggaggagaa      2940
ccaagtcagt ggcttcctgc tcagcctcct tgcttctccc tttaacagtt ccccatggga      3000
aatggcaaac aagtataaat aaagacaccc attgagtgac aaaaaaaaaa aaaaaaaaa       3060 aaaaaaaaa                                                              3070
```

<210> SEQ ID NO 9
<211> LENGTH: 707
<212> TYPE: PRT
<213> ORGANISM: Homo sapiens

<400> SEQUENCE: 9

```
Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270
```

```
Ser Glu Arg Leu Tyr Thr Gln Asp Gly Asn Ala Asp Gly Lys Pro Cys
    275                 280                 285

Gln Phe Pro Phe Ile Phe Gln Gly Gln Ser Tyr Ser Ala Cys Thr Thr
290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
                340                 345                 350

Phe Leu Gly Lys Glu Tyr Ser Thr Cys Thr Ser Glu Gly Arg Gly Asp
            355                 360                 365

Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
                420                 425                 430

Lys Asp Asp Val Asn Gly Ile Arg His Leu Tyr Gly Pro Arg Pro Glu
            435                 440                 445

Pro Glu Pro Arg Pro Pro Thr Thr Thr Pro Gln Pro Thr Ala Pro
    450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
    530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
            595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
            675                 680                 685

Asn Gln Val Asp Gln Val Gly Tyr Val Thr Tyr Asp Ile Leu Gln Cys
    690                 695                 700
```

```
Pro Glu Asp
705

<210> SEQ ID NO 10
<211> LENGTH: 730
<212> TYPE: PRT
<213> ORGANISM: Mus musculus

<400> SEQUENCE: 10

Met Ser Pro Trp Gln Pro Leu Leu Ala Leu Leu Ala Phe Gly Cys
 1               5                  10                  15

Ser Ser Ala Ala Pro Tyr Gln Arg Gln Pro Thr Phe Val Val Phe Pro
            20                  25                  30

Lys Asp Leu Lys Thr Ser Asn Leu Thr Asp Thr Gln Leu Ala Glu Ala
                35                  40                  45

Tyr Leu Tyr Arg Tyr Gly Tyr Thr Arg Ala Ala Gln Met Met Gly Glu
    50                  55                  60

Lys Gln Ser Leu Arg Pro Ala Leu Leu Met Leu Gln Lys Gln Leu Ser
65                  70                  75                  80

Leu Pro Gln Thr Gly Glu Leu Asp Ser Gln Thr Leu Lys Ala Ile Arg
                85                  90                  95

Thr Pro Arg Cys Gly Val Pro Asp Val Gly Arg Phe Gln Thr Phe Lys
                100                 105                 110

Gly Leu Lys Trp Asp His His Asn Ile Thr Tyr Trp Ile Gln Asn Tyr
            115                 120                 125

Ser Glu Asp Leu Pro Arg Asp Met Ile Asp Ala Phe Ala Arg Ala
130                 135                 140

Phe Ala Val Trp Gly Glu Val Ala Pro Leu Thr Phe Thr Arg Val Tyr
145                 150                 155                 160

Gly Pro Glu Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Ala Gly Val Gln Gly Asp Ala His Phe Asp Asp Glu
            195                 200                 205

Leu Trp Ser Leu Gly Lys Gly Val Val Ile Pro Thr Tyr Tyr Gly Asn
210                 215                 220

Ser Asn Gly Ala Pro Cys His Phe Pro Phe Thr Phe Glu Gly Arg Ser
225                 230                 235                 240

Tyr Ser Ala Cys Thr Thr Asp Gly Arg Asn Asp Gly Thr Pro Trp Cys
                245                 250                 255

Ser Thr Thr Ala Asp Tyr Asp Lys Asp Gly Lys Phe Gly Phe Cys Pro
            260                 265                 270

Ser Glu Arg Leu Tyr Thr Glu His Gly Asn Gly Glu Gly Lys Pro Cys
        275                 280                 285

Val Phe Pro Phe Ile Phe Glu Gly Arg Ser Tyr Ser Ala Cys Thr Thr
    290                 295                 300

Lys Gly Arg Ser Asp Gly Tyr Arg Trp Cys Ala Thr Ala Asn Tyr
305                 310                 315                 320

Asp Gln Asp Lys Leu Tyr Gly Phe Cys Pro Thr Arg Val Asp Ala Thr
                325                 330                 335

Val Val Gly Gly Asn Ser Ala Gly Glu Leu Cys Val Phe Pro Phe Val
            340                 345                 350

Phe Leu Gly Lys Gln Tyr Ser Ser Cys Thr Ser Asp Gly Arg Arg Asp
        355                 360                 365
```

Gly Arg Leu Trp Cys Ala Thr Thr Ser Asn Phe Asp Thr Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
            405                 410                 415

Ala Leu Met Tyr Pro Leu Tyr Ser Tyr Leu Glu Gly Phe Pro Leu Asn
            420                 425                 430

Lys Asp Asp Ile Asp Gly Ile Gln Tyr Leu Tyr Gly Arg Gly Ser Lys
            435                 440                 445

Pro Asp Pro Arg Pro Pro Ala Thr Thr Thr Thr Glu Pro Gln Pro Thr
    450                 455                 460

Ala Pro Pro Thr Met Cys Pro Thr Ile Pro Pro Thr Ala Tyr Pro Thr
465                 470                 475                 480

Val Gly Pro Thr Val Gly Pro Thr Gly Ala Pro Ser Pro Gly Pro Thr
            485                 490                 495

Ser Ser Pro Ser Pro Gly Pro Thr Gly Ala Pro Ser Pro Gly Pro Thr
            500                 505                 510

Ala Pro Pro Thr Ala Gly Ser Ser Glu Ala Ser Thr Glu Ser Leu Ser
            515                 520                 525

Pro Ala Asp Asn Pro Cys Asn Val Asp Val Phe Asp Ala Ile Ala Glu
    530                 535                 540

Ile Gln Gly Ala Leu His Phe Phe Lys Asp Gly Trp Tyr Trp Lys Phe
545                 550                 555                 560

Leu Asn His Arg Gly Ser Pro Leu Gln Gly Pro Phe Leu Thr Ala Arg
            565                 570                 575

Thr Trp Pro Ala Leu Pro Ala Thr Leu Asp Ser Ala Phe Glu Asp Pro
            580                 585                 590

Gln Thr Lys Arg Val Phe Phe Ser Gly Arg Gln Met Trp Val Tyr
    595                 600                 605

Thr Gly Lys Thr Val Leu Gly Pro Arg Ser Leu Asp Lys Leu Gly Leu
    610                 615                 620

Gly Pro Glu Val Thr His Val Ser Gly Leu Leu Pro Arg Arg Leu Gly
625                 630                 635                 640

Lys Ala Leu Leu Phe Ser Lys Gly Arg Val Trp Arg Phe Asp Leu Lys
            645                 650                 655

Ser Gln Lys Val Asp Pro Gln Ser Val Ile Arg Val Asp Lys Glu Phe
            660                 665                 670

Ser Gly Val Pro Trp Asn Ser His Asp Ile Phe Gln Tyr Gln Asp Lys
            675                 680                 685

Ala Tyr Phe Cys His Gly Lys Phe Phe Trp Arg Val Ser Phe Gln Asn
            690                 695                 700

Glu Val Asn Lys Val Asp His Glu Val Asn Gln Val Asp Asp Val Gly
705                 710                 715                 720

Tyr Val Thr Tyr Asp Leu Leu Gln Cys Pro
            725                 730

<210> SEQ ID NO 11
<211> LENGTH: 2387
<212> TYPE: DNA
<213> ORGANISM: Homo sapiens

<400> SEQUENCE: 11
agacacctct gccctcacca tgagcctctg gcagccccctg gtcctggtgc tcctggtgct    60

```
gggctgctgc tttgctgccc ccagacagcg ccagtccacc cttgtgctct tccctggaga    120
cctgagaacc aatctcaccg acaggcagct ggcagaggaa tacctgtacc gctatggtta    180
cactcgggtg gcagagatgc gtggagagtc gaaatctctg gggcctgcgc tgctgcttct    240
ccagaagcaa ctgtccctgc ccgagaccgg tgagctggat agcgccacgc tgaaggccat    300
gcgaacccca cggtgcgggg tcccagacct gggcagattc caaacctttg agggcgacct    360
caagtggcac caccacaaca tcacctattg gatccaaaac tactcggaag acttgccgcg    420
ggcggtgatt gacgacgcct tgcccgcgc cttcgcactg tggagcgcgg tgacgccgct    480
caccttcact cgcgtgtaca gccgggacgc agacatcgtc atccagtttg gtgtcgcgga    540
gcacggagac gggtatccct tcgacgggaa ggacgggctc ctggcacacg cctttcctcc    600
tggccccggc attcagggag acgcccattt cgacgatgac gagttgtggt ccctgggcaa    660
gggcgtcgtg gttccaactc ggtttggaaa cgcagatggc gcggcctgcc acttcccctt    720
catcttcgag ggccgctcct actctgcctg caccaccgac ggtcgctccg acggcttgcc    780
ctggtgcagt accacggcca actacgacac cgacgaccgg tttggcttct gccccagcga    840
gagactctac acccaggacg gcaatgctga tgggaaaccc tgccagtttc cattcatctt    900
ccaaggccaa tcctactccg cctgcaccac ggacggtcgc tccgacggct accgctggtg    960
cgccaccacc gccaactacg accgggacaa gctcttcggc ttctgcccga cccgagctga   1020
ctcgacggtg atggggggca actcggcggg ggagctgtgc gtcttcccct tcactttcct   1080
gggtaaggag tactcgacct gtaccagcga gggccgcgga gatgggcgcc tctggtgcgc   1140
taccacctcg aactttgaca gcgacaagaa gtggggcttc tgcccggacc aaggatacag   1200
tttgttcctc gtggcggcgc atgagttcgg ccacgcgctg gcttagatc attcctcagt   1260
gccggaggcg ctcatgtacc ctatgtaccg cttcactgag gggccccct tgcataagga   1320
cgacgtgaat ggcatccggc acctctatgg tcctcgccct gaacctgagc cacggcctcc   1380
aaccaccacc acaccgcagc ccacggctcc ccgacggtc tgccccaccg acccccccac   1440
tgtccacccc tcagagcgcc ccacagctgg ccccacaggt ccccctcag ctggccccac   1500
aggtcccccc actgctggcc cttctacggc cactactgtg cctttgagtc cggtggacga   1560
tgcctgcaac gtgaacatct tcgacgccat cgcggagatt gggaaccagc tgtatttgtt   1620
caaggatggg aagtactggc gattctctga gggcaggggg agccggccgc agggcccctt   1680
ccttatcgcc gacaagtggc ccgcgctgcc ccgcaagctg gactcggtct tgaggagcg   1740
gctctccaag aagcttttct tcttctctgg gcgccaggtg tgggtgtaca caggcgcgtc   1800
ggtgctgggc ccgaggcgtc tggacaagct gggcctggga gccgacgtgg cccaggtgac   1860
cggggccctc cggagtggca gggggaagat gctgctgttc agcgggcggc gcctctggag   1920
gttcgacgtg aaggcgcaga tggtggatcc ccggagcgcc agcgaggtgg accggatgtt   1980
ccccgggggtg ccttttggaca cgcacgacgt cttccagtac cgagagaaag cctatttctg   2040
ccaggaccgc ttctactggc gcgtgagttc ccggagtgag ttgaaccagg tggaccaagt   2100
gggctacgtg acctatgaca tcctgcagtg ccctgaggac tagggctccc gtcctgcttt   2160
ggcagtgcca tgtaaatccc cactgggacc aaccctgggg aaggagccag tttgccggat   2220
acaaactggt attctgttct ggaggaaagg gaggagtgga ggtgggctgg gccctctctt   2280
ctcacctttg ttttttgttg gagtgtttct aataaacttg gattctctaa cctttaaaaa   2340
aaaaaaaaaa aaaaaaaaaa aaaaaaaaaa aaaaaaaaaa aaaaaaa                 2387

<210> SEQ ID NO 12
```

<211> LENGTH: 3185
<212> TYPE: DNA
<213> ORGANISM: Mus musculus

<400> SEQUENCE: 12

```
ctcaccatga gtccctggca gcccctgctc ctggctctcc tggctttcgg ctgcagctct      60
gctgcccctt accagcgcca gccgactttt gtggtcttcc ccaaagacct gaaaacctcc     120
aacctcacgg acacccagct ggcagaggca tacttgtacc gctatggtta cacccgggcc     180
gcccagatga tgggagagaa gcagtctcta cggccggctt tgctgatgct tcagaagcag     240
ctctccctgc cccagactgg tgagctggac agccagacac taaaggccat tcgaacacca     300
cgctgtggtg tcccagacgt gggtcgattc caaaccttca aaggcctcaa gtgggaccat     360
cataacatca catactggat ccaaaactac tctgaagact gccgcgaga catgatcgat      420
gacgccttcg cgcgcgcctt cgcggtgtgg ggcgaggtgg cacccctcac cttcacccgc     480
gtgtacggac ccgaagcgga cattgtcatc cagtttggtg tcgcggagca cggagacggg     540
tatcccttcg acggcaagga cggccttctg gcacacgcct ttcccctgg cgccggcgtt      600
cagggagatg cccatttcga cgacgacgag ttgtggtcgc tggcaaagg cgtcgtgatc      660
cccacttact atggaaactc aaatggtgcc ccatgtcact ttcccttcac cttcgaggga     720
cgctcctatt cggcctgcac cacagacggc cgcaacgacg gcacgccttg gtgtagcaca     780
acagctgact acgataagga cggcaaattt ggtttctgcc ctagtgagag actctacacg     840
gagcacggca acgagaagg caaaccctgt gtgttcccgt tcatctttga gggccgctcc     900
tactctgcct gcaccactaa aggccgctcg gatggttacc gctggtgcgc caccacagcc     960
aactatgacc aggataaact gtatggcttc tgccctaccc gagtggacgc gaccgtagtt    1020
ggggcaact cggcaggaga gctgtgcgtc ttccccttcg tcttcctggg caagcagtac     1080
tcttcctgta ccagcgacgg ccgcagggat gggcgcctct ggtgtgcgac acatcgaac    1140
ttcgacactg acaagaagtg gggtttctgt ccagaccaag ggtacagcct gttcctggtg     1200
gcagcgcacg agttcggcca tgcactgggc ttagatcatt ccagcgtgcc ggaagcgctc    1260
atgtacccgc tgtatagcta cctcgagggc ttccctctga taaagacga catagacgg     1320
atccagtatc tgtatggtcg tggctctaag cctgacccaa ggcctccagc caccaccaca    1380
actgaaccac agccgacagc acctcccact atgtgtccca ctatacctcc cacggcctat    1440
cccacagtgg gccccacggt tggccctaca ggcgccccct cacctggccc cacaagcagc    1500
ccgtcacctg gcctacagg cgcccctca cctggcccta cagcgcccc tactgcgggc      1560
tcttctgagg cctctacaga gtctttgagt ccggcagaca atccttgcaa tgtggatgtt    1620
tttgatgcta ttgctgagat ccagggcgct ctgcatttct tcaaggacgg ttggtactgg    1680
aagttcctga atcatagagg aagcccatta cagggcccct tccttactgc ccgcacgtgg    1740
ccagccctgc ctgcaacgct ggactccgcc tttgaggatc cgcagaccaa gagggttttc    1800
ttcttctctg gacgtcaaat gtgggtgtac acaggcaaga ccgtgctggg ccccaggagt    1860
ctggataagt tgggtctagg cccagaggta acccacgtca gcgggcttct cccgcgtcgt    1920
ctcgggaagg ctctgctgtt cagcaagggg cgtgtctgga gattcgactt gaagtctcag    1980
aaggtggatc cccagagcgt cattcgcgtg gataaggagt ctctggtgt gccctggaac    2040
tcacacgaca tcttccagta ccaagacaaa gcctatttct gccatggcaa attcttctgg    2100
cgtgtgagtt tccaaaatga ggtgaacaag gtggaccatg aggtgaacca ggtggacgac    2160
gtgggctacg tgacctacga cctcctgcag tgcccttgaa ctagggctcc ttctttgctt    2220
```

```
caaccgtgca gtgcaagtct ctagagacca ccaccaccac caccacacac aaacccatc    2280 cgagggaaag gtgctagctg gccaggtaca gactggtgat ctcttctaga gactgggaag    2340
gagtggaggc aggcagggct ctctctgccc accgtccttt cttgttggac tgtttctaat    2400
aaacacggat ccccaacctt ttccagctac tttagtcaat cagcttatct gtagttgcag    2460
atgcatccga gcaagaagac aactttgtag ggtggattct gaccttttat ttttgtgtgg    2520
cgtctgagaa ttgaatcagc tggcttttgt gacaggcact tcaccggcta aaccacctct    2580
cccgactcca gccctttttat ttattatgta tgaggttatg ttcacatgca tgtatttaac    2640
ccacagaatg cttactgtgt gtcgggcgcg gctccaaccg ctgcataaat attaaggtat    2700
tcagttgccc ctactggaag gtattatgta actatttctc tcttacattg gagaacacca    2760
ccgagctatc cactcatcaa acatttattg agagcatccc tagggagcca ggctctctac    2820
tgggcgttag ggacagaaat gttggttctt ccttcaagga ttgctcagag attctccgtg    2880
tcctgtaaat ctgctgaaac cagaccccag actcctctct ctcccgagag tccaactcac    2940
tcactgtggt tgctggcagc tgcagcatgc gtatacagca tgtgtgctag agaggtagag    3000
ggggtctgtg cgttatggtt caggtcgac tgtgtcctcc aggtgagatg acccctcagc    3060
tggaactgat ccaggaagga taaccaagtg tcttcctggc agtctttttt aaataaatga    3120
ataaatgaat atttacttaa aaaaaaaaaa aaaaaaaaaa aaaaaaaaaa aaaaaaaaaa    3180
aaaaa                                                                 3185

<210> SEQ ID NO 13
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Ser Met Asn Trp Val Arg Gln Ala Pro Gly Lys Gly Leu Glu Trp Val
        35                  40                  45

Ser Ser Ile Tyr Ser Ser Gly Ser Thr Leu Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Phe Asp Ile Trp Gly Gln Gly Thr Met Val Thr
            100                 105                 110

Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Asp Ile Gln Met Thr Gln Ser Pro Ser Ser Leu Ser Ala Phe Val Gly
1               5                   10                  15

Asp Lys Val Thr Ile Thr Cys Arg Ala Ser Gln Ser Val Gly Thr Tyr
            20                  25                  30

Leu Asn Trp Tyr Gln Gln Lys Ala Gly Lys Ala Pro Glu Leu Leu Ile
        35                  40                  45

Tyr Ala Thr Ser Asn Leu Arg Ser Gly Val Pro Ser Arg Phe Ser Gly
50                  55                  60

Ser Gly Ser Gly Thr Asp Phe Thr Leu Thr Ile Asn Thr Leu Gln Pro
65                  70                  75                  80

Glu Asp Phe Ala Thr Tyr Tyr Cys Gln Gln Ser Tyr Ser Ile Pro Arg
                85                  90                  95

Phe Thr Phe Gly Pro Gly Thr Lys Val Asp Ile Lys
            100                 105
```

<210> SEQ ID NO 15
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Ser Met Asn Trp Val Arg Gln Ala Pro Gly Lys Gly Leu Glu Trp Val
        35                  40                  45

Ser Ser Ile Tyr Ser Ser Gly Gly Ser Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Phe Asp Ile Trp Gly Gln Gly Thr Met Val Thr
            100                 105                 110

Val Ser Ser
        115
```

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Thr Tyr
            20                  25                  30

Leu Asn Trp Tyr Gln Gln Lys Pro Gly Lys Ala Pro Lys Leu Leu Ile
        35                  40                  45

Tyr Ala Thr Ser Asn Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Ser Ile Pro Arg
                    85                  90                  95
Phe Thr Phe Gly Pro Gly Thr Lys Val Asp Ile Lys
                100                 105

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Val Tyr
                20                  25                  30
Gly Met Val Trp Val Arg Gln Ala Pro Gly Lys Gly Leu Glu Trp Val
            35                  40                  45
Ser Val Ile Ser Ser Gly Gly Ser Thr Trp Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Leu Tyr Tyr Cys
                85                  90                  95
Ala Arg Pro Phe Ser Arg Arg Tyr Gly Val Phe Asp Tyr Trp Gly Gln
                100                 105                 110
Gly Thr Leu Val Thr Val Ser Ser
            115                 120

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Phe
                20                  25                  30
Leu Ala Trp Tyr Gln Gln Lys Pro Gly Lys Val Pro Lys Leu Leu Val
            35                  40                  45
Phe Gly Ala Ser Ala Leu Gln Ser Gly Val Pro Ser Arg Phe Ser Gly
        50                  55                  60
Ser Gly Ser Gly Thr Asp Phe Thr Leu Thr Ile Ser Gly Leu Gln Pro
65                  70                  75                  80
Glu Asp Val Ala Thr Tyr Tyr Cys Gln Lys Tyr Asn Gly Val Pro Leu
                85                  90                  95
Thr Phe Gly Gly Gly Thr Lys Val Glu Ile Lys
                100                 105

<210> SEQ ID NO 19
<211> LENGTH: 120
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Gly Met Val Trp Val Arg Gln Ala Pro Gly Lys Gly Leu Glu Trp Val
        35                  40                  45

Ser Val Ile Ser Ser Gly Gly Ser Thr Trp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Phe Ser Arg Arg Tyr Gly Val Phe Asp Tyr Trp Gly Gln
            100                 105                 110

Gly Thr Leu Val Thr Val Ser Ser
        115                 120

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Phe
            20                  25                  30

Leu Ala Trp Tyr Gln Gln Lys Pro Gly Lys Val Pro Lys Leu Leu Ile
        35                  40                  45

Tyr Gly Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Gly Val Pro Leu
                85                  90                  95

Thr Phe Gly Gly Gly Thr Lys Val Glu Ile Lys
            100                 105

<210> SEQ ID NO 21
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Phe Tyr Ser His Ser Ala Gln Ser Glu Leu Thr Gln Pro Pro Ser Ala
1               5                   10                  15

Ser Ala Ala Pro Gly Gln Arg Val Thr Ile Ser Cys Ser Gly Ser Ser
            20                  25                  30

Ser Asn Ile Gly Ser Asn Thr Val Thr Trp Tyr Gln Lys Leu Pro Gly
```

```
                35                  40                  45
Thr Ala Pro Lys Leu Leu Ile Tyr Asn Asn Tyr Glu Arg Pro Ser Gly
 50                  55                  60

Val Pro Ala Arg Phe Ser Gly Ser Lys Ser Gly Thr Ser Ala Ser Leu
 65                  70                  75                  80

Ala Ile Ser Gly Leu Gln Ser Glu Asp Glu Ala Asp Tyr Tyr Cys Ala
                 85                  90                  95

Thr Trp Asp Asp Ser Leu Ile Ala Asn Tyr Val Phe Gly Ser Gly Thr
            100                 105                 110

Lys Val Thr Val Leu Gly Gln Pro Lys Ala Asn Pro
        115                 120

<210> SEQ ID NO 22
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Lys Lys Leu Leu Phe Ala Ile Pro Leu Val Val Pro Phe Val Ala
 1               5                  10                  15

Gln Pro Ala Met Ala Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Pro Tyr Leu Met Asn Trp Val Arg Gln Ala Pro Gly Lys
 50                  55                  60

Gly Leu Glu Trp Val Ser Ser Ile Tyr Ser Ser Gly Gly Gly Thr Gly
 65                  70                  75                  80

Tyr Ala Asp Ser Val Lys Gly Arg Phe Thr Ile Ser Arg Asp Asn Ser
                 85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ile Tyr His Ser Ser Ser Gly Pro Phe
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Ser Ser Lys
145                 150                 155                 160

Ser

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Gly Thr Ser Ser Asp Val Gly Gly Tyr Asn Tyr Val Ser
 1               5                  10

<210> SEQ ID NO 24
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 24

Asp Val Ser Lys Arg Pro Ser
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Ser Tyr Ala Gly Ser Tyr Thr Leu Val
1               5                   10

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Tyr Gln Met Val
1               5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Ile Tyr Pro Ser Gly Gly Pro Thr Val Tyr Ala Asp Ser Val Lys
1               5                   10                  15

Gly

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Glu Asp Tyr Tyr Asp Ser Ser Gly Pro Gly Ala Phe Asp Ile
1               5                   10                  15

<210> SEQ ID NO 29
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ser Ala Leu Thr Gln Pro Arg Ser Val Ser Gly Ser Pro Gly Gln
1               5                   10                  15

```
Ser Val Thr Ile Ser Cys Thr Gly Thr Ser Ser Asp Val Gly Gly Tyr
         20                  25                  30

Asn Tyr Val Ser Trp Tyr Gln Gln His Pro Gly Lys Ala Pro Lys Leu
             35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Thr Leu Val Phe Gly Gly Gly Thr Lys Leu Thr Val Leu
            100                 105                 110

<210> SEQ ID NO 30
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 31
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Tyr Glu Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
             35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Thr Leu Val Phe Gly Gly Gly Thr Lys Leu Thr Val Leu
```

<210> SEQ ID NO 32
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
        115                 120

<210> SEQ ID NO 33
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Tyr Glu Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu
            100                 105                 110

<210> SEQ ID NO 34
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

-continued

<400> SEQUENCE: 34

```
cag tac gaa ttg act cag cct cgc tca gtg tcc ggg tct cct gga cag      48
Gln Tyr Glu Leu Thr Gln Pro Arg Ser Val Ser Gly Ser Pro Gly Gln
1               5                   10                  15 tca gtc acc atc tcc tgc act gga acc agc agt gat gtt ggt ggt tat      96
Ser Val Thr Ile Ser Cys Thr Gly Thr Ser Ser Asp Val Gly Gly Tyr
                20                  25                  30 aac tat gtc tcc tgg tac caa cag cac cca ggc aaa gcc ccc aaa ctc     144
Asn Tyr Val Ser Trp Tyr Gln Gln His Pro Gly Lys Ala Pro Lys Leu
            35                  40                  45 atg att tat gat gtc agt aag cgg ccc tca ggg gtc cct gat cgc ttc     192
Met Ile Tyr Asp Val Ser Lys Arg Pro Ser Gly Val Pro Asp Arg Phe
        50                  55                  60 tct ggc tcc aag tct ggc aac acg gcc tcc ctg acc atc tct ggg ctc     240
Ser Gly Ser Lys Ser Gly Asn Thr Ala Ser Leu Thr Ile Ser Gly Leu
65                  70                  75                  80 cag gct gag gat gag gct gat tat tac tgc tgc tca tat gca ggc agc     288
Gln Ala Glu Asp Glu Ala Asp Tyr Tyr Cys Cys Ser Tyr Ala Gly Ser
                85                  90                  95 tac act ttg gtg ttc ggc gga ggg acc aag ctg acc gtc cta              330
Tyr Thr Leu Val Phe Gly Gly Gly Thr Lys Leu Thr Val Leu
            100                 105                 110
```

<210> SEQ ID NO 35
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Gln Met Val Trp Val Arg Gln Ala Pro Gly Lys Gly Leu Glu Trp Val
            35                  40                  45

Ser Val Ile Tyr Pro Ser Gly Gly Pro Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
        115                 120
```

<210> SEQ ID NO 36
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(372)

<400> SEQUENCE: 36

```
gaa gtt caa ttg tta gag tct ggt ggc ggt ctt gtt cag cct ggt ggt    48
Glu Val Gln Leu Leu Glu Ser Gly Gly Gly Leu Val Gln Pro Gly Gly
1               5                   10                  15 tct tta cgt ctt tct tgc gct gct tcc gga ttc act ttc tct act tac    96
Ser Leu Arg Leu Ser Cys Ala Ala Ser Gly Phe Thr Phe Ser Thr Tyr
            20                  25                  30 cag atg gtt tgg gtt cgc caa gct cct ggt aaa ggt ttg gag tgg gtt   144
Gln Met Val Trp Val Arg Gln Ala Pro Gly Lys Gly Leu Glu Trp Val
        35                  40                  45 tct gtt atc tat cct tct ggt ggc cct act gtt tat gct gac tcc gtt   192
Ser Val Ile Tyr Pro Ser Gly Gly Pro Thr Val Tyr Ala Asp Ser Val
    50                  55                  60 aaa ggt cgc ttc act atc tct aga gac aac tct aag aat act ctc tac   240
Lys Gly Arg Phe Thr Ile Ser Arg Asp Asn Ser Lys Asn Thr Leu Tyr
65                  70                  75                  80 ttg cag atg aac agc tta agg gct gag gac acg gcc gtg tat tac tgt   288
Leu Gln Met Asn Ser Leu Arg Ala Glu Asp Thr Ala Val Tyr Tyr Cys
                85                  90                  95 gcg aga ggg gag gac tac tat gat agt agt ggc ccg ggg gct ttt gat   336
Ala Arg Gly Glu Asp Tyr Tyr Asp Ser Ser Gly Pro Gly Ala Phe Asp
            100                 105                 110 atc tgg ggc caa ggg aca atg gtc acc gtc tca agc                   372
Ile Trp Gly Gln Gly Thr Met Val Thr Val Ser Ser
        115                 120
```

```
<210> SEQ ID NO 37
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37
```

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Thr Lys Leu Thr Val Leu
            100                 105                 110
```

```
<210> SEQ ID NO 38
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

```
Gln Met Val Trp Val Arg Gln Ala Pro Gly Lys Gly Leu Glu Trp Val
            35                  40                  45

Ser Val Ile Tyr Pro Ser Gly Pro Thr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
            115                 120

<210> SEQ ID NO 39
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

<400> SEQUENCE: 39 cag agc gcc ctg acc cag ccc aga agc gtg tcc ggc agc cca ggc cag      48
Gln Ser Ala Leu Thr Gln Pro Arg Ser Val Ser Gly Ser Pro Gly Gln
1               5                   10                  15 agc gtg acc atc agc tgc acc ggc acc agc agc gac gtg ggc ggc tac      96
Ser Val Thr Ile Ser Cys Thr Gly Thr Ser Ser Asp Val Gly Gly Tyr
            20                  25                  30 aac tac gtg tcc tgg tat cag cag cac ccc ggc aag gcc ccc aag ctg     144
Asn Tyr Val Ser Trp Tyr Gln Gln His Pro Gly Lys Ala Pro Lys Leu
        35                  40                  45 atg atc tac gac gtg tcc aag agg ccc agc ggc gtg ccc gac agg ttc     192
Met Ile Tyr Asp Val Ser Lys Arg Pro Ser Gly Val Pro Asp Arg Phe
    50                  55                  60 agc ggc agc aag agc ggc aac acc gcc agc ctg acc atc tcc gga ctg     240
Ser Gly Ser Lys Ser Gly Asn Thr Ala Ser Leu Thr Ile Ser Gly Leu
65                  70                  75                  80 cag gcc gag gac gag gcc gac tac tac tgc tgc agc tac gcc ggc agc     288
Gln Ala Glu Asp Glu Ala Asp Tyr Tyr Cys Cys Ser Tyr Ala Gly Ser
                85                  90                  95 tac acc ctg gtg ttc ggc gga ggg acc aag ctg acc gtg ctg             330
Tyr Thr Leu Val Phe Gly Gly Gly Thr Lys Leu Thr Val Leu
            100                 105                 110

<210> SEQ ID NO 40
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

```
Met Ile Tyr Asp Val Ser Lys Arg Pro Ser Gly Val Pro Asp Arg Phe
        50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
             85                  90                  95

Tyr Thr Leu Val Phe Gly Gly Gly Thr Lys Leu Thr Val Leu
            100                 105                 110

<210> SEQ ID NO 41
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(372)

<400> SEQUENCE: 41 gag gtg caa ttg ctg gaa agc ggc gga gga ctg gtg cag cca ggc ggc        48
Glu Val Gln Leu Leu Glu Ser Gly Gly Gly Leu Val Gln Pro Gly Gly
  1               5                  10                  15 agc ctg agg ctg tcc tgc gcc gcc agc ggc ttc acc ttc agc acc tac        96
Ser Leu Arg Leu Ser Cys Ala Ala Ser Gly Phe Thr Phe Ser Thr Tyr
             20                  25                  30 cag atg gtg tgg gtg cgc cag gcc cca ggc aag ggc ctg gaa tgg gtg       144
Gln Met Val Trp Val Arg Gln Ala Pro Gly Lys Gly Leu Glu Trp Val
         35                  40                  45 tcc gtg atc tac ccc agc ggc gga ccc acc gtg tac gcc gac agc gtg       192
Ser Val Ile Tyr Pro Ser Gly Gly Pro Thr Val Tyr Ala Asp Ser Val
     50                  55                  60 aag ggc agg ttc acc atc agc agg gac aac agc aag aac acc ctg tac       240
Lys Gly Arg Phe Thr Ile Ser Arg Asp Asn Ser Lys Asn Thr Leu Tyr
 65                  70                  75                  80 ctg cag atg aac agc ctg agg gcc gag gac acc gcc gtg tac tac tgc       288
Leu Gln Met Asn Ser Leu Arg Ala Glu Asp Thr Ala Val Tyr Tyr Cys
             85                  90                  95 gcc agg ggc gag gac tac tac gac agc agc ggc cca ggc gcc ttc gac       336
Ala Arg Gly Glu Asp Tyr Tyr Asp Ser Ser Gly Pro Gly Ala Phe Asp
            100                 105                 110 atc tgg ggc cag ggc aca atg gtg acc gtg tcc agc                       372
Ile Trp Gly Gln Gly Thr Met Val Thr Val Ser Ser
        115                 120

<210> SEQ ID NO 42
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
             20                  25                  30

Gln Met Val Trp Val Arg Gln Ala Pro Gly Lys Gly Leu Glu Trp Val
         35                  40                  45

Ser Val Ile Tyr Pro Ser Gly Gly Pro Thr Val Tyr Ala Asp Ser Val
```

```
        50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
            115                 120

<210> SEQ ID NO 43
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
cagagcgccc tgacccagcc cagaagcgtg tccggcagcc caggccagag cgtgaccatc      60
agctgcaccg gcaccagcag cgacgtgggc ggctacaact acgtgtcctg gtatcagcag     120
caccccggca aggcccccaa gctgatgatc tacgacgtgt ccaagaggcc cagcggcgtg     180
cccgacaggt tcagcggcag caagagcggc aacaccgcca gcctgaccat ctccggactg     240
caggccgagg acgaggccga ctactactgc tgcagctacg ccggcagcta caccctggtg     300
ttcggcggag ggaccaagct gaccgtgctg ggccagccca ggctgccccc agcgtgacc     360 ctgttccccc ccagcagcga ggaactgcag gccaacaagg ccacactggt gtgcctgatc     420
agcgacttct acccaggcgc cgtgaccgtg gcctggaagg ccgacagcag ccccgtgaag     480
gccggcgtgg agacaaccac ccccagcaag cagagcaaca acaagtacgc cgccagcagc     540
tacctgagcc tgacccccga gcagtggaag tcccacaggt cctacagctg ccaggtgacc     600
cacgagggca gcaccgtgga gaaaaccgtg gcccccaccg agtgtagctg atga           654

<210> SEQ ID NO 44
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gaggtgcaat tgctggaaag cggcggagga ctggtgcagc caggcggcag cctgaggctg      60
tcctgcgccg ccagcggctt caccttcagc acctaccaga tggtgtgggt gcgccaggcc     120
ccaggcaagg gcctggaatg gtgtgtccgtg atctacccca gcggcggacc caccgtgtac     180
gccgacagcg tgaagggcag gttcaccatc agcagggaca cagcaagaa caccctgtac     240 ctgcagatga acagcctgag ggccgaggac accgccgtgt actactgcgc caggggcgag     300
gactactacg acagcagcgg cccaggcgcc ttcgacatct ggggccaggg cacaatggtg     360
accgtgtcca gcgccagcac caagggcccc agcgtgttcc cgctagcacc ttcctccaag     420
tccacctctg gcggcaccgc cgctctgggc tgcctggtga aggactactt ccctgagcct     480
gtgaccgtga gctggaactc tggcgccctg acctccggcg tgcataccct cctgccgtg     540 ctgcagtcct ccggcctgta ctccctgtcc tccgtggtga cagtgccttc ctcctccctg     600
ggcacccaga cctacatctg caacgtgaac cacaagccct ccaacaccaa ggtggacaag     660
```

```
cgggtggagc ctaagtcctg cgacaagacc cacacctgcc ctccctgccc tgcccctgag      720
ctgctgggcg accctccgt gttcctgttc cctcctaagc ctaaggacac cctgatgatc       780
tcccggaccc ctgaggtgac ctgcgtggtg gtggacgtgt cccacgagga cccagaggtg      840
aagtttaatt ggtatgtgga cggcgtggag gtccacaacg ccaagaccaa gcctcgggag      900
gaacagtaca actccaccta ccgggtggtg tccgtgctga ccgtgctgca ccaggactgg      960
ctgaacggca aggaatacaa gtgcaaagtc tccaacaagg ccctgcctgc ccccatcgag     1020
aaaaccatct ccaaggccaa gggccagcct cgcgagcctc aggtgtacac cctgcctcct     1080
agccgggagg aaatgaccaa gaaccaggtg tccctgacct gtctggtgaa gggcttctac     1140
ccttccgata tcgccgtgga gtgggagtcc aacggccagc ctgagaacaa ctacaagacc     1200 accccctcctg tgctggactc cgacggctcc ttcttcctgt actccaagct gaccgtggac    1260
aagtcccggt ggcagcaggg caacgtgttc tcctgctccg tgatgcacga ggccctgcac     1320
aaccactaca cccagaagtc cctgtccctg agccctggca agtga                     1365
```

<210> SEQ ID NO 45
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Ser Ser
    210                 215
```

<210> SEQ ID NO 46
<211> LENGTH: 455

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380
```

-continued

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Ser
    450             455
```

EVALUATING MMP EXPRESSION IN PATIENT STRATIFICATION AND OTHER THERAPEUTIC, DIAGNOSTIC AND PROGNOSTIC METHODS FOR CANCER

CROSS REFERENCE TO RELATED APPLICATIONS

This application claims priority to U.S. Application Ser. No. 61/008,153, filed on Dec. 17, 2007 and U.S. Application Ser. No. 61/025,017, filed on Jan. 31, 2008. The disclosures of the prior applications are considered part of (and are incorporated by reference in) the disclosure of this application.

BACKGROUND

The membrane type (MT)-matrix metalloproteinases (MMPs) constitute a sub-group of membrane-anchored MMPs that are major mediators of pericellular proteolysis and physiological activators of pro-MMP-2. MT-MMPs activate the zymogenic form of MMP-2 (pro-MMP-2 or pro-gelatinase A). MMP-2, in turn, can activate pro-MMP-9. The MT-MMPs comprise six members of plasma-tethered MMPs, which include four type I transmembrane enzymes (MMP-14, -15, -16, and -24) and two glycosylphosphatidylinositol-anchored enzymes (MMP-17 and -25). In addition to being potent extracellular matrix (ECM)-degrading enzymes, the type I transmembrane MT-MMPs can also initiate a cascade of zymogen activation on the cell surface.

MMPs are extensively studied in cancer and inflammation, and are well-validated in preclinical studies. Existing treatments for cancer, such as chemotherapy and radiotherapy improve the quality of life with no life-prolonging benefits and have significant side effects. Other treatments, such as MMP inhibitors, are being developed and further refined, and may work most effectively in cancers where certain MMPs are being expressed.

Patient stratification allows healthcare providers to assess the risk/benefit ratio of a given treatment and to predict what patients may best respond to a certain course of treatment. In general, the higher the risk of a particular disease, the better the risk/benefit ratio. Relative risk reduction by a given treatment is often similar across subgroups divided by sex, age, blood pressure etc.; however, if the absolute risk is low it may not be worth taking a treatment with serious side effects. Patient stratification is also important in assessing the cost effectiveness of treatment for a given set of patients.

SUMMARY

Provided are compositions and methods for quantifying the expression or activity of MMP-14 and other biomarkers of cancer, for example, osteotropic cancer, breast cancer, lung cancer, colon cancer or prostate cancer, which may be used diagnostically (e.g., to identify patients who have cancer, or a particular subclass of cancer) and prognostically (e.g., to identify patients who are likely to develop cancer or respond well to a particular therapeutic for treating cancer). Kits for detecting MMP-14 and other biomarkers and for the practice of the methods incorporating such detection are also described herein.

Specifically, in certain embodiments, provided are methods of utilizing expression of and/or expression ratios of any two of MMP-14, MMP-2 and MMP-9 in tumors and other cancer cells in order to stratify patients and identify those who would benefit from MMP-14 inhibitor treatment. For example, patients possessing tumors which express both MMP-14 and MMP-2 may be candidates for MMP-14 inhibitor treatment, and patients with tumors expressing MMP-14 and not MMP-2 may also benefit from MMP-14 inhibitor treatment. In another example, those patients with a high MMP-14/low MMP-9 expression ratio may benefit from MMP-14 inhibitor treatment. Further, by evaluating expression of MMP-14 and other MMP biomarkers (e.g., in a sample from a patient), patients can be diagnosed and potentially be stratified into groupings with different prognoses or drug responses. In some embodiments, "Low" and "High" refer to the intensity of immunohistochemistry staining for MMP-14 and MMP-9 expression in a carcinoma. For example, staining levels that are substantially the same as background levels of staining or about 10%, about 20%, about 30%, or about 40% greater than background levels of staining can be considered to be low levels; and staining levels that are about 2, about 3, about 4 fold or greater than background levels of staining can be considered to be high levels. As another example, in some embodiments, when the ratio of MMP-14/MMP-9 is >1, there is more MMP-14 expression than MMP-9 expression and is considered to be a favorable indicator of MMP-14 binding protein (e.g., DX-2400) responsiveness in preclinical models and subjects, e.g., subjects with cancer. In this embodiment, these subjects would benefit from and/or are good candidates for (e.g., would be selected for) treatment with an MMP-14 binding protein. In some embodiments, when the ratio is <1, MMP-9 expression is higher than MMP-14 expression, and that could be an indication of a non-responsive or low responsive tumor, e.g., in a subject with a tumor. In these embodiments, a subject with a ratio of <1 would not be selected for and/or would not benefit from treatment with an MMP-14 binding protein. Expression levels, e.g., levels of staining can be quantified, e.g., as described herein.

Compositions and kits for the practice of these methods are also described herein. These embodiments of the present invention, other embodiments, and their features and characteristics will be apparent from the description, drawings, and claims that follow.

BRIEF DESCRIPTION OF THE DRAWINGS

FIG. 1 illustrates the relative expression levels of various MMPs, including MMP-14 and MMP-2, in different cancer cell lines. TGI: Tumor Growth Inhibition.

FIGS. 2 and 3 illustrate the effect of DX-2400 on tumor progression in xenograft animal models created using the cancer cell lines of FIG. 1.

FIG. 4 illustrates the effect of DX-2400 on metastasis incidence in xenograft animal models created using the cancer cell lines of FIG. 1.

FIGS. 5A, 5B, 5C show the MMP-14 expression levels in selected cell lines by Western blot (WB) analysis (FIG. 5A); and the effect of a MMP-14 antibody (DX-2400) on MMP-14 positive (FIG. 5B) and MMP-14 negative (FIG. 5C) tumors.

DETAILED DESCRIPTION

For convenience, before further description of the present invention, certain terms employed in the specification, examples and appended claims are defined here.

The singular forms "a", "an", and "the" include plural references unless the context clearly dictates otherwise.

The term "agonist", as used herein, is meant to refer to an agent that mimics or up-regulates (e.g., potentiates or supplements) the bioactivity of a protein. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide with another molecule, e.g., a target peptide or nucleic acid.

"Antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound that downregulates expression of a gene or which reduces the amount of expressed protein present.

The term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J. Immunol. 1996; 26 (3):629-39)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDR"), interspersed with regions that are more conserved, termed "framework regions" ("FR"). The extent of the framework regions and CDRs has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH— terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "binding" refers to an association, which may be a stable association, between two molecules, e.g., between a polypeptide of the invention and a binding partner, due to, for example, electrostatic, hydrophobic, ionic and/or hydrogen-bond interactions under physiological conditions.

The term "binding protein" refers to a protein or polypeptide that can interact with a target molecule. This term is used interchangeably with "ligand." An "MMP-14 binding protein" refers to a protein that can interact with MMP-14, and includes, in particular, proteins that preferentially interact with and/or inhibit MMP-14. For example, the MMP-14 binding protein may be an antibody.

"Biological activity" or "bioactivity" or "activity" or "biological function", which are used interchangeably, refer to an effector or antigenic function that is directly or indirectly performed by a polypeptide (whether in its native or denatured conformation), or by any subsequence thereof. Biological activities include binding to polypeptides, binding to other proteins or molecules, activity as a DNA binding protein, as a transcription regulator, ability to bind damaged DNA, etc. A bioactivity may be modulated by directly affecting the subject polypeptide. Alternatively, a bioactivity may be altered by modulating the level of the polypeptide, such as by modulating expression of the corresponding gene.

The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The term "cancer" is meant to refer to an abnormal cell or cells, or a mass of tissue. The growth of these cells or tissues exceeds and is uncoordinated with that of the normal tissues or cells, and persists in the same excessive manner after cessation of the stimuli which evoked the change. These neoplastic tissues or cells show a lack of structural organization and coordination relative to normal tissues or cells which may result in a mass of tissues or cells which can be either benign or malignant. As used herein, cancer includes any neoplasm. This includes, but is not limited to, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, bone cancer, and the like.

A "combinatorial library" or "library" is a plurality of compounds, which may be termed "members," synthesized or otherwise prepared from one or more starting materials by employing either the same or different reactants or reaction conditions at each reaction in the library. In general, the members of any library show at least some structural diversity, which often results in chemical diversity. A library may have anywhere from two different members to about $10^8$ members or more. In certain embodiments, libraries of the present invention have more than about 12, 50 and 90 members. In certain embodiments of the present invention, the starting materials and certain of the reactants are the same, and chemical diversity in such libraries is achieved by varying at least one of the reactants or reaction conditions during the preparation of the library. Combinatorial libraries of the present invention may be prepared in solution or on the solid phase.

The term "diagnosing" includes prognosing and staging a disease or disorder.

"Gene" or "recombinant gene" refers to a nucleic acid molecule comprising an open reading frame and including at least one exon and (optionally) an intron sequence. "Intron" refers to a DNA sequence present in a given gene which is spliced out during mRNA maturation.

The terms "label" or "labeled" refer to incorporation or attachment, optionally covalently or non-covalently, of a detectable marker into a molecule, such as a polypeptide and especially an antibody. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance. Particular examples of labels which may be used under the invention include fluorescein, rhodamine, dansyl, umbelliferone, Texas red, luminol, NADPH, alpha-galactosidase, beta-galactosidase and horseradish peroxidase.

The "level of expression of a gene in a cell" or "gene expression level" refers to the level of mRNA, as well as pre-mRNA nascent transcript(s), transcript processing intermediates, mature mRNA(s) and degradation products, encoded by the gene in the cell.

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process. In certain instances, such regulation may be contingent on the occurrence of a specific event, such as activation of a signal transduction pathway, and/or may be manifest only in particular cell types.

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, anti-microbial agents, inhibitors of microbial infection or proliferation, and the like) by inclusion in assays. In such assays, many modulators may be screened at one time. The activity of a modulator may be known, unknown or partially known.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The term "osteotropic cancer" refers to metastatic cancer of the bone, i.e., a secondary cancer present in bone that originates from a primary cancer, such as that of the breast, lung, or prostate.

A "patient", "subject" or "host" to be treated by the subject method may mean either a human or non-human animal.

"Protein", "polypeptide" and "peptide" are used interchangeably herein when referring to a chain of amino acids prepared by protein synthesis techniques or to a gene product, e.g., as may be encoded by a coding sequence. By "gene product" it is meant a molecule that is produced as a result of transcription of a gene. Gene products include RNA molecules transcribed from a gene, as well as proteins translated from such transcripts.

"Recombinant protein", "heterologous protein" and "exogenous protein" are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

"Stage classification" or "staging" is generally, classification of cancer by progression observable by the naked eye, and TNM classification (tumor-node-metastasis staging) is widely used internationally. The "stage classification" used in the present invention corresponds to the TNM classification ("Rinsho, Byori, Genpatsusei Kangan Toriatsukaikiyaku (Clinical and Pathological Codes for Handling Primary Liver Cancer)": 22 p. Nihon Kangangaku Kenkyukai (Liver Cancer Study Group of Japan) edition (3rd revised edition), Kanehara Shuppan, 1992).

"Therapeutic agent" or "therapeutic" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents are known in the art and may be identified by their effects. Certain therapeutic agents are capable of regulating red cell proliferation and differentiation. Examples include chemotherapeutic nucleotides, drugs, hormones, non-specific (non-antibody) proteins, oligonucleotides (e.g., antisense oligonucleotides that bind to a target nucleic acid sequence (e.g., mRNA sequence)), peptides, and peptidomimetics.

The term "therapeutically effective amount" refers to that amount of a modulator, drug or other molecule which is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treating" as used herein is intended to encompass curing as well as ameliorating at least one symptom of any condition or disease.

MMP-14, MMP-2 and MMP-9 Biomarkers

Without wishing to be bound by theory, according to preferred embodiments of this disclosure, a cancer to be targeted with an anti-MMP-14 treatment (e.g., treatment with an MMP-14 binding protein, e.g., DX-2400) expresses MMP-14. In preferred embodiments, the MMP-14 is active. Thus, reagents, e.g., proteins (e.g., antibodies) that specifically bind the active form of MMP-14, e.g., DX-2400 (which binds to the catalytic domain of MMP-14) are suitable reagents to practice the methods described herein. In other embodiments, the total levels of MMP-14 (e.g., inactive and active MMP-14) are measured. As described herein, in a tumor model using cells which do not express MMP-14, the tumor xenograft of such cells did not respond to DX-2400 treatment.

In contrast, a tumor xenograft model using cells that express MMP-14 did respond to DX-2400 treatment.

According to another preferred embodiment, without being bound by theory, in determining responsiveness to anti-MMP-14 treatment (e.g., treatment with an MMP-14 binding protein, e.g., DX-2400), the levels of MMP-9 (e.g., active MMP-9) are determined. In preferred embodiments, low to no levels of active MMP-9 indicate that the tumor will be responsive to anti-MMP-14 treatment. For example, MMP-9 activity levels can be determined using in situ film zymography or by using an antibody that binds to the active form of MMP-9, e.g., to an active site on MMP-9. Examples of such antibodies include 539A-M0166-F10 and 539A-M0240-B03. As support for this model, experiments were performed using BxPC-3 cells which express active MMP-14 (bind DX-2400) but a tumor of these cells in a xenograft model did not respond in vivo to DX-2400 treatment (see FIG. 3). After analyzing the tumor tissue, it was determined that these cells had very high levels of active MMP-9 (data not shown).

The present invention is based at least in part on the observation that certain cancers, particularly osteotropic cancer or bone metastatic cancer cell lines, express MMP-14 and activate proMMP-2, and that MMP-14 inhibitors show enhanced efficacy in cancer cells expressing MMP-14, MMP-2 and/or MMP-9.

MMP-14

MMP-14 is encoded by a gene designated as MMP-14, matrix metalloproteinase-14 precursor. Synonyms for MMP-14 include matrix metalloproteinase 14 (membrane-inserted), membrane-type-1 matrix metalloproteinase, membrane-type matrix metalloproteinase 1, MMP-14, MMP-X1, MT1MMP, MT1-MMP, MTMMP1, MT-MMP1. MT-MMPs have similar structures, including a signal peptide, a pro-domain, a catalytic domain, a hinge region, and a hemopexin domain (Wang, et al., 2004, J Biol Chem, 279:51148-55). According to SwissProt entry P50281, the signal sequence of MMP-14 precursor includes amino acid residues 1-20. The pro-peptide includes residues 21-111. Cys93 is annotated as a possible cysteine switch. Residues 112 through 582 make up the mature, active protein. The catalytic domain includes residues 112-317. The hemopexin domains includes residues 318-523. The transmembrane segment comprises residues 542 through 562.

MMP-14 can be shed from cells or found on the surface of cells, tethered by a single transmembrane amino-acid sequence. See, e.g., Osnkowski et al. (2004, J Cell Physiol, 200:2-10).

An exemplary amino acid sequence of human MMP-14 is:

```
(SEQ ID NO: 1; Genbank Accession No. CAA88372.1)
MSPAPRPPRCLLLPLLTLGTALASLGSAQSSSFSPEAWLQQYGYLPPGDLRTHTQRSPQSLSAAIAAM

QKFYGLQVTGKADADTMKAMRRPRCGVPDKFGAEIKANVRRKRYAIQGLKWQHNEITFCIQNYTPKVG

EYATYEAIRKAFRVWESATPLRFREVPYAYIREGHEKQADIMIFFAEGFHGDSTPFDGEGGFLAHAYF

PGPNTGGDTHFDSAEPWTVRNEDLNGNDIFLVAVHELGHALGLEHSSDPSAIMAPFYQWMDTENFVLP

DDDRRGIQQLYGGESGFPTKMPPQPRTTSRPSVPDKPKNPTYGPNICDGNFDTVAMLRGEMFVFKERW

FWRVRNNQVMDGYPMPIGQFWRGLPASINTAYERKDGKFVFFKGDKHWVFDEASLEPGYPKHIKELGR

GLPTDKIDAALFWMPNGKTYFFRGNKYYRFNEELRAVDSEYPKNIKVWEGTPESPRGSFMGSDEVFTY

FYKGNKYWKFNNQKLKVEPGYPKSALRDWMGCPSGGRPDEGTEEETEVIIIEVDEEGGGAVSAAAVVL

PVLLLLLVLAVGLAVFFFRRHGTPRRLLYCQRSLLDKV.
```

An exemplary amino acid sequence of mouse MMP-14 is:

SEQ ID NO: 2
MSPAPRPSRSLLLPLLTLGTALASLGWAQGSNFSPEAWLQQYGYLPPGDL
RTHTQRSPQSLSAAIAAMQKFYGLQVTGKADLATMMAMRRPRCGVPDKFG
TEIKANVRRKRYAIQGLKWQHNEITFCIQNYTPKVGEYATFEAIRKAFRV
WESATPLRFREVPYAYIREGHEKQADIMILFAEGFHGDSTPFDGEGGFLA
HAYFPGPNIGGDTHFDSAEPWTVQNEDLNGNDIFLVAVHELGHALGLEHS
NDPSAIMSPFYQWMDTENFVLPDDDRRGIQQLYGSKSGSPTKMPPQPRTT
SRPSVPDKPKNPAYGPNICDGNFDTVAMLRGEMFVFKERWFWRVRNNQVM
DGYPMPIGQFWRGLPASINTAYERKDGKFVFFKGDKHWVFDEASLEPGYP
KHIKELGRGLPTDKIDAALFWMPNGKTYFFRGNKYYRFNEEFRAVDSEYP

KNIKVWEGIPESPRGSFMGSDEVFTYFYKGNKYWKFNNQKLKVEPGYPKS
ALRDWMGCPSGRRPDEGTEEETEVIIIEVDEEGSGAVSAAAVVLPVLLLL
LVLAVGLAVFFFRRHGTPKRLLYCQRSLLDKV; GenBank Accession No. NP_032634.2.

An exemplary MMP-14 protein can consist of or comprise the human or mouse MMP-14 amino acid sequence, a sequence that is 80%, 85%, 90%, 95%, 96%, 97%, 98%, or 99% identical to one of these sequences, or a fragment thereof, e.g., a fragment without the signal sequence or pro-domain.

The mRNA sequences of human and murine MMP-14 may be found at GenBank Accession Nos Z48481 and NM_008608, respectively. The sequences of human and mouse MMP-14 mRNAs are as follows:

```
SEQ ID NQ: 3: human MMP-14 mRNA
   1 aagttcagtg cctaccgaag acaaaggcgc cccgagggag tggcggtgcg accccagggc
  61 gtgggcccgg ccgcggagcc cacactgccc ggctgacccg gtggtctcgg accatgtctc
 121 ccgccccaag acccccccgt tgtctcctgc tcccctgct cacgctcggc accgcgctcg
 181 cctccctcgg ctcggcccaa agcagcagct tcagccccga agcctggcta cagcaatatg
 241 gctacctgcc tcccggggac ctacgtaccc acacacagcg ctcaccccag tcactctcag
 301 cggccatcgc tgccatgcag aagttttacg gcttgcaagt aacaggcaaa gctgatgcag
 361 acaccatgaa ggccatgagg cgcccccgat gtggtgttcc agacaagttt ggggctgaga
 421 tcaaggccaa tgttcgaagg aagcgctacg ccatccaggg tctcaaatgg caacataatg
 481 aaatcacttt ctgcatccag aattacaccc ccaaggtggg cgagtatgcc acatacgagg
 541 ccattcgcaa ggcgttccgc gtgtgggaga gtgccacacc actgcgcttc cgcgaggtgc
 601 cctatgccta catccgtgag ggccatgaga agcaggccga catcatgatc ttctttgccg
 661 agggcttcca tggcgacagc acgcccttcg atggtgaggg cggcttcctg gcccatgcct
 721 acttcccagg ccccaacatt ggaggagaca cccactttga ctctgccgag ccttggactg
 781 tcaggaatga ggatctgaat ggaaatgaca tcttcctggt ggctgtgcac gagctgggcc
 841 atgccctggg gctcgagcat tccagtgacc cctcggccat catggcaccc ttttaccagt
 901 ggatggacac ggagaatttt gtgctgcccg atgatgaccg ccggggcatc cagcaacttt
 961 atggggtga gtcagggttc cccaccaaga tgccccctca acccaggact acctcccggc
1021 cttctgttcc tgataaaccc aaaaacccca cctatgggcc caacatctgt gacgggaact
1081 ttgacaccgt ggccatgctc cgaggggaga tgtttgtctt caaggagcgc tggttctggc
1141 gggtgaggaa taaccaagtg atggatggat acccaatgcc cattggccag ttctggcggg
1201 gcctgcctgc gtccatcaac actgcctacg agaggaagga tggcaaattc gtcttcttca
1261 aggagacaa gcattgggtg tttgatgagg cgtccctgga acctggctac cccaagcaca
1321 ttaaggagct gggccgaggg ctgcctaccg acaagattga tgctgctctc ttctggatgc
1381 ccaatggaaa gacctacttc ttccgtggaa acaagtacta ccgtttcaac gaagagctca
1441 gggcagtgga tagcgagtac cccaagaaca tcaaagtctg ggaagggatc cctgagtctc
1501 ccagagggtc attcatgggc agcgatgaag tcttcactta cttctacaag gggaacaaat
1561 actggaaatt caacaaccag aagctgaagg tagaaccggg ctaccccaag tcagccctga
1621 gggactggat gggctgccca tcgggaggcc ggcggatga ggggactgag gaggagacgg
```

-continued

```
1681 aggtgatcat cattgaggtg dacgaggagg gcggcggggc ggtgagcgcg gctgccgtgg 1741 tgctgcccgt gctgctgctg ctcctggtgc tggcggtggg ccttgcagtc ttcttcttca 1801 gacgccatgg gaccccagg cgactgctct actgccagcg ttccctgctg gacaaggtct 1861 gacgcccacc gccggcccgc ccactcctac cacaaggact tgcctctga aggccagtgg 1921 cagcaggtgg tggtgggtgg gctgctccca tcgtcccgag ccccctcccc gcagcctcct 1981 tgcttctctc tgtcccctgg ctggcctcct tcaccctgac cgcctccctc cctcctgccc 2041 cggcattgca tcttccctag ataggtcccc tgagggctga gtgggagggc ggccctttcc 2101 agcctctgcc cctcagggga accctgtagc tttgtgtctg tccagcccca tctgaatgtg 2161 ttgggggctc tgcacttgaa ggcaggaccc tcagacctcg ctggtaaagg tcaaatgggg 2221 tcatctgctc cttttccatc ccctgacata ccttaacctc tgaactctga cctcaggagg 2281 ctctgggcac tccagcctg aaagccccag gtgtacccaa ttggcagcct ctcactactc 2341 tttctggcta aaaggaatct aatcttgttg agggtagaga ccctgagaca gtgtgagggg 2401 gtggggactg ccaagccacc ctaagacctt gggaggaaaa ctcagagagg gtcttcgttg 2461 ctcagtcagt caagttcctc ggagatctgc ctctgcctca cctaccccag ggaacttcca 2521 aggaaggagc ctgagccact ggggactaag tgggcagaag aaacccttgg cagccctgtg 2581 cctctcgaat gttagccttg gatggggctt tcacagttag aagagctgaa accaggggtg 2641 cagctgtcag gtagggtggg gccggtggga gaggcccggg tcagagccct ggggtgagc 2701 ctgaaggcca cagagaaaga accttgccca aactcaggca gctggggctg aggcccaaag 2761 gcagaacagc cagaggggc aggaggggac caaaaaggaa aatgaggacg tgcagcagca 2821 ttggaaggct ggggccgggc aggccaggcc aagccaagca gggggccaca gggtgggctg 2881 tggagctctc aggaagggcc ctgaggaagg cacacttgct cctgttggtc cctgtccttg 2941 ctgcccaggc agcgtggagg ggaagggtag ggcagccaga gaaaggagca gagaaggcac 3001 acaaacgagg aatgagggc ttcacgagag gccacagggc ctggctggcc acgctgtccc 3061 ggcctgctca ccatctcagt gagggcagg agctggggct cgcttaggct gggtccacgc 3121 ttccctggtg ccagcacccc tcaagcctgt ctcaccagtg gcctgccctc tcgctccccc 3181 acccagccca cccattgaag tctccttggg ccaccaaagg tggtggccat ggtaccgggg 3241 acttgggaga gtgagaccca gtggaggag caagaggaga gggatgtcgg gggggtgggg 3301 cacggggtag gggaaatggg gtgaacggtg ctggcagttc ggctagattt ctgtcttgtt 3361 tgttttttg ttttgtttaa tgtatatttt tattataatt attatatatg aattccaaaa 3421 aaaaaaaaa aaaaaaa
```

SEQ ID NO: 4: mouse MMP-14 mRNA

```
  1 caaaggagag cagagagggc ttccaactca gttcgccgac taagcagaag aaagatcaaa 61 aacggaaaag agaagagcaa acagacattt ccaggagcaa ttccctcacc tccaagccga 121 ccgcgctcta ggaatccaca ttccgttcct ttagaagaca aaggcgcccc aagagaggcg 181 gcgcgacccc agggcgtggg ccccgccgcg gagcccgcac cgccggcgc cccgacgccg 241 gggaccatgt ctcccgcccc tcgaccctcc cgcagcctcc tgctcccct gctcacgctt 301 ggcacggcgc tcgcctccct cggctgggcc caaggcagca acttcagccc cgaagcctgg 361 ctgcagcagt atggctacct acctccaggg gacctgcgta cccacacaca acgctcaccc 421 cagtcactct cagctgccat tgccgccatg caaaagttct atggtttaca agtgacaggc 481 aaggctgatt tggcaaccat gatggccatg aggcgccctc gctgtggtgt tccggataag 541 tttgggactg agatcaaggc caatgttcgg aggaagcgct atgccattca gggcctcaag
```

-continued

```
 601 tggcagcata atgagatcac tttctgcatt cagaattaca cccctaaggt gggcgagtat 661 gccacattcg aggccattcg gaaggccttc cgagtatggg agagtgccac gccactgcgc 721 ttccgagaag tgccctatgc ctacatccgg gagggacatg agaagcaggc tgacatcatg 781 atcttatttg ctgagggttt ccacggcgac agtacaccct ttgatggtga aggagggttc 841 ctggctcatg cctacttccc aggccccaat attggagggg atacccactt tgattctgcc 901 gagccctgga ctgtccaaaa tgaggatcta aatgggaatg acatcttctt ggtggctgtg 961 catgagttgg ggcatgccct aggcctggaa cattctaacg atccctccgc catcatgtcc 1021 cccttttacc agtggatgga cacagagaac ttcgtgttgc ctgatgacga tcgccgtggc 1081 atccagcaac tttatggaag caagtcaggg tcacccacaa agatgccccc tcaacccaga 1141 actacctctc ggccctctgt cccagataag cccaaaaacc ccgcctatgg gcccaacatc 1201 tgtgacggga actttgacac cgtggccatg ctccgaggag agatgtttgt cttcaaggag 1261 cgatggttct ggcgggtgag gaataaccaa gtgatggatg gatacccaat gccccattggc 1321 caattctgga ggggcctgcc tgcatccatc aatactgcct acgaaaggaa ggatggcaaa 1381 tttgtcttct tcaaaggaga taagcactgg gtgtttgacg aagcctccct ggaacccggg 1441 taccccaagc acattaagga gcttggccga gggctgccca cggacaagat cgatgcagct 1501 ctcttctgga tgcccaatgg gaagacctac ttcttccggg gcaataagta ctaccggttc 1561 aatgaagaat tcagggcagt ggacagcgag tacccctaaaa acatcaaagt ctgggaagga 1621 atccctgaat ctcccagggg gtcattcatg ggcagtgatg aagtcttcac atacttctac 1681 aagggaaaca aatactggaa gttcaacaac cagaagctga aggtagagcc agggtacccc 1741 aagtcagctc tgcgggactg gatgggctgc ccttcggggc gccggcccga tgagggact 1801 gaggaggaga cagaggtgat catcattgag gtggatgagg agggcagtgg agctgtgagt 1861 gcggccgccg tggtcctgcc ggtactactg ctgctcctgg tactggcagt gggcctcgct 1921 gtcttcttct tcagacgcca tgggacgccc aagcgactgc tttactgcca gcgttcgctg 1981 ctggacaagg tctgacccc  accactggcc cacccgcttc taccacaagg actttgcctc 2041 tgaaggccag tggctacagg tggtagcagg tgggctgctc tcacccgtcc tgggctccct 2101 ccctccagcc tcccttctca gtccctaatt ggcctctccc accctcaccc cagcattgct 2161 tcatccataa gtgggtccct tgagggctga gcagaagacg gtcggcctct ggccctcaag 2221 ggaatctcac agctcagtgt gtgttcagcc ctagttgaat gttgtcaagg ctcttattga 2281 aggcaagacc ctctgaccct ataggcaacg gccaaatggg gtcatctgct tcttttccat 2341 cccctaact  acataccta  aatctctgaa ctctgacctc aggaggctct gggcatatga 2401 gccctatatg taccaagtgt acctagttgg ctgcctcccg ccactctgac taaaaggaat 2461 cttaagagtg tacatttgga ggtggaaaga ttgttcagtt taccctaaag actttgataa 2521 gaaagagaaa gaaagaaaga aagaaagaaa gaaagaaaga aagaaagaaa gaaaaaaaaa 2581 aaa
```

An exemplary MMP-14 gene can consist of or comprise the human or mouse MMP-14 mRNA sequence, a sequence that is 80%, 85%, 90%, 95%, 96%, 97%, 98%, or 99% identical to one of these sequences, or a fragment thereof.

MMP-2

MMP-14 activates pro-MMP-2 causing a cascade of proteolysis that facilitates the mobility and invasiveness of tumor cells (Berno, et al., 2005, Endocr Relat Cancer, 12:393-406; Anilkumar, et al., 2005, Faseb J, 19:1326-8; Itoh and Seiki, 2005, J Cell Physiol; Lopez de Cicco, et al., 2005, Cancer Res, 65:4162-71; El Bedoui, et al., 2005, Cardiovasc Res, 67:317-25; Cao, et al., 2005, Thromb Haemost, 93:770-8; Sato, et al., 2005, Cancer Sci, 96:212-7; Dong, et al., 2005, Am J Pathol, 166:1173-86; Philip, et al., 2004, Glycoconj J, 21:429-41; Guo, et al., 2005, Am J Pathol, 166:877-90; Grossman, 2005, Urol Oncol, 23:222; Gilles, et al., 2001, J Cell Sci, 114:2967-76). Studies propose that this activation process requires both active MT1-MMP and the TIMP-2-bound MT1-MMP (Strongin et al, 1995, J Biol Chem, 270, 5331-5338; Butler et al, 1998, J Biol Chem, 273: 871-80 Kinoshita et al, 1998, J Biol Chem, 273, 16098-103). The TIMP-2 in the latter complex binds, through its C-terminal domain, to the hemopexin domain of pro-MMP-2, which may localize the zymogen close to the active MT1-MMP (Butler et al, 1998, J Biol Chem, 273: 871-80; Kinoshita et al, 1998).

MMP-2 is encoded by a gene designated as MMP-2, matrix metalloproteinase 2 preproprotein. Synonyms for MMP-2 include matrix metalloproteinase 2 (gelatinase A, 72 kD gelatinase, 72 kD type IV collagenase), TBE-1 (as secreted by H-ras oncogene-transformed human bronchial epithelial cells), MMP-II, CLG4, and CLG4A.

An exemplary amino acid sequence of human MMP-2 is:

```
MEALMARGAL TGPLRALCLL GCLLSHAAAA PSPIIKFPGD
VAPKTDKELA VQYLNTFYGC PKESCNLFVL KDTLKKMQKF
FGLPQTGDLD QNTIETMRKP RGGNPDVANY NFFPRKPKWD
KNQITYRIIG YTPDLDPETV DDAFARAFQV WSDVTPLRFS
RIHDGEADIM INFGRWEHGD GYPFDGKDGL LAHAFAPGTG
VGGDSHFDDD ELWTLGEGQV VRVKYGNADG EYCKFPPLFN
GKEYNSCTDT GRSDGFLWCS TTYNFEKDGK YGFCPHEALF
TMGGNAEGQP CKFPFRFQGT SYDSCTTEGR TDGYRWCGTT
EDYDRDKKYG FCPETAMSTV GGNSEGAPCV FPFTFLGNKY
ESCTSAGRSD GKMWCATTAN YDDDRKWGFC PDQGYSLFLV
AAHEFGHAMG LEHSQDPGAL MAPIYTYTKN FRLSQDDIKG
IQELYGASPD IDLGTGPTPT LGPVTPEICK QDIVFDGIAQ
IRGEIFFFKD RFIWRTVTPR DKPMGPLLVA TFWPELPEKI
DAVYEAPQEE KAVFFAGNEY WIYSASTLER GYPKPLTSLG
LPPDVQRVDA AFNWSKNKKT YIFAGDKFWR YNEVKKKMDP
GFPKLIADAW NAIPDNLDAV VDLQGGGHSY FFKGAYYLKL
ENQSLKSVKF GSIKSDWLGC (SEQ ID NO: 5; Genbank
Accession No. NP_004521.1).
```

An exemplary amino acid sequence of murine MMP-2 is:

```
MEARVAWGAL AGPLRVLCVL CCLLGRAIAA PSPIIKFPGD
VAPKTDKELA VQYLNTFYGC PKESCNLFVL KDTLKKMQKF
FGLPQTGDLD QNTIETMRKP RCGNPDVANY NFFPRKPKWD
KNQITYRIIG YTPDLDPETV DDAFARALKV WSDVTPLRFS
RIHDGEADIM INFGRWEHGD GYPFDGKDGL LAHAFAPGTG
VGGDSHFDDD ELWTLGEGQV VRVKYGNADG EYCKFPPLFN
GREYSSCTDT GRSDGFLWCS TTYNFEKDGK YGFCPHEALF
TMGGNADGQP CKFPFRFQGT SYNSCTTEGR TDGYRWCGTT
EDYDRDKKYG FCPETAMSTV GGNSEGAPCV FPFTFLGNKY
ESCTSAGRND GKVWCATTTN YDDDRKWGFC PDQGYSLFLV
AAHEFGHAMG LEHSQDPGAL MAPIYTYTKN FRLSHDDIKG
IQELYGPSPD ADTDTGTGPT PTLGPVTPEI CKQDIVFDGI
AQIRGEIFFF KDRFIWRTVT PRDKPTGPLL VATFWPELPE
KIDAVYEAPQ EEKAVFFAGN EYWVYSASTL ERGYPKPLTS
LGLPPDVQQV DAAFNWSKNK KTYIFAGDKF WRYNEVKKKM
DPGFPKLIAD SWNAIPDNLD AVVDLQGGGH SYFFKGAYYL
KLENQSLKSV KFGSIKSDWL GC (SEQ ID NO: 6; Genbank
Accession No. NP_032636.1).
```

An exemplary MMP-2 protein can consist of or comprise the human or mouse MMP-2 amino acid sequence, a sequence that is 80%, 85%, 90%, 95%, 96%, 97%, 98%, or 99% identical to one of these sequences, or a fragment thereof, e.g., a fragment without the signal sequence or pro-domain.

The mRNA sequences of human and murine MMP-2 may be found at GenBank Accession Nos NM_004530 and NM_008610, respectively. The sequences of human and mouse MMP-2 mRNAs are as follows:

```
SEQ ID NO: 7: human MMP-2 mRNA
   1 gcggctgccc tcccttgttt ccgctgcatc cagacttcct caggcggtgg ctggaggctg
  61 cgcatctggg gctttaaaca tacaaaggga ttgccaggac ctgcggcggc ggcggcggcg
 121 gcggggctg gggcgcgggg gccggaccat gagccgctga gccgggcaaa ccccaggcca
 181 ccgagccagc ggaccctcgg agcgcagccc tgcgccgcgg agcaggctcc aaccaggcgg
 241 cgaggcggcc acacgcaccg agccagcgac ccccgggcga cgcgcggggc cagggagcgc
 301 tacgatggag gcgctaatgg cccgggcgc gctcacgggt ccctgaggg cgctctgtct
 361 cctgggctgc ctgctgagcc acgccgccgc cgcgccgtcg cccatcatca gttccccgg
 421 cgatgtcgcc cccaaaacgg acaaagagtt ggcagtgcaa tacctgaaca ccttctatgg
 481 ctgccccaag gagagctgca acctgtttgt gctgaaggac acactaaaga agatgcagaa
 541 gttctttgga ctgccccaga caggtgatct tgaccagaat accatcgaga ccatgcggaa
 601 gccacgctgc ggcaacccag atgtggccaa ctacaacttc ttccctcgca gcccaagtg
 661 ggacaagaac cagatcacat acaggatcat tggctacaca cctgatctgg acccagagac
 721 agtggatgat gcctttgctc gtgccttcca agtctggagc gatgtgaccc cactgcggtt
 781 ttctcgaatc catgatggag aggcagacat catgatcaac tttggccgct gggagcatgg
```

-continued

```
 841 cgatggatac ccctttgacg gtaaggacgg actcctggct catgccttcg ccccaggcac
 901 tggtgttggg ggagactccc attttgatga cgatgagcta tggaccttgg gagaaggcca
 961 agtggtccgt gtgaagtatg ggaacgccga tggggagtac tgcaagttcc ccttcttgtt
1021 caatggcaag gagtacaaca gctgcactga taccggccgc agcgatggct tcctctggtg
1081 ctccaccacc tacaactttg agaaggatgg caagtacggc ttctgtcccc atgaagccct
1141 gttcaccatg gcggcaacg ctgaaggaca gccctgcaag tttccattcc gcttccaggg
1201 cacatcctat gacagctgca ccactgaggg ccgcacggat ggctaccgct ggtgcggcac
1261 cactgaggac tacgaccgcg acaagaagta tggcttctgc cctgagaccg ccatgtccac
1321 tgttggtggg aactcagaag gtgcccctg tgtcttcccc ttcactttcc tgggcaacaa
1381 atatgagagc tgcaccagcg ccggccgcag tgacggaaag atgtggtgtg cgaccacagc
1441 caactacgat gatgaccgca agtggggctt ctgccctgac caagggtaca gcctgttcct
1501 cgtggcagcc cacgagtttg ccacgccat ggggctggag cactcccaag accctggggc
1561 cctgatggca cccatttaca cctacaccaa gaacttccgt ctgtcccagg atgacatcaa
1621 gggcattcag gagctctatg gggcctctcc tgacattgac cttggcaccg ccccaccc
1681 cacgctgggc cctgtcactc ctgagatctg caaacaggac attgtatttg atggcatcgc
1741 tcagatccgt ggtgagatct tcttcttcaa ggaccggttc atttggcgga ctgtgacgcc
1801 acgtgacaag cccatggggc ccctgctggt ggccacattc tggcctgagc tcccggaaaa
1861 gattgatgcg gtatacgagg caccacagga ggagaaggct gtgttctttg cagggaatga
1921 atactggatc tactcagcca gcaccctgga gcgagggtac cccaagccac tgaccagcct
1981 gggactgccc cctgatgtcc agcgagtgga tgccgccttt aactggagca aaaacaagaa
2041 gacatacatc tttgctggag acaaattctg gagatacaat gaggtgaaga gaaaatgga
2101 tcctggcttc cccaagctca tcgcagatgc ctggaatgcc atccccgata acctggatgc
2161 cgtcgtggac ctgcagggcg gcggtcacag ctacttcttc aagggtgcct attacctgaa
2221 gctggagaac caaagtctga agagcgtgaa gtttggaagc atcaaatccg actggctagg
2281 ctgctgagct ggccctggct cccacaggcc cttcctctcc actgccttcg atacaccggg
2341 cctggagaac tagagaagga cccggagggg cctggcagcc gtgccttcag ctctacagct
2401 aatcagcatt ctcactccta cctggtaatt taagattcca gagagtggct cctcccggtg
2461 cccaagaata gatgctgact gtactcctcc caggcgcccc ttccccctcc aatcccacca
2521 accctcagag ccaccctaa agagatactt tgatatttc aacgcagccc tgctttgggc
2581 tgccctggtg ctgccacact tcaggctctt ctccttcac aaccttctgt ggctcacaga
2641 acccttggag ccaatggaga ctgtctcaag agggcactgg tggcccgaca gcctggcaca
2701 gggcagtggg acagggcatg ccaggtggc cactccagac ccctggcttt tcactgctgg
2761 ctgccttaga accttctta cattagcagt ttgctttgta tgcactttgt tttttcttt
2821 gggtcttgtt ttttttttcc acttagaaat tgcatttcct gacagaagga ctcaggttgt
2881 ctgaagtcac tgcacagtgc atctcagccc acatagtgat ggttcccctg ttcactctac
2941 ttagcatgtc cctaccgagt ctcttctcca ctggatggag gaaaaccaag ccgtggcttc
3001 ccgctcagcc ctccctgccc ctcccttcaa ccattcccca tgggaaatgt caacaagtat
3061 gaataaagac acctactgag tggccgtgtt tgccatctgt tttagcagag cctagacaag
3121 ggccacagac ccagccagaa gcggaaactt aaaaagtccg aatctctgct ccctgcaggg
3181 cacaggtgat ggtgtctgct ggaaaggtca gagcttccaa agtaaacagc aagagaacct
```

-continued

```
3241 cagggagagt aagctctagt ccctctgtcc tgtagaaaga gccctgaaga atcagcaatt 3301 ttgttgcttt attgtggcat ctgttcgagg tttgcttcct ctttaagtct gtttcttcat 3361 tagcaatcat atcagtttta atgctactac taacaatgaa cagtaacaat aatatccccc 3421 tcaattaata gagtgctttc tatgtgcaag gcacttttca cgtgtcacct attttaacct 3481 ttccaaccac ataaataaaa aaggccatta ttagttgaat cttattgatg aagagaaaaa 3541 aaaaaa
```

SEQ ID NO: 8: mouse MMP-2 mRNA

```
   1 ccagccggcc acatctggcg tctgcccgcc cttgtttccg ctgcatccag acttccctgg 61 tggctggagg ctctgtgtgc atccaggagt ttagatatac aaagggattg ccaggacctg 121 caagcacccg cggcagtggt gtgtattggg acgtgggacc ccgttatgag ctcctgagcc 181 ccgagaagca gaggcagtag agtaagggga tcgccgtgca gggcaggcgc cagccgggcg 241 gaccccaggg cacagccaga gacctcaggg tgacacgcgg agcccgggag cgcaacgatg 301 gaggcacgag tggcctgggg agcgctgccc ggacctctgc gggttctctg cgtcctgtgc 361 tgcctgttgg gccgcgccat cgctgcacca tcgcccatca tcaagttccc cggcgatgtc 421 gcccctaaaa cagacaaaga gttggcagtg caatacctga acactttcta tggctgcccc 481 aaggagagtt gcaacctctt tgtgctgaaa gatacccctca agaagatgca gaagttcttt 541 gggctgcccc agacaggtga ccttgaccag aacaccatcg agaccatgcg gaagccaaga 601 tgtggcaacc cagatgtggc caactacaac ttcttccccc gcaagcccaa gtgggacaag 661 aaccagatca catacaggat cattggttac acacctgacc tggaccctga accgtggat 721 gatgcttttg ctcgggcctt aaaagtatgg agcgacgtca ctccgctgcg cttttctcga 781 atccatgatg gggaggctga catcatgatc aactttggac gctgggagca tggagatgga 841 tacccatttg atggcaagga tggactcctg gcacatgcct ttgcccccggg cactggtgtt 901 ggggagatt ctcactttga tgatgatgag ctgtggaccc tgggagaagg acaagtggtc 961 cgcgtaaagt atgggaacgc tgatggcgag tactgcaagt tcccccttcct gttcaacggt 1021 cgggaataca gcagctgtac agacactggt cgcagtgatg gcttcctctg gtgctccacc 1081 acatacaact tgagaagga tggcaagtat ggcttctgcc cccatgaagc cttgtttacc 1141 atgggtggca atgcagatgg acagccctgc aagttcccgt tccgcttcca gggcacctcc 1201 tacaacagct gtaccaccga gggccgcacc gatggctacc gctggtgtgg caccaccgag 1261 gactatgacc gggataagaa gtatggattc tgtcccgaga ccgctatgtc cactgtgggt 1321 ggaaattcag aaggtgcccc atgtgtcttc ccccttcactt tcctgggcaa caagtatgag 1381 agctgcacca gcgccggccg caacgatggc aaggtgtggt gtgcgaccac aaccaactac 1441 gatgatgacc ggaagtgggg cttctgtcct gaccaaggat atagcctatt cctcgtggca 1501 gcccatgagt tcggccatgc catggggctg aacactctc aggaccctgg agctctgatg 1561 gccccgatct acacctacac caagaacttc gattatccc atgatgacat caaggggatc 1621 caggagctct atgggccctc ccccgatgct gatactgaca ctggtactgg ccccacacca 1681 acactgggac ctgtcactcc ggagatctgc aaacaggaca ttgtctttga tggcatcgct 1741 cagatccgtg gtgagatctt cttcttcaag gaccggttta tttggcggac agtgacacca 1801 cgtgacaagc ccacaggtcc cttgctggtg gccacattct ggcctgagct cccagaaaag 1861 attgacgctg tgtatgaggc cccacaggag gagaaggctg tgttcttcgc agggaatgag 1921 tactgggtct attctgctag tactctggag cgaggatacc caagccact gaccagcctg 1981 ggggttgccc ctgatgtcca gcaagtagat gctgccttta actggagtaa gaacaagaag
```

```
-continued
2041 acatacatct ttgcaggaga caagttctgg agatacaatg aagtgaagaa gaaaatggac 2101 cccggtttcc ctaagctcat cgcagactcc tggaatgcca tccctgataa cctggatgcc 2161 gtcgtggacc tgcagggtgg tggtcatagc tacttcttca agggtgctta ttacctgaag 2221 ctggagaacc aaagtctcaa gagcgtgaag tttggaagca tcaaatcaga ctggctgggc 2281 tgctgagctg gccctgttcc cacgggccct atcatcttca tcgctgcaca ccaggtgaag 2341 gatgtgaagc agcctggcgg ctctgtcctc ctctgtagtt aaccagcctt ctccttcacc 2401 tggtgacttc agatttaaga gggtggcttc tttttgtgcc caaagaaagg tgctgactgt 2461 accctcccgg gtgctgcttc tccttcctgc ccaccctagg ggatgcttgg atatttgcaa 2521 tgcagccctc ctctgggctg ccctggtgct ccactcttct ggttcttcaa catctatgac 2581 cttttttatgg ctttcagcac tctcagagtt aatagagact ggcttaggag ggcactggtg 2641 gccctgttaa cagcctggca tggggcagtg gggtacaggt gtgccaaggt ggaaatcaga 2701 gacacctggt ttcacccttt ctgctgccca gacacctgca ccaccttaac tgttgctttt 2761 gtatgccctt cgctcgtttc cttcaacctt ttcagttttc cactccactg catttcctgc 2821 ccaaaggact cgggttgtct gacatcgctg catgatgcat ctcagcccgc ctagtgatgg 2881 ttcccctcct cactctgtgc agatcatgcc cagtcacttc ctccactgga tggaggagaa 2941 ccaagtcagt ggcttcctgc tcagccttct tgcttctccc tttaacagtt ccccatggga 3001 aatggcaaac aagtataaat aaagacaccc attgagtgac aaaaaaaaaa aaaaaaaaa 3061 aaaaaaaaa
```

An exemplary MMP-2 gene can consist of or comprise the human or mouse MMP-2 mRNA sequence, a sequence that is 80%, 85%, 90%, 95%, 96%, 97%, 98%, or 99% identical to one of these sequences, or a fragment thereof.

MMP-9

MMP-9 is a Zn+2 dependent endopeptidase, synthesized and secreted in monomeric form as zymogen. The structure is almost similar to MMP2. The nascent form of the protein shows an N-terminal signal sequence ("pre" domain) that directs the protein to the endoplasmic reticulum. The pre domain is followed by a propeptide-"pro" domain that maintains enzyme-latency until cleaved or disrupted, and a catalytic domain that contains the conserved zinc-binding region. A hemopexin/vitronectin-like domain is also seen, that is connected to the catalytic domain by a hinge or linker region. The hemopexin domain is involved in TIMP (Tissue Inhibitors of Metallo-Proteinases) binding e.g., TIMP-1 & TIMP-3, the binding of certain substrates, membrane activation, and some proteolytic activities. It also shows a series of three head-to-tail cysteine-rich repeats within its catalytic domain. These inserts resemble the collagen-binding type II repeats of fibronectin and are required to bind and cleave collagen and elastin.

Its primary function is degradation of proteins in the extracellular matrix. It proteolytically digests decorin, elastin, fibrillin, laminin, gelatin (denatured collagen), and types IV, V, XI and XVI collagen and also activates growth factors like proTGFb and proTNFa. Physiologically, MMP-9 in coordination with other MMPs, play a role in normal tissue remodeling events such as neurite growth, embryonic development, angiogenesis, ovulation, mammary gland involution and wound healing. MMP-9 with other MMPs is also involved in osteoblastic bone formation and/or inhibits osteoclastic bone resorption.

MMP-9 is encoded by a gene designated as matrix metallopeptidase 9 (gelatinase B, 92 kDa gelatinase, 92 kDa type IV collagenase). Synonyms for MMP-9 include CLG4 (Collagenase Type IV), CLG4B (Collagenase Type IV-B), and GELB (Gelatinase B).

An exemplary amino acid sequence of human MMP-9 is:

```
  1 mslwqplvlv llvlgccfaa prqrqstlvl fpgdlrtnlt drqlaeeyly rygytrvaem 61 rgeskslgpa llllqkqlsl petgeldsat lkamrtprcg vpdlgrfqtf egdlkwhhhn 121 itywiqnyse dipravidda farafalwsa vtpltftrvy srdadiviqf qvaehqdgyp 181 fdgkdgllah afppgpqiqg dahfdddelw slgkgvvvpt rfgnadgaac hfpfifegrs 241 ysacttdgrs dglpwcstta nydtddrfgf cpserlytqd gnadgkpcqf pfifqgqsys 301 acttdgrsdg yrwcattany drdklfgfcp tradstvmgg nsaqelcvfp ftflgkeyst 361 ctsegrgdgr lwcattsnfd sdkkwgfcpd qgyslflvaa hefghalgld hssvpealmy 421 pmyrftegpp lhkddvngir hlygprpepe prppttttpq ptapptvcpt gpptvhpser 481 ptagptgpps agptgpptag pstattvpls pvddacnvni fdaiaeignq lylfkdgkyw
```

-continued

```
541 rfsegrgsrp qgpfliadkw palprkldsv feerlskklf ffsgrqvwvy tgasvlgprr 601 ldklglgadv aqvtgalrsg rgkmllfsgr rlwrfdvkaq mvdprsasev drmfpgvpld 661 thdvfqyrek ayfcqdrfyw rvssrselnq vdqvgyvtyd ilqcped
```

(SEQ ID NO: 9; Genbank Accession No. NP_004985)

An exemplary amino acid sequence of murine MMP-9 is:

```
  1 mspwqpllla llafgcssaa pyqrqptfvv fpkdlktsnl tdtqlaeayl yrygytraaq 61 mmgekqslrp allmlqkqls lpqtgeldsq tlkairtprc gvpdvgrtqt fkglkwdhhn 121 itywiqnyse dlprdmidda farafavwge vapltftrvy gpeadiviqf gvaehgdgyp 181 fdgkdgllah afppgagvqg dahfdddelw slgkgvvipt yygnsngapc hfpftfegrs 241 ysacttdgrn dgtpwcstta dydkdgkfgf cpserlyteh gngegkpcvf pfifegrsys 301 acttkgrsdg yrwcattany dqdklygfcp trvdatvvgg nsagelcvfp fvflgkqyss 361 ctsdgrrdgr lwcattsnfd tdkkwgfcpd qgyslflvaa hefghalgld hssvpealmy 421 plysylegfp lnkddidgiq ylygrgskpd prppatttte pqptapptmc ptipptaypt 481 vgptvgptga pspgptssps pgptgapspg ptapptagss easteslspa dnpcnvdvfd 541 aiaeiqgalh ffkdgwywkf lnhrgsplqg pfltartwpa lpatldsafe dpqtkrvfff 601 sgrqmwvytg ktvlgprsld klglgpevth vsgllprrlg kallfskgrv wrfdlksqkv 661 dpqsvirvdk efsgvpwnsh difqyqdkay fchgkffwrv sfqnevnkvd hevnqvddvg 721 yvtydllqcp
```

(SEQ ID NO: 10; Genbank Accession No. NP_038627)

An exemplary MMP-9 protein can consist of or comprise the human or mouse MMP-9 amino acid sequence, a sequence that is 80%, 85%, 90%, 95%, 96%, 97%, 98%, or 99% identical to one of these sequences, or a fragment thereof, e.g., a fragment without the signal sequence or pro-domain.

The mRNA sequences of human and murine MMP-9 may be found at GenBank Accession Nos NM_004994 and NM_013599, respectively. The sequences of human and mouse MMP-9 mRNAs are as follows:

```
SEQ ID NO: 11: human MMP-9 mRNA
  1 agacacctct gccctcacca tgagcctctg gcagcccctg gtcctggtgc tcctggtgct 61 gggctgctgc tttgctgccc ccagacagcg ccagtccacc cttgtgctct tccctggaga 121 cctgagaacc aatctcaccg acaggcagct ggcagaggaa tacctgtacc gctatggtta 181 cactcgggtg gcagagatgc gtggagagtc gaaatctctg gggcctgcgc tgctgcttct 241 ccagaagcaa ctgtccctgc ccgagaccgg tgagctggat agcgccacgc tgaaggccat 301 gcgaacccca cggtgcgggg tcccagacct gggcagattc caaacctttg agggcgacct 361 caagtggcac caccacaaca tcacctattg gatccaaaac tactcggaag acttgccgcg 421 ggcggtgatt gacgacgcct tgcccgcgc cttcgcactg tggagcgcgg tgacgccgct 481 caccttcact cgcgtgtaca gccgggacgc agacatcgtc atccagtttg gtgtcgcgga 541 gcacggagac gggtatccct tcgacgggaa ggacgggctc ctggcacacg cctttcctcc 601 tggccccggc attcagggag acgcccattt cgacgatgac gagttgtggt ccctgggcaa 661 gggcgtcgtg gttccaactc ggtttggaaa cgcagatggc gcggcctgcc acttccccctt 721 catcttcgag ggccgctcct actctgcctg caccaccgac ggtcgctccg acggcttgcc 781 ctggtgcagt accacggcca actacgacac cgacgaccgg tttggcttct gccccagcga
```

-continued

```
 841 gagactctac acccaggacg gcaatgctga tgggaaaccc tgccagtttc cattcatctt 901 ccaaggccaa tcctactccg cctgcaccac ggacggtcgc tccgacggct accgctggtg 961 cgccaccacc gccaactacg accgggacaa gctcttcggc ttctgcccga cccgagctga 1021 ctcgacggtg atgggggggca actcggcggg ggagctgtgc gtcttcccct tcactttcct 1081 gggtaaggag tactcgacct gtaccagcga gggccgcgga gatgggcgcc tctggtgcgc 1141 taccacctcg aactttgaca cgacaagaa gtggggcttc tgcccggacc aaggatacag 1201 tttgttcctc gtggcggcgc atgagttcgg ccacgcgctg ggcttagatc attcctcagt 1261 gccggaggcg ctcatgtacc ctatgtaccg cttcactgag gggcccccct tgcataagga 1321 cgacgtgaat ggcatccggc acctctatgg tcctcgccct gaacctgagc cacggcctcc 1381 aaccaccacc acaccgcagc ccacggctcc cccgacggtc tgccccaccg gaccccccac 1441 tgtccacccc tcagagcgcc ccacagctgg ccccacaggt ccccccctcag ctggccccac 1501 aggtcccccc actgctggcc cttctacggc cactactgtg cctttgagtc cggtggacga 1561 tgcctgcaac gtgaacatct tcgacgccat cgcggagatt gggaaccagc tgtatttgtt 1621 caaggatggg aagtactggc gattctctga gggcaggggg agccggccgc agggccccctt 1681 ccttatcgcc gacaagtggc ccgcgctgcc ccgcaagctg gactcggtct ttgaggagcg 1741 gctctccaag aagcttttct tcttctctgg gcgccaggtg tgggtgtaca caggcgcgtc 1801 ggtgctgggc ccgaggcgtc tggacaagct gggcctggga gccgacgtgg cccaggtgac 1861 cggggccctc cggagtggca gggggaagat gctgctgttc agcgggcggc gcctctggag 1921 gttcgacgtg aaggcgcaga tggtggatcc ccggagcgcc agcgaggtgg accggatgtt 1981 ccccggggtg ccttttggaca cgcacgacgt cttccagtac cgagagaaag cctatttctg 2041 ccaggaccgc ttctactggc gcgtgagttc ccggagtgag ttgaaccagg tggaccaagt 2101 gggctacgtg acctatgaca tcctgcagtg ccctgaggac tagggctccc gtcctgcttt 2161 ggcagtgcca tgtaaatccc cactgggacc aaccctgggg aaggagccag tttgccggat 2221 acaaactggt attctgttct ggaggaaagg gaggagtgga ggtgggctgg gccctctctt 2281 ctcacctttg ttttttgttg gagtgtttct aataaacttg gattctctaa cctttaaaaa 2341 aaaaaaaaaa aaaaaaaaa aaaaaaaaaa aaaaaaaaaa aaaaaaa SEQ ID NO: 12: mouse MMP-9 mRNA
   1 ctcaccatga gtccctggca gcccctgctc ctggctctcc tggctttcgg ctgcagctct 61 gctgcccctt accagcgcca gccgactttt gtggtcttcc ccaaagacct gaaaacctcc 121 aacctcacgg acacccagct ggcagaggca tacttgtacc gctatggtta cacccgggcc 181 gcccagatga tgggagagaa gcagtctcta cggccggctt tgctgatgct tcagaagcag 241 ctctcccctgc cccagactgg tgagctggac agccagacac taaaggccat cgaacacca 301 cgctgtggtg tcccagacgt gggtcgattc caaaccttca aaggcctcaa gtgggaccat 361 cataacatca catactggat ccaaaactac tctgaagact gccgcgaga catgatcgat 421 gacgccttcg cgcgcgcctt cgcggtgtgg ggcgaggtgg caccccctcac cttcacccgc 481 gtgtacggac ccgaagcgga cattgtcatc cagtttggtg tcgcggagca cggagacggg 541 tatcccttcg acggcaagga cggccttctg gcacacgcct ttcccccctgg cgccggcgtt 601 cagggagatg cccatttcga cgacgacgag ttgtggtcgc tggcaaagg cgtcgtgatc 661 cccacttact atggaaactc aaatggtgcc ccatgtcact ttcccttcac cttcgaggga 721 cgctcctatt cggcctgcac cacagacggc cgcaacgacg gcacgccttg tgtagcaca 781 acagctgact acgataagga cggcaaattt ggtttctgcc ctagtgagag actctacacg
```

-continued

```
 841 gagcacggca acggagaagg caaaccctgt gtgttcccgt tcatctttga gggccgctcc
 901 tactctgcct gcaccactaa aggccgctcg gatggttacc gctggtgcgc caccacagcc
 961 aactatgacc aggataaact gtatggcttc tgccctaccc gagtggacgc gaccgtagtt
1021 gggggcaact cggcaggaga gctgtgcgtc ttccccttcg tcttcctggg caagcagtac
1081 tcttcctgta ccagcgacgg ccgcagggat gggcgcctct ggtgtgcgac cacatcgaac
1141 ttcgacactg acaagaagtg gggtttctgt ccagaccaag ggtacagcct gttcctggtg
1201 gcagcgcacg agttcggcca tgcactgggc ttagatcatt ccagcgtgcc ggaagcgctc
1261 atgtacccgc tgtatagcta cctcgagggc ttccctctga ataaagacga catagacggc
1321 atccagtatc tgtatggtcg tggctctaag cctgacccaa ggcctccagc caccaccaca
1381 actgaaccac agccgacagc acctcccact atgtgtccca ctatacctcc cacggcctat
1441 cccacagtgg gccccacggt tggccctaca ggcgcccct cacctggccc cacaagcagc
1501 ccgtcacctg ccctacagg cgcccccctca cctggcccta cagcgccccc tactgcgggc
1561 tcttctgagg cctctacaga gtctttgagt ccggcagaca atccttgcaa tgtggatgtt
1621 tttgatgcta ttgctgagat ccagggcgct ctgcatttct tcaaggacgg ttggtactgg
1681 aagttcctga atcatagagg aagcccatta cagggcccct tccttactgc ccgcacgtgg
1741 ccagccctgc ctgcaacgct ggactccgcc tttgaggatc cgcagaccaa gagggttttc
1801 ttcttctctg gacgtcaaat gtgggtgtac acaggcaaga ccgtgctggg ccccaggagt
1861 ctggataagt tgggtctagg cccagaggta acccacgtca gcgggcttct cccgcgtcgt
1921 ctcgggaagg ctctgctgtt cagcaagggg cgtgtctgga gattcgactt gaagtctcag
1981 aaggtggatc cccagagcgt cattcgcgtg gataaggagt tctctggtgt gccctggaac
2041 tcacacgaca tcttccagta ccaagacaaa gcctatttct gccatggcaa attcttctgg
2101 cgtgtgagtt ccaaaatga ggtgaacaag gtggaccatg aggtgaacca ggtggacgac
2161 gtgggctacg tgacctacga cctcctgcag tgcccttgaa ctagggctcc ttctttgctt
2221 caaccgtgca gtgcaagtct ctagagacca ccaccaccac caccacacac aaaccccatc
2281 cgagggaaag gtgctagctg gccaggtaca gactggtgat ctcttctaga gactgggaag
2341 gagtggaggc aggcagggct ctctctgccc accgtccttt cttgttggac tgtttctaat
2401 aaacacggat ccccaacctt ttccagctac tttagtcaat cagcttatct gtagttgcag
2461 atgcatccga gcaagaagac aactttgtag ggtggattct gacctttat ttttgtgtgg
2521 cgtctgagaa ttgaatcagc tggcttttgt gacaggcact tcaccggcta aaccacctct
2581 cccgactcca gccctttat ttattatgta tgaggttatg ttcacatgca tgtatttaac
2641 ccacagaatg cttactgtgt gtcgggcgcg gctccaaccg ctgcataaat attaaggtat
2701 tcagttgccc ctactggaag gtattatgta actatttctc tcttacattg gagaacacca
2761 ccgagctatc cactcatcaa acatttattg agagcatccc tagggagcca ggctctctac
2821 tgggcgttag ggacagaaat gttggttctt ccttcaagga ttgctcagag attctccgtg
2881 tcctgtaaat ctgctgaaac cagaccccag actcctctct ctcccgagag tccaactcac
2941 tcactgtggt tgctggcagc tgcagcatgc gtatacagca tgtgtgctag agaggtagag
3001 ggggtctgtg cgttatggtt caggtcagac tgtgtcctcc aggtgagatg acccctcagc
3061 tggaactgat ccaggaagga taaccaagtg tcttcctggc agtctttttt aaataaatga
3121 ataaatgaat atttacttaa aaaaaaaaaa aaaaaaaaa aaaaaaaaa aaaaaaaaaa
3181 aaaaa
```

An exemplary MMP-9 gene can consist of or comprise the human or mouse MMP-9 mRNA sequence, a sequence that is 80%, 85%, 90%, 95%, 96%, 97%, 98%, or 99% identical to one of these sequences, or a fragment thereof.

Methods of evaluating levels of gene expression and protein activity, as well as evaluating the amounts of gene or protein molecules in a sample, are well-known in the art. Exemplary methods by which the expression of the MMP-14, MMP-2 or MMP-9 genes or the activity of the MMP-14, MMP-2 or MMP-9 proteins may be determined are further described below.

In certain embodiments, a method of evaluating the expression and/or activity of MMP-14, MMP-2 and/or MMP-9 in a cell may comprise a) determining in the cell the level of expression and/or activity of MMP-14, MMP-2 and/or MMP-9. The method may in certain embodiments further comprise calculating a ratio of the expression and/or activity level of two of MMP-14, MMP-2 and/or MMP-9 from the determined levels.

The above-described method may further comprise b) comparing the determined level of expression and/or activity of, or ratio of the level of expression and/or activity of two of, MMP-14, MMP-2 and/or MMP-9 with at least one reference set of levels of expression and/or activity of, or ratio of, MMP-14, MMP-2 and/or MMP-9, wherein the reference set indicates the state of the cell associated with the particular level of expression and/or activity of, or ratio of, MMP-14, MMP-2 and/or MMP-9.

Comparison to a reference set or profile is particularly useful in applications of the above-described methods, for example, when they are used in methods for diagnosing and prognosing cancer in a subject, or for screening candidate therapeutics for their efficacy in treating cancer or for stratifying patients based on their risk for or stage of cancer or for selecting a therapy for a patient having or suspected of having cancer. In certain preferred embodiments, the cancer is selected from the group consisting of: osteotropic cancer, breast cancer, lung cancer, colon cancer and prostate cancer.

Comparison of the expression and/or activity level of, or ratio of the level of expression and/or activity of two of, MMP-14, MMP-2 and/or MMP-9 with reference expression and/or activity levels, or ratios, e.g., expression and/or activity levels in diseased cells of a subject having cancer or in normal counterpart cells, is preferably conducted using computer systems. In one embodiment, expression and/or activity levels are obtained in two cells and these two sets of expression and/or activity levels are introduced into a computer system for comparison. In a preferred embodiment, one set of expression and/or activity levels is entered into a computer system for comparison with values that are already present in the computer system, or in computer-readable form that is then entered into the computer system.

In one embodiment, the invention provides computer readable forms of the gene expression or protein activity profile data of the invention, or of values corresponding to the level of expression and/or activity of, or ratios of the level of expression and/or activity of, MMP-14, MMP-2 and/or MMP-9. The values may be, for example, mRNA expression levels or AQUA™ scores. The values may also be mRNA levels, AQUA™ scores, or other measure of gene expression and/or protein activity normalized relative to a reference gene whose expression or protein whose activity is constant in numerous cells under numerous conditions. In other embodiments, the values in the computer are ratios of, or differences between, normalized or non-normalized levels in different samples.

The profile data may be in the form of a table, such as an Excel table. The data may be alone, or it may be part of a larger database, e.g., comprising other profiles. For example, the profile data of the invention may be part of a public database. The computer readable form may be in a computer. In another embodiment, the invention provides a computer displaying the profile data.

In one embodiment, the invention provides methods for determining the similarity between the level of expression and/or activity of, or ratio of the level of expression and/or activity of two of, MMP-14, MMP-2 and/or MMP-9 in a first cell, e.g., a cell of a subject, and that in a second cell, comprising obtaining the level of expression and/or activity of, or ratio of the level of expression and/or activity of two of, MMP-14, MMP-2 and/or MMP-9 in a first cell and entering these values into a computer comprising a database including records comprising values corresponding to levels of expression and/or activity of, or ratio of the level of expression and/or activity of two of, MMP-14, MMP-2 and/or MMP-9 in a second cell, and processor instructions, e.g., a user interface, capable of receiving a selection of one or more values for comparison purposes with data that is stored in the computer. The computer may further comprise a means for converting the comparison data into a diagram or chart or other type of output.

In another embodiment, at least one value representing the expression and/or activity level of, or ratio of the level of expression and/or activity of two of, MMP-14, MMP-2 and/or MMP-9 is entered into a computer system, comprising one or more databases with reference expression and/or activity levels, or ratios, obtained from more than one cell. For example, a computer may comprise expression and/or activity and/or ratio data of diseased and normal cells. Instructions are provided to the computer, and the computer is capable of comparing the data entered with the data in the computer to determine whether the data entered is more similar to that of a normal cell or of a diseased cell.

In another embodiment, the computer comprises values of expression and/or activity levels, or ratios, in cells of subjects at different stages of cancer and the computer is capable of comparing expression and/or activity and/or ratio data entered into the computer with the data stored, and produce results indicating to which of the expression and/or activity and/or ratio profiles in the computer, the one entered is most similar, such as to determine the stage of cancer in the subject.

In yet another embodiment, the reference expression and/or activity and/or ratio profiles in the computer are expression and/or activity and/or ratio profiles from cells of one or more subjects having cancer, which cells are treated in vivo or in vitro with a drug used for therapy of cancer. Upon entering of expression and/or activity and/or ratio data of a cell of a subject treated in vitro or in vivo with the drug, the computer is instructed to compare the data entered to the data in the computer, and to provide results indicating whether the expression and/or activity data input into the computer are more similar to those of a cell of a subject that is responsive to the drug or more similar to those of a cell of a subject that is not responsive to the drug. Thus, the results indicate whether the subject is likely to respond to the treatment with the drug (e.g., more likely to respond than not, e.g., greater than 50% likelihood of responding) or unlikely to respond to it (e.g., greater than 50% likelihood of not responding).

In one embodiment, the invention provides systems comprising a means for receiving expression and/or activity and/or ratio data for one or a plurality of genes and/or protein; a means for comparing the expression and/or activity and/or ratio data from each of said one or plurality of genes and/or proteins to a common reference frame; and a means for presenting the results of the comparison. A system may further comprise a means for clustering the data.

In another embodiment, the invention provides computer programs for analyzing expression and/or activity and/or ratio data comprising (a) a computer code that receives as input expression and/or activity and/or ratio data for at least one gene and (b) a computer code that compares said expression and/or activity and/or ratio data from each gene to a common reference frame.

The invention also provides machine-readable or computer-readable media including program instructions for performing the following steps: (a) comparing at least one value corresponding to the expression and/or activity level of, or ratio of the level of expression and/or activity of two of, MMP-14, MMP-2 and/or MMP-9 in a query cell with a database including records comprising reference expression and/or activity and/or ratio data of one or more reference cells and an annotation of the type of cell; and (b) indicating to which cell the query cell is most similar based on similarities of expression and/or activity profiles and/or ratios. The reference cells may be cells from subjects at different stages of cancer. The reference cells may also be cells from subjects responding or not responding to a particular drug treatment and optionally incubated in vitro or in vivo with the drug.

The reference cells may also be cells from subjects responding or not responding to several different treatments, and the computer system indicates a preferred treatment for the subject. Accordingly, the invention provides methods for selecting a therapy for a patient having cancer; the methods comprising: (a) providing the level of expression and/or activity of, or ratio of the level of expression and/or activity of two of, MMP-14, MMP-2 and/or MMP-9 in a diseased cell of the patient; (b) providing a plurality of reference profiles, each associated with a therapy; and (c) selecting the reference profile most similar to the subject expression and/or activity profile, or ratio, to thereby select a therapy for said patient. In a preferred embodiment step (c) is performed by a computer. The most similar reference profile or ratio may be selected by weighing a comparison value of the plurality using a weight value associated with the corresponding expression and/or activity data, or ratio.

A computer readable medium may further comprise a pointer to a descriptor of a stage of cancer or to a treatment for cancer.

In operation, the means for receiving expression and/or activity data, or ratios, the means for comparing the expression and/or activity data, or ratios, the means for presenting, the means for normalizing, and the means for clustering within the context of the systems of the present invention may involve a programmed computer with the respective functionalities described herein, implemented in hardware or hardware and software; a logic circuit or other component of a programmed computer that performs the operations specifically identified herein, dictated by a computer program; or a computer memory encoded with executable instructions representing a computer program that may cause a computer to function in the particular fashion described herein.

Those skilled in the art will understand that the systems and methods of the present invention may be applied to a variety of systems, including IBM®-compatible personal computers running MS-DOS® or Microsoft WINDOWS®. In an exemplary implementation, expression profiles are compared using a method described in U.S. Pat. No. 6,203,987. A user first loads expression profile or ratio data into the computer system. Geneset profile or ratio definitions are loaded into the memory from the storage media or from a remote computer, preferably from a dynamic geneset database system, through the network. Next the user causes execution of projection software which performs the steps of converting expression and/or activity profile, or ratio, to projected expression and/or activity profiles or ratios. The projected expression and/or activity profiles, or ratios, are then displayed.

In yet another exemplary implementation, a user first leads a projected profile or ratio into the memory. The user then causes the loading of a reference profile or ratio into the memory. Next, the user causes the execution of comparison software which performs the steps of objectively comparing the profiles or ratios.

Exemplary diagnostic tools and assays are set forth below, which comprise the above-described methodology.

In one embodiment, the invention provides methods for determining whether a subject has or is likely to develop cancer, comprising determining the level of expression and/or activity of MMP-14, MMP-2 and/or MMP-9 in a cell of the subject and comparing these levels of expression and/or activity, or ratio of the levels, with the levels of expression of or ratios of MMP-14, MMP-2 and/or MMP-9 in a diseased cell of a subject known to have cancer, such that a similar level of expression and/or activity of, or ratio of, MMP-14, MMP-2 and/or MMP-9 is indicative that the subject has or is likely to develop cancer or at least a symptom thereof. In a preferred embodiment, the cell is essentially of the same type as that which is diseased in the subject.

In another embodiment the expression and/or activity profiles, or ratios, of genes in the cell may be used to confirm that a subject has a specific type of cancer, and in particular, that the subject does not have a related disease or disease with similar symptoms. This may be important, in particular, in designing an optimal therapeutic regimen for the subject. It has been described in the art that expression and/or activity profiles or ratios may be used to distinguish one type of disease from a similar disease. For example, two subtypes of non-Hodgkin's lymphomas, one of which responds to current therapeutic methods and the other one which does not, could be differentiated by investigating 17,856 genes in specimens of patients suffering from diffuse large B-cell lymphoma (Alizadeh et al. *Nature* (2000) 405:503). Similarly, subtypes of cutaneous melanoma were predicted based on profiling 8150 genes (Bittner et al. *Nature* (2000)-406:536). In this case, features of the highly aggressive metastatic melanomas could be recognized. Numerous other studies comparing expression and/or activity profiles or ratios of cancer cells and normal cells have been described, including studies describing expression profiles distinguishing between highly and less metastatic cancers and studies describing new subtypes of diseases, e.g., new tumor types (see, e.g., Perou et al. (1999) *PNAS* 96: 9212; Perou et al. (2000) *Nature* 606:747; Clark et al. (2000) *Nature* 406:532; Alon et al. (1999) *PNAS* 96:6745; Golub et al. (1999) *Science* 286:531). Such distinction is known in the art as "differential diagnosis".

In yet another embodiment, the invention provides methods for determining the stage of cancer, i.e., for "staging" cancer. It is thought that the level of expression and/or activity of, or ratio of the level of expression and/or activity of two of, MMP-14, MMP-2 and/or MMP-9 changes with the stage of the disease. This could be confirmed, e.g., by analyzing the level of expression and/or activity of, or ratio of the level of expression and/or activity of two of, MMP-14, MMP-2 and/or MMP-9 in subjects having cancer at different stages, as determined by traditional methods. For example, the expression profile of a diseased cell in subjects at different stages of the disease may be determined as described herein. Then, to determine the stage of cancer in a subject, the level of expression and/or activity of, or ratio of the level of expression and/or activity of two of, MMP-14, MMP-2 and/or MMP-9, which varies with the stage of the disease, is determined. A similar level of expression and/or activity of, or ratio of the level of expression and/or activity of two of, MMP-14, MMP-2 and/or MMP-9 between that in a subject and that in a reference profile of a particular stage of the disease, indicates that the disease of the subject is at the particular stage.

Similarly, the methods may be used to determine the stage of the disease in a subject undergoing therapy, and thereby determine whether the therapy is effective. Accordingly, in one embodiment, the level of expression and/or activity of, or ratio of the level of expression and/or activity of two of, MMP-14, MMP-2 and/or MMP-9 is determined in a subject before the treatment and several times during the treatment. For example, a sample of RNA may be obtained from the subject and analyzed before the beginning of the therapy and every 12, 24, 36, 48, 60, or 72 hours during the therapy. Alternatively or in addition, samples may be analyzed once a week or once a month or once a year, e.g., over the course of the therapy. Changes in expression and/or activity levels of, or ratios of the level of expression and/or activity of two of, MMP-14, MMP-2 and/or MMP-9 over time and relative to diseased cells and normal cells will indicate whether the therapy is effective.

Further, the methods may be used to determine the stage of the disease in a subject after undergoing therapy, e.g., and thereby determine whether the therapy was effective and/or whether the disease is re-developing (e.g., whether the disease has returned, e.g., whether the disease has relapsed). Accordingly, in one embodiment, the level of expression and/or activity of, or ratio of the level of expression and/or activity of two of, MMP-14, MMP-2 and/or MMP-9 is determined in a subject during and/or immediately after the treatment and/or several times after the treatment. For example, a sample of RNA may be obtained from the subject and analyzed at the end of the therapy and once a week, once a month or once a year, e.g., for the next 1, 2, 3, 4, or 5 years. Changes in expression and/or activity levels of, or ratios of the level of expression and/or activity of two of, MMP-14, MMP-2 and/or MMP-9 over time and relative to diseased cells and normal cells can indicate whether the therapy was effective, and/or whether the disease is re-developing.

In yet another embodiment, the invention provides methods for determining the likelihood of success of a particular therapy in a subject having cancer. In one embodiment, a subject is started on a particular therapy, and the effectiveness of the therapy is determined, e.g., by determining the level of expression and/or activity of, or ratio of the level of expression and/or activity of two of, MMP-14, MMP-2 and/or MMP-9 in a cell of the subject. A normalization of the level of expression and/or activity of, or ratio of the level of expression and/or activity of two of, MMP-14, MMP-2 and/or MMP-9, i.e., a change in the expression and/or activity of level, or ratio, of the gene(s) such that their level of expression and/or activity or ratio, resembles more that of a non diseased cell, indicates that the treatment should be effective in the subject.

Prediction of the outcome of a treatment in a subject may also be undertaken in vitro. In one embodiment, cells are obtained from a subject to be evaluated for responsiveness to the treatment, and incubated in vitro with the therapeutic drug. The level of expression and/or activity of MMP-14, MMP-2 and/or MMP-9 is then measured in the cells and these values are compared to the level of expression and/or activity of MMP-14, MMP-2 and/or MMP-9 in a cell which is the normal counterpart cell of a diseased cell. The level of expression and/or activity may also be compared to that in a normal-cell. In certain embodiments, the ratio of the level of expression and/or activity of two of MMP-14, MMP-2 and/or MMP-9 may be used. The comparative analysis is preferably conducted using a computer comprising a database of expression and/or activity profiles, or ratios, as described above. A level of expression and/or activity of, or ratio of the level of expression and/or activity of two of, MMP-14, MMP-2 and/or MMP-9 in the cells of the subject after incubation with the drug that is similar to their level of expression and/or activity, or ratio of the level of expression and/or activity, in a normal cell and different from that in a diseased cell is indicative that it is likely that the subject will respond positively to a treatment with the drug. On the contrary, a level of expression and/or activity of, or ratio of the level of expression and/or activity of two of, MMP-14, MMP-2 and/or MMP-9 in the cells of the subject after incubation with the drug that is similar to their level of expression and/or activity, or ratio, in a diseased cell and different from that in a normal cell is indicative that it is likely that the subject will not respond positively to a treatment with the drug.

Since it is possible that a drug does not act directly on the diseased cells, but is, e.g., metabolized, or acts on another cell which then secretes a factor that will effect the diseased cells, the above assay may also be conducted in a tissue sample of a subject, which contains cells other than the diseased cells. For example, a tissue sample comprising diseased cells is obtained from a subject; the tissue sample is incubated with the potential drug; optionally one or more diseased cells are isolated from the tissue sample, e.g., by microdissection or Laser Capture Microdissection (LCM, see infra); and the expression level of MMP-14, MMP-2 and/or MMP-9 is examined.

Provided also are methods for selecting a therapy for cancer for a patient from a selection of several different treatments. Certain subjects having cancer may respond better to one type of therapy than another type of therapy. In a preferred embodiment, the method comprises comparing the expression and/or activity level of, or ratio of the level of expression and/or activity of two of, MMP-14, MMP-2 and/or MMP-9 in the patient with that in cells of subjects treated in vitro or in vivo with one of several therapeutic drugs, which subjects are responders or non responders to one of the therapeutic drugs, and identifying the cell which has the most similar level of expression and/or activity of, or ratio of the level of expression and/or activity of two of, MMP-14, MMP-2 and/or MMP-9 to that of the patient, to thereby identify a therapy for the patient. The method may further comprise administering the therapy identified to the subject.

Methods of Evaluating the Expression and/or Activity of MMP-14, MMP-2 and/or MMP-9

The methods of diagnosing and prognosing cancer by evaluating the level of expression and/or activity of, or ratio of the level of expression and/or activity of two of, MMP-14, MMP-2 and/or MMP-9 and methods of screening candidate therapeutic agents which modulate the expression and/or activity of, or ratio of the level of expression and/or activity of two of, MMP-14, MMP-2 and/or MMP-9, described above, comprise determining the level of expression and/or activity of, or ratio of the level of expression and/or activity of two of, MMP-14, MMP-2 and/or MMP-9.

Methods for determining the expression level and ultimately the activity of MMP-14, MMP-2 and/or MMP-9 are well known in the art (and the ratio of such levels may be determined from the determined levels). For example, the expression level of MMP-14, MMP-2 and/or MMP-9 can be determined by reverse transcription-polymerase chain reaction (RT-PCR); dotblot analysis; Northern blot analysis and in situ hybridization. Alternatively, the level of MMP-14, MMP-2 and/or MMP-9 can be analyzed using an appropriate antibody. In certain embodiments, the amounts of MMP-14, MMP-2 and/or MMP-9 is determined using antibodies against MMP-14, MMP-2 and/or MMP-9.

In certain embodiments, the level of expression of MMP-14, MMP-2 and/or MMP-9 is determined by determining its AQUA™ score, e.g., by using the AQUA™ automated pathology system. AQUA™ (for Automated Quantitative Analysis) is a method of analysis of absolute measurement of protein expression in situ. This method allows measurements of protein expression within sub-cellular compartments that results in a number directly proportional to the number of molecules expressed per unit area. For example, to measure nuclear estrogen receptor (ER), the tissue is "masked" using keratin in one channel to normalize the area of tumor and to remove the stromal and other non-tumor material from analysis. Then an image is taken using DAPI to define a nuclear compartment. The pixels within the mask and within the DAPI-defined compartment are defined as nuclear. The intensity of expression of ER is then measured using a third channel. The intensity of that subset of pixels divided by the number of pixels (to normalize the area from spot to spot) to give an AQUA™ score. This score is directly proportional to the number of molecules of ER per unit area of tumor, as assessed by a standard curve of cell lines with known levels of ER protein expression. This method, including details of out-of-focus light subtraction imaging methods, is described in detail in a Nature Medicine paper (Camp, R. L., Chung, G. G. & Rimm, D. L. Automated subcellular localization and quantification of protein expression in tissue microarrays. *Nat Med* 8, 1323-7 (2002)), as well as U.S. Ser. No. 10/062,308, filed Feb. 1, 2002, both of which reference are incorporated herein by their entireties.

In other embodiments, methods of detecting the level of expression of MMP-14, MMP-2 and/or MMP-9 may comprise the use of a microarray. Arrays are often divided into microarrays and macroarrays, where microarrays have a much higher density of individual probe species per area. Microarrays may have as many as 1000 or more different probes in a 1 cm² area. There is no concrete cut-off to demarcate the difference between micro- and macroarrays, and both types of arrays are contemplated for use with the invention.

Microarrays are known in the art and generally consist of a surface to which probes that correspond in sequence to gene products (e.g., cDNAs, mRNAs, oligonucleotides) are bound at known positions. In one embodiment, the microarray is an array (e.g., a matrix) in which each position represents a discrete binding site for a product encoded by a gene (e.g., a protein or RNA), and in which binding sites are present for products of most or almost all of the genes in the organism's genome. In certain embodiments, the binding site or site is a nucleic acid or nucleic acid analogue to which a particular cognate cDNA can specifically hybridize. The nucleic acid or analogue of the binding site may be, e.g., a synthetic oligomer, a full-length cDNA, a less-than full length cDNA, or a gene fragment.

Although in certain embodiments the microarray contains binding sites for products of all or almost all genes in the target organism's genome, such comprehensiveness is not necessarily required. Usually the microarray will have binding sites corresponding to at least 100, 500, 1000, 4000 genes or more. In certain embodiments, arrays will have anywhere from about 50, 60, 70, 80, 90, or even more than 95% of the genes of a particular organism represented. The microarray typically has binding sites for genes relevant to testing and confirming a biological network model of interest. Several exemplary human microarrays are publicly available.

The probes to be affixed to the arrays are typically polynucleotides. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, which result in amplification of unique fragments (e.g., fragments that do not share more than 10 bases of contiguous identical sequence with any other fragment on the microarray). Computer programs are useful in the design of primers with the required specificity and optimal amplification properties. See, e.g., Oligo pl version 5.0 (National Biosciences). In an alternative embodiment, the binding (hybridization) sites are made from plasmid or phage clones of genes, cDNAs (e.g., expressed sequence tags), or inserts therefrom (Nguyen et al., 1995, *Genomics* 29:207-209).

A number of methods are known in the art for affixing the nucleic acids or analogues to a solid support that makes up the array (Schena et al., 1995, *Science* 270:467-470; DeRisi et al., 1996, *Nature Genetics* 14:457-460; Shalon et al., 1996, *Genome Res.* 6:639-645; and Schena et al., 1995, *Proc. Natl. Acad. Sci. USA* 93:10539-11286).

Another method for making microarrays is by making high-density oligonucleotide arrays (Fodor et al., 1991, *Science* 251:767-773; Pease et al., 1994, *Proc. Natl. Acad. Sci. USA* 91:5022-5026; Lockhart et al., 1996, *Nature Biotech* 14:1675; U.S. Pat. Nos. 5,578,832; 5,556,752; and 5,510,270; Blanchard et al., 1996, 11: 687-90).

Other methods for making microarrays, e.g., by masking (Maskos and Southern, 1992, *Nuc. Acids Res.* 20:1679-1684), may also be used. In principal, any type of array, for example, dot blots on a nylon hybridization-membrane (see Sambrook et al., Molecular Cloning—A Laboratory Manual (2nd Ed.), Vol. 1-3, Cold Spring Harbor Laboratory, Cold Spring Harbor, N.Y., 1989), could be used, as will be recognized by those of skill in the art.

The nucleic acids to be contacted with the microarray may be prepared in a variety of ways, and may include nucleotides of the subject invention. Such nucleic acids are often labeled fluorescently. Nucleic acid hybridization and wash conditions are chosen so that the population of labeled nucleic acids will specifically hybridize to appropriate, complementary nucleic acids affixed to the matrix. Non-specific binding of the labeled nucleic acids to the array can be decreased by treating the array with a large quantity of non-specific DNA—a so-called "blocking" step.

When fluorescently labeled probes are used, the fluorescence emissions at each site of a transcript array may be detected by scanning confocal laser microscopy. When two fluorophores are used, a separate scan, using the appropriate excitation line, is carried out for each of the two fluorophores used. Fluorescent microarray scanners are commercially available from Affymetrix, Packard BioChip Technologies, BioRobotics and many other suppliers. Signals are recorded, quantitated and analyzed using a variety of computer software.

According to the method of the invention, the relative abundance of an mRNA in two cells or cell lines is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2

(twice as abundant), 3 (three times as abundant) or 5 (five times as abundant) is scored as a perturbation. Present detection methods allow reliable detection of difference of an order of about 2-fold to about 5-fold, but more sensitive methods are expected to be developed.

In addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In certain embodiments, the data obtained from such experiments reflects the relative expression of each gene represented in the microarray. Expression levels in different samples and conditions may now be compared using a variety of statistical methods.

In certain embodiments, the cell comprises a tissue sample, which may be present on a tissue microarray. For example, paraffin-embedded formalin-fixed specimens may be prepared, and punch "biopsy" cores taken from separate areas of the specimens. Each core may be arrayed into a separate recipient block, and sections cut and processed as previously described, for example, in Konenen, J. et al., Tissue microarrays for high-throughput molecular profiling of tumor specimens, (1987) *Nat. Med.* 4:844-7 and Chung, G. G. et al., *Clin. Cancer Res.* (In Press).

In other embodiments, the cell comprises a cell culture pellet, which may be present on a cell culture pellet microarray.

In certain embodiments, it is sufficient to determine the expression of one or only a few genes, as opposed to hundreds or thousands of genes. Although microarrays may be used in these embodiments, various other methods of detection of gene expression are available. This section describes a few exemplary methods for detecting and quantifying mRNA or polypeptide encoded thereby. Where the first step of the methods includes isolation of mRNA from cells, this step may be conducted as described above. Labeling of one or more nucleic acids may be performed as described above.

In one embodiment, mRNA obtained from a sample is reverse transcribed into a first cDNA strand and subjected to PCR, e.g., RT-PCR. House keeping genes, or other genes whose expression does not vary may be used as internal controls and controls across experiments. Following the PCR reaction, the amplified products may be separated by electrophoresis and detected. By using quantitative PCR, the level of amplified product will correlate with the level of RNA that was present in the sample. The amplified samples may also be separated on an agarose or polyacrylamide gel, transferred onto a filter, and the filter hybridized with a probe specific for the gene of interest. Numerous samples may be analyzed simultaneously by conducting parallel PCR amplification, e.g., by multiplex PCR.

"Dot blot" hybridization has gained wide-spread use, and many versions were developed (see, e.g., M. L. M. Anderson and B. D. Young, in *Nucleic Acid Hybridization—A Practical Approach*, B. D. Hames and S. J. Higgins, Eds., IRL Press, Washington D.C., Chapter 4, pp. 73-111, 1985).

In another embodiment, mRNA levels is determined by dot blot analysis and related methods (see, e.g., G. A. Beltz et al., in *Methods in Enzymology*, Vol. 100, Part B, R. Wu, L. Grossmam, K. Moldave, Eds., Academic Press, New York, Chapter 19, pp. 266-308, 1985). In one embodiment, a specified amount of RNA extracted from cells is blotted (i.e., non-covalently bound) onto a filter, and the filter is hybridized with a probe of the gene of interest. Numerous RNA samples may be analyzed simultaneously, since a blot may comprise multiple spots of RNA. Hybridization is detected using a method that depends on the type of label of the probe. In another dot blot method, one or more probes for a biomarker are attached to a membrane, and the membrane is incubated with labeled nucleic acids obtained from and optionally derived from RNA of a cell or tissue of a subject. Such a dot blot is essentially an array comprising fewer probes than a microarray.

Another format, the so-called "sandwich" hybridization, involves covalently attaching oligonucleotide probes to a solid support and using them to capture and detect multiple nucleic acid targets (see, e.g., M. Ranki et al. (1983) *Gene*, 21:77-85; A. M. Palva, et al, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R. B. Wallace et al. (1979) *Nucleic Acid Res.* 6, 11:3543; and B. J. Connor et al. (1983) *PNAS* 80:278-282). Multiplex versions of these formats are called "reverse dot blots."

mRNA levels may also be determined by Northern blots. Specific amounts of RNA are separated by gel electrophoresis and transferred onto a filter which is then hybridized with a probe corresponding to the gene of interest. This method, although more burdensome when numerous samples and genes are to be analyzed, provides the advantage of being very accurate.

Another method for high throughput analysis of gene expression is the serial analysis of gene expression (SAGE) technique, first described in Velculescu et al. (1995) *Science* 270, 484-487. Among the advantages of SAGE is that it has the potential to provide detection of all genes expressed in a given cell type, provides quantitative information about the relative expression of such genes, permits ready comparison of gene expression of genes in two cells, and yields sequence information that may be used to identify the detected genes. Thus far, SAGE methodology has proved itself to reliably detect expression of regulated and nonregulated genes in a variety of cell types (Velculescu et al. (1997) *Cell* 88, 243-251; Zhang et al. (1997) *Science* 276, 1268-1272 and Velculescu et al. (1999) *Nat. Genet.* 23, 387-388).

Techniques for producing and probing nucleic acids are further described, for example, in Sambrook et al., *Molecular Cloning: A Laboratory Manual* (New York, Cold Spring Harbor Laboratory, 1989).

Alternatively, the level of expression of MMP-14, MMP-2 and/or MMP-9 is determined by in situ hybridization. In one embodiment, a tissue sample is obtained from a subject, the tissue sample is sliced, and in situ hybridization is performed according to methods known in the art, to determine the level of expression of MMP-14, MMP-2 and/or MMP-9.

In other methods, the level of expression of MMP-14, MMP-2 and/or MMP-9 is detected by measuring the level of protein encoded by the MMP-14, MMP-2 and/or MMP-9 gene. This may be done, e.g., by immunoprecipitation, ELISA, or immunohistochemistry using an agent, e.g., an antibody, that specifically detects the protein encoded by the gene. Other techniques include Western blot analysis. Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which may be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, may be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In the case of polypeptides which are secreted from cells, the level of expression of these polypeptides may be measured in biological fluids.

The above-described methods may be performed using cells grown in cell culture, or on cell or tissue specimens from a subject. Specimens may be obtained from an individual to be tested using either "invasive" or "non-invasive" sampling means. A sampling means is said to be "invasive" if it involves the collection of nucleic acids from within the skin or organs of an animal (including, especially, a murine, a human, an ovine, an equine, a bovine, a porcine, a canine, or a feline animal). Examples of invasive methods include blood collection, semen collection, needle biopsy, pleural aspiration, umbilical cord biopsy, etc. Examples of such methods are discussed by Kim, C. H. et al. (1992) *J. Virol.* 66:3879-3882; Biswas, B. et al. (1990) *Annals NY Acad. Sci.* 590:582-583; Biswas, B. et al. (1991) *J. Clin. Microbiol.* 29:2228-2233. It is also possible to obtain a cell sample from a subject, and then to enrich it in the desired cell type. For example, cells may be isolated from other cells using a variety of techniques, such as isolation with an antibody binding to an epitope on the cell surface of the desired cell type.

In certain embodiments, a single cell is used in the analysis. It is also possible to obtain cells from a subject and culture the cells in vitro, such as to obtain a larger population of cells from which RNA may be extracted. Methods for establishing cultures of non-transformed cells, i.e., primary cell cultures, are known in the art.

When analyzing from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA and proteins in the tissue and cells may quickly become degraded. Accordingly, in a preferred embodiment, the cells obtained from a subject are snap frozen as soon as possible.

Agents that Bind MMP-14, MMP-2 and/or MMP-9

Provided also are agents that bind MMP-14, MMP-2 and/or MMP-9 polypeptides. Preferably, such agents are anti-MMP-14, MMP-2 and/or MMP-9 antibodies or antigen-binding fragments thereof, including polyclonal and monoclonal antibodies, prepared according to conventional methodology. Antibodies and antigen-binding fragments thereof that bind MMP-14, MMP-2 and/or MMP-9 biomarkers are useful for determining MMP-14, MMP-2 and/or MMP-9 protein levels.

Antibodies and antigen-binding fragments thereof that bind MMP-14, MMP-2 and/or MMP-9 and are useful for determining MMP-14, MMP-2 and/or MMP-9 levels, include but are not limited to: antibodies or antigen-binding fragments thereof that bind specifically to a MMP-14, MMP-2 and/or MMP-9 or fragments or analogs thereof.

Significantly, as is well-known in the art, only a small portion of an antibody molecule, the paratrope, is involved in the binding of the antibody to its epitope (see, in general, Clark, W. R. (1986) The Experimental Foundations of Modem Immunology, Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, W. R. (1986) The Experimental Foundations of Modem Immunology, Wiley & Sons, Inc., New York; Roitt, I. (1991) Essential Immunology, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816, 567, 5,225,539, 5,585,089, 5,693,762 and 5,859,205.

Fully human monoclonal antibodies also can be prepared by immunizing mice transgenic for large portions of human immunoglobulin heavy and light chain loci. Following immunization of these mice (e.g., XENOMOUSE™ (Abgenix), HUMAB-MOUSE™ (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to MMP-14, MMP-2 and/or MMP-9 polypeptides and nucleic acids. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to MMP-14, MMP-2 and/or MMP-9 molecules. This process can be repeated through several cycles of reselection of phage that bind to the MMP-14, MMP-2 and/or MMP-9 molecules. Repeated rounds lead to enrichment of phage bearing particular sequences. DNA sequence analysis can be conducted to identify the sequences of the expressed polypeptides. The minimal linear portion of the sequence that binds to the MMP-14, MMP-2 and/or MMP-9 molecules can be determined. One can repeat the procedure using a biased library containing inserts containing part of all of the minimal linear portion plus one or more additional degenerate residues upstream or downstream thereof. Yeast two-hybrid screening methods also may be used to identify polypeptides that bind to the MMP-14, MMP-2 and/or MMP-9 molecules. Thus, MMP-14, MMP-2 and/or MMP-9 molecules can be used to screen peptide libraries, including phage display libraries, to identify and select peptide binding partners of the MMP-14, MMP-2 and/or MMP-9 molecules.

Exemplary MMP-14 binding proteins that may be used either to detect MMP-14 or inhibit MMP-14 also include those M0031-C02, M0031-F01, M0033-H07, M0037-C09, M0037-D01, M0038-E06, M0038-F01, M0038-F08, M0039-H08, M0040-A06, M0040-A11, and M0043-G02. The amino acid sequences of exemplary Fab heavy chain (HC) and light chain (LC) variable regions of these binding proteins, and further descriptions of them and their discovery and production, are provided in pending application U.S. Ser. No. 11/648,423 (US 2007-0217997), which is hereby incorporated by reference herein in its entirety. Other exemplary MMP-14 binding proteins include DX-2400 and DX-2410. DX-2400 and M0038-F01 share HC and LC CDR amino acid sequences.

Exemplary MMP-9 binding proteins that may be used either to detect MMP-9 or inhibit MMP-9 include 539A-M0166-F10 and 539A-M0240-B03. The amino acid sequences of exemplary Fab heavy chain (HC) and light chain (LC) variable regions of these binding proteins, and further descriptions of them and their discovery and production, are provided in pending applications U.S. Ser. No. 61/033,075 and 61/054,938, which are hereby incorporated by reference herein in their entireties.

As detailed herein, the foregoing antibodies and other binding proteins may be used for example to isolate and identify MMP-14, MMP-2 and/or MMP-9 protein, e.g. to detect its expression in tissue samples. The antibodies may be coupled to specific diagnostic labeling agents for imaging of the protein or fragment thereof. Exemplary labels include, but are not limited to, labels which when fused to a MMP-14, MMP-2 and/or MMP-9 molecule produce a detectable fluorescent signal, including, for example, green fluorescent protein (GFP), enhanced green fluorescent protein (EGFP), *Renilla reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED). In another embodiment, a cancer biomarker polypeptide is conjugated to a fluorescent or chromogenic label. A wide variety of fluorescent labels are available from and/or extensively described in the *Handbook of Fluorescent Probes and Research Products* $8^{th}$ Ed. (2001), available from Molecular Probes, Eugene, Oreg., as well as many other manufacturers.

In other embodiments, MMP-14, MMP-2 and/or MMP-9 is fused to a molecule that is readily detectable either by its presence or activity, including, but not limited to, luciferase, fluorescent protein (e.g., green fluorescent protein), chloramphenicol acetyl transferase, β-galactosidase, secreted placental alkaline phosphatase, β-lactamase, human growth hormone, and other secreted enzyme reporters.

Kits

The present invention provides kits for practice of the afore-described methods. In certain embodiments, kits may comprise antibodies against MMP-14, MMP-2 and/or MMP-9. In other embodiments, a kit may comprise appropriate reagents for determining the level of protein activity in the cells of a subject. In certain embodiments, the cell of a subject may be taken from a tumor biopsy.

In still other embodiments, a kit may comprise a microarray comprising probes of MMP-14, MMP-2 and/or MMP-9 genes or proteins. A kit may comprise one or more probes or primers for detecting the expression level of MMP-14, MMP-2 and/or MMP-9 and/or a solid support on which probes are attached and which may be used for detecting expression. A kit may further comprise controls, buffers, and instructions for use.

Kits may also comprise a library of MMP-14, MMP-2 and/or MMP-9 expression or activity levels associated with survival, response to therapy, stage of disease, etc., e.g., reference sets. In one embodiment, the kit comprises a computer readable medium on which is stored one or more measures of gene expression and/or protein activity associated with survival, response to therapy, stage of disease, etc., or at least values representing such measures of gene expression or protein activity associated with survival, response to therapy, stage of disease, etc. The kit may comprise ratio analysis software capable of being loaded into the memory of a computer system.

Kit components may be packaged for either manual or partially or wholly automated practice of the foregoing methods. In other embodiments involving kits, this invention contemplates a kit including compositions of the present invention, and optionally instructions for their use. Such kits may have a variety of uses, including, for example, imaging, diagnosis, therapy, and other applications.

EXEMPLIFICATION

The present invention is further illustrated by the following examples which should not be construed as limiting in any way.

Example 1

Expression of MMPS in Various Cancer Cell Lines and Correlation to MMP-14 Inhibitor Efficacy FIG. 1 illustrates the relative expression levels of various MMPs, including MMP-14 and MMP-2, in different cancer cell lines. MDA-MB-231 expresses both MMP-14 and MMP-2 in over 50% of cells. MDA-MB-435, BT-474 and PC-3 express only MMP-14 in over 50% of cells. BxPC-3 and B16-F1 express MMP-14 in between 20% and 50% of cells (but not MMP-2). The MCF-7 passage of cells used for these experiments express MMP-14 in between 20% and 50% of cells (but not MMP-2).

The effect of DX-2400, an MMP-14 inhibitor, in inhibiting tumor growth, was strongest in MDA-MB-231, MDA-MB-435, BT-474 and PC-3, all of which express MMP-14 in over 50% of cells (FIGS. 2 and 3). Further, DX-2400 had an effect on metastasis on certain cell lines expressing MMP-14 in at least 20% of cells (FIG. 4).

Example 2

Tumor Growth Data with MMP-14-Positive and MMP-14-Negative Cancer Cells

FIG. 5A shows MMP-14 expression in MDA-MB-231, HUVEC, HT-1080 and MCF-7 cells using a commercial anti-MMP-14 antibody (rabbit polyclonal antibody to MMP-14, Abcam, Cambridge, Mass.). These data show that the MCF-7 cells used for these experiments are negative for MMP-14, in contrast to MDA-MB-231.

FIGS. 5B and 5C show activity of DX-2400 in MDA-MB-231 and MCF-7 tumor xenograft models. As shown in FIG. 5B, DX-2400 inhibited tumor growth of MDA-MB-231 cells. The results seen with some treatments were statistically significant (see, e.g., DX-2400 10 mg/kg, Q2D). Consistent with the lack of MMP-14 expression in the MCF7 cells used for these experiments, DX-2400 (10 mg/kg, ip, qod) did not inhibit MCF-7 tumor growth after two weeks of treatment (FIG. 5C). In these MCF-7 cells, DX-2400 exhibited minimal tumor growth delay (37%) compared to Tamoxifen (83%) after 40 days of treatment. The slight response observed with DX-2400 may be attributed to stromal cells (MMP-14 positive) present in the tumor.

Western blot analysis. To perform the Western blot experiments, whole cell protein extracts were prepared from cells using RIPA buffer. Equal amount of proteins (30 µg) was resolved by 4-12% SDS-PAGE and electroblotted to a PVDF membrane. The blot was probed with a rabbit polyclonal antibody to MMP-14 (Abcam, Cambridge, Mass.) followed by an HRP-conjugated goat anti-rabbit antibody (Thermo Fisher Scientific). Proteins were detected using a Super Signal West Femto Maximum Sensitivity Substrate (Thermo Fisher Scientific). The blot was subsequently stripped and reprobed with a mouse monoclonal antibody to β-actin (Abcam) followed by an HRP-conjugated goat anti-mouse antibody (Thermo Fisher Scientific).

Example 3

Exemplary MMP-14 Binding Antibodies

An exemplary MMP-14 antibody is M0038-F01. The variable domain sequences for M0038-F01 are:

```
VH
                                                              (SEQ ID NO: 13)
38F01 IgG FR1--------------------------- CDR1- FR2----------- CDR2-------
          EVQLLESGGGLVQPGGSLRLSCAASGFTFS LYSMN WVRQAPGKGLEWVS SIYSSGGSTLY

38F01 IgG CDR2-- FR3---------------------------- CDR3-- FR4---------
          ADSVKG RFTISRDNSKNTLYLQMNSLRAEDTAVYYCAR GRAFDI WGQGTMVTVSS

CDR regions are in bold.

VL
                                                              (SEQ ID NO: 14)
38F01 IgG FR1-------------------- CDR1------- FR2------------- CDR2---
          DIQMTQSPSSLSAFVGDKVTITC RASQSVGTYLN WYQQKAGKAPELLIY ATSNLRS GVPS

38F01 IgG FR3------------------------ CDR3------ FR4-------
          RFSGSGSGTDFTLTINTLQPEDFATYYC QQSYSIPRFT FGPGTKVDIK

CDR regions are in bold.
```

Another exemplary MMP-14 antibody is DX-2400. The variable domain sequences for DX-2400 are:

```
VH:
                                                              (SEQ ID NO: 15)
DX-2400  FR1--------------------------- CDR1- FR2----------- CDR2-------
         EVQLLESGGGLVQPGGSLRLSCAASGFTFS LYSMN WVRQAPGKGLEWVS SIYSSGGSTLY

DX-2400  CDR2-- FR3---------------------------- CDR3-- FR4---------
         ADSVKG RFTISRDNSKNTLYLQMNSLRAEDTAVYYCAR GRAFDI WGQGTMVTVSS

CDR regions are in bold.

VL:
                                                              (SEQ ID NO: 16)
DX-2400  FR1-------------------- CDR1------- FR2------------- CDR2---
         DIQMTQSPSSLSASVGDRVTITC RASQSVGTYLN WYQQKPGKAPKLLIY ATSNLRS GVPS
```

```
DX-2400 FR3------------------------ CDR3------ FR4-------
        RFSGSGSGTDFTLTISSLQPEDFATYYC QQSYSIPRFT FGPGTKVDIK
```

CDR regions are in bold.

Another exemplary MMP-14 antibody is M0033-H07. The variable domain sequences for M0033-H07 are:

VH:
(SEQ ID NO: 17)
```
33H07 IgG FR1--------------------------- CDR1- FR2----------- CDR2-------
          EVQLLESGGGLVQPGGSLRLSCAASGFTFS VYGMV WVRQAPGKGLEWVS VISSSGGSTWY

33H07 IgG CDR2-- FR3----------------------------- CDR3------- FR4--------
          ADSVKG RFTISRDNSKNTLYLQMNSLRAEDTALYYCAR PFSRRYGVFDY WGQGTLVTVSS
```

CDR regions are in bold.

VL:
(SEQ ID NO: 18)
```
33H07 IgG FR1-------------------- CDR1------- FR2------------ CDR2---
          DIQMTQSPSSLSASVGDRVTITC RASQGIRNFLA WYQQKPGKVPKLLVF GASALQS

33H07 IgG FR3---------------------------- CDR3----- FR4-------
          GVPSRFSGSGSGTDFTLTISGLQPEDVATYYC QKYNGVPLT FGGGTKVEIK
```

CDR regions are in bold.

Another exemplary MMP-14 antibody is DX-2410. The variable domain sequences for DX-2410 are:

VH:
(SEQ ID NO: 19)
```
DX2410 FR1--------------------------- CDR1- FR2----------- CDR2-------
       EVQLLESGGGLVQPGGSLRLSCAASGFTFS VYGMV WVRQAPGKGLEWVS VISSSGGSTWY

DX2410 CDR2-- FR3----------------------------- CDR3------- FR4--------
       ADSVKG RFTISRDNSKNTLYLQMNSLRAEDTAVYYCAR PFSRRYGVFDY WGQGTLVTVSS
```

CDR regions are in bold.

VL:
(SEQ ID NO: 20)
```
DX2410 FR1-------------------- CDR1------- FR2------------ CDR2---
       DIQMTQSPSSLSASVGDRVTITC RASQGIRNFLA WYQQKPGKVPKLLIY GASALQS

DX2410 FR3---------------------------- CDR3----- FR4-------
       GVPSRFSGSGSGTDFTLTISSLQPEDVATYYC QKYNGVPLT FGGGTKVEIK
```

CDR regions are in bold.

Example 3

Exemplary MMP-9 Binding Antibodies

An exemplary MMP-9 antibody is 539A-M0166-F10. The amino acid sequences of variable regions of 539A-M0166-F10 sFAB are as follows:

```
539A-M0166-F10 (phage/SFAB) VL leader + VL
                                               (SEQ ID NO: 21)
FYSHSAQSELTQPPSASAAPGQRVTILSCSGSSSNIGSNTVTWYQKLPGT

APKLLIYNNYERPSGVPARFSGSKSGTSASLAISGLQSEDEADYYCATWD

DSLIANYVFGSGTKVTVLGQPKANP

539A-M0166-F10 (phage/SFAB) VH leader + VH
                                               (SEQ ID NO: 22)
MKKLLFAIPLVVPFVAQPAMAEVQLLESGGGLVQPGGSLRLSCAASGFTF

SPYLMNWVRQAPGKGLEWVSSIYSSGGGTGYADSVKGRFTISRDNSKNTL

YLQMNSLRAEDTAVYYCARIYHSSSGPFYGMDVWGQGTTVTVSSASTKGP

SVFPLAPSSKS
```

Another exemplary MMP-9 antibody is 539A-M0240-B03. 539A-M0240-B03 is a selective inhibitor of MMP-9. 539A-M0240-B03 can decrease or inhibit the activity of human and mouse MMP-9. The sequences of the complementarity determining regions (CDRs) of 539A-M0240-B03 light chain (LC) and heavy chain (HC) are as follows:

```
LC CDR1: TGTSSDVGGYNYVS    (SEQ ID NO: 23)

LC CDR2: DVSKRPS            (SEQ ID NO: 24)

LC CDR3: CSYAGSYTLV         (SEQ ID NO: 25)

HC CDR1: TYQMV              (SEQ ID NO: 26)
```

```
HC CDR2: VIYPSGGPTVY         (SEQ ID NO: 27)
         ADSVKG

HC CDR3: GEDYYDSSGPGAFDI     (SEQ ID NO: 28)
```

A protein containing the HC CDR sequences of 539A-M0240-B03 and the light chain sequence shown below can be used in the methods described herein. A protein containing the LC CDRs shown below and the HC CDRs of 539A-M0240-B03, or a protein containing the LC variable region (light V gene) shown below and the 539A-M0240-B03 HC CDRs can also be used in the methods described herein. The protein can include a constant region sequence, such as the constant region (LC-lambda1) shown below.

```
Light V gene = VL2_2e; J gene = JL3
                                                              (SEQ ID NO: 29)
      FR1-L                     CDR1-L               FR2-L              CDR2-L
QSALTQPRSVSGSPGQSVTISC  TGTSSDVGGYNYVS  WYQQHPGKAPKLMIY  DVSKRPS FR3-L                          CDR3-L      FR4-L
GVPD RFSGSKSGNTASLTISGLQAEDEADYYC  CSYAGSYTLV  FGGGTKLTVL

-------------------

LC-lambda1
                                                              (SEQ ID NO: 30)
GQPKAAPSVTLFPPSSEELQANKATLVCLISDFYPGAVTVAWKADSSPVKAGVETTTPSKQ

SNNKYAASSYLSLTPEQWKSHRSYSCQVTHEGSTVEKTVAPTECS

CDR regions are in bold.
```

The amino acid and nucleic acid sequences for another exemplary protein that can be used in the methods described herein are provided below. A protein containing the LC and HC CDRs shown below, or a protein containing the light chain and heavy chain variable regions (LV and HV, respectively) shown below can also be used in the methods described herein.

```
Light Chain
Light V gene = VL2_2e 2e.2.2/V1-3/DPL12
Light J gene = JL3

FR1-L                  CFR1-L             FR2-L         CDR2-L
Antibody A: QYELTQPRSVSGSPGQSVTISC  TGTSSDVGGYNYVS  WYQQHPGKAPKLMIY  DVSKRPS  GVPD FR3-L                         CFR1-L      FR2-L
Antibody A: RFSGSKSBNTASLTISGLQAEDEADYYC  CSYAGSYTLV  FGGGTKLTVL  (SEQ ID NO: 31)

Heavy Chain
Heavy V gene: VH3_3-23 DP-47/V3-23
Heavy J gene: JH3

FR1-H                       CDR-H      FR2-H              CDR2-H
Antibody A: EVQLLESGGGLVQPGGSLRLSCAASGFTFS  TYQMV  WVRQAPGKGLEWVS  VIYPSGGPTVYADSVKG FR3-H                           CDR3-H           FR4-H
Antibody A:   RFTISRDNSKNTLYLQMNSLRAEDTAVYYCAR  GEDYYDSSCPCAFDI  WGQGTMVTVSS  (SEQ ID NO: 32)

Light Variable
Antibody A-Light:  Parental clone (sFab; IgG in pBh1 (f)) light variable Q   Y   E   L   T   Q   P   R   S   V   S   G   S   P   G   Q   S   V   T   I
Antibody A:  CAGTACGAATTGACTCAGCCTCGCTCAGTGTCCGGGTCTCCTGGACAGTCAGTCACCATC S   C   T   G   T   S   S   D   V   G   G   Y   N   Y   V   S   W   Y   Q   Q
Antibody A:  TCCTGCACTGGAACCAGCAGTGATGTTGGTGGTTATAACTATGTCTCCTGGTACCAACAG H   P   G   K   A   P   K   L   M   I   Y   D   V   S   K   R   P   S   G   V
Antibody A:  CACCCAGGCAAAGCCCCCAAACTCATGATTTATGATGTCAGTAAGCGGCCCTCAGGGGTC P   D   R   F   S   G   S   K   S   G   N   T   A   S   L   T   I   S   G   L
Antibody A:  CCTGATCGCTTCTCTGGCTCCAAGTCTGGCAACACGGCCTCCCTGACCATCTCTGGGCTC
```

```
                Q  A  E  D  E  A  D  Y  Y  C  C  S  Y  A  G  S  Y  T  L  V
Antibody A:     CAGGCTGAGGATGAGGCTGATTATTACTGCTGCTCATATGCAGGCAGCTAGACTTTGGTG F  G  G  G  T  K  L  T  V  L  (SEQ ID NO: 33)
Antibody A:     TTCGGCGGAGGGACCAAGCTGACCGTCCTA (SEQ ID NO: 34)

Heavy Variable
Antibody A-Heavy:  Parental clone (sFab; IgG in pBh1 (f)) Heavy variable E  V  Q  L  L  E  S  G  G  G  L  V  Q  P  G  G  S  L  R  L
Antibody A:     GAAGTTCAATTGTTAGAGTCTGGTGGCGGTCTTGTTCAGCCTGGTGGTTCTTTACGTCTT S  C  A  A  S  G  F  T  F  S  T  Y  Q  M  V  W  V  R  Q  A
Antibody A:     TCTTGCGCTGCTTCCGGATTCACTTTCTCTACTTACCAGATGGTTTGGGTTCGCCAAGCT P  G  K  G  L  E  W  V  S  V  I  Y  P  S  G  G  P  T  V  Y
Antibody A:     CCTGGTAAAGGTTTGGAGTGGGTTTCTGTTATCTATCCTTCTGGTGGCCCTACTGTTTAT A  D  S  V  K  G  R  F  T  I  S  R  D  N  S  K  N  T  L  Y
Antibody A:     GCTGACTCCGTTAAAGGTCGCTTCACTATCTCTAGAGACAACTCTAAGAATACTCTCTAC L  Q  M  N  S  L  R  A  E  D  T  S  V  Y  Y  C  A  R  G  E
Antibody A:     TTGCAGATGAACAGCTTAAGGGCTGAGGACACGGCCGTGTATTACTCTGCGAGAGGGGAG D  Y  Y  D  S  S  G  P  G  A  F  D  I  W  G  Q  G  T  M  V  T  V  S  S  (SEQ ID NO: 35)
Antibody A:     GACTACTATGATAGTAGTGGCCCGGGGGCTTTTGATATCTGGGGCCAAGGGACAATGGTCACCGTCTCAAGC (SEQ ID NO: 36)
```

The amino acid and nucleic acid sequences for another exemplary protein that can be used in the methods described herein are provided below. A protein containing the LC and HC CDRs shown below, or a protein containing the light chain and heavy chain variable regions (LV and HV, respectively) shown below can also be used in the methods described herein. A protein containing the light chain and heavy chain (designated as LV+LC and HV+HC, respectively, below) sequences can also be used.

Light Chain
Light V gene = VL2.2e 2e.2.2/V1-3/DPL12
Light J gene = JL3

```
                FR1-L                       CDR1-L              FR2-L           CDR2-L
Antibody B: QSALTQPRSVSGSPGQSVTISC TGTSSDVGGYNYVS WYQQHPGKAPKLMIY DVSKRPS GVPD
                  FR3-L              CDR3-L      FR4-L
Antibody B: RFSGSKSGNTASLTISGLQAEDEADYYC CSYAGSYTLV FGGGTKLTVL (SEQ ID NO: 37)
```

Heavy Chain
Heavy V gene: VH3.3-23 DP-47/V3-23
Heavy J gene: JH3

```
                    FR1-H                             CDR1-H     FR2-H          CDR2-H
Antibody B: EVQLLESGGGLVQPGGSLRLSCAASGFTFS TYQMV WVRQAPCKGLEWVS VIYPSGGPTVYADSVKG
                     FR3-H                        CDR3-H              FR4-H
Antibody B: RFTISRDNSKNTLYLQMNSLRAEDTAVYYCAR GEDYDSSGPGAFDI WGQGTMVTVSS (SEQ ID NO: 38)
```

Light Variable
Antibody B-Light: Germlined, codon optimized in GS vector

```
Antibody B: CACAGCGCCCTGACCCAGCCCCGCAGCAGCTGTCCGGCAGCCCAGGCCAGAGCGTGACCATC
            Q  S  A  L  T  Q  P  R  S  V  S  G  S  P  G  Q  S  V  T  I
Antibody B: AGCTGCACCGGCACCAGCAGCGACGTGGGCGGCTACAACTACGTGTCCTGGTATCAGCAG
            S  C  T  G  T  S  S  D  V  G  G  Y  N  Y  V  S  W  Y  Q  Q
Antibody B: CACCCCGGCAAGGCCCCCAAGCTGATGATCTACGACGTGTCCAAGAGGCCCAGCGGCGTG
            H  P  G  K  A  P  K  L  M  I  Y  D  V  S  K  R  P  S  G  V
Antibody B: CCCGACAGGTTCAGCGGCAGCAAGAGCGGCAACACCGCCAGCCTGACCATCTCCGGACTG
            P  D  R  F  S  G  S  K  S  G  N  T  A  S  L  T  I  S  G  L
Antibody B: CAGGCCGAGGACGAGGCCGACTACTACTGCTGCAGCTACGCCGGCAGCTACACCCTGGTG
            Q  A  E  D  E  A  D  Y  Y  C  C  S  Y  A  G  S  Y  T  L  V
Antibody B: TTCGGCGGAGGGACCAAGCTGACCGTGCTG  (SEQ ID NO: 39)
            F  G  G  G  T  K  L  T  V  L   (SEQ ID NO: 40)
```

-continued

Heavy Variable
Antibody B-Heavy: Germlined, codon optimized in GS vector

Antibody B: GAGGTGCAATTGCTGGAAAGCGGCGGAGGACTGGTGCAGCCAGGCGGCAGCCTGAGGCTG
             E   V   Q   L   L   E   S   G   G   G   L   V   Q   P   G   G   S   L   R   L Antibody B: TCCTGCGCCGCCAGCGGCTTCACCTTCAGCACTTACCAGATGGTGTGGGTGCGCCAGGCC
             S   C   A   A   S   G   F   T   F   S   T   Y   Q   M   V   W   V   R   Q   A Antibody B: CCAGGCAAGGGCCTGGAATGGGTGTCCGTGATCTACCCCAGCGGCGGACCCACCGTGTAC
             P   G   K   G   L   E   W   V   S   V   I   Y   P   S   G   G   P   T   V   Y Antibody B: GCCGACAGCGTGAAGGGCAGGTTCACCATCAGCAGGGACAACAGCAAGAACACCCTGTAC
             A   D   S   V   K   G   R   F   T   I   S   R   D   N   S   K   N   T   L   Y Antibody B: CTGCAGATGAACAGCCTGAGGGCCGAGGACACCGCCGTGTACTACTGCGCCAGGGGCGAG
             L   Q   M   N   S   L   R   A   E   D   T   A   V   Y   Y   C   A   R   G   E Antibody B: GACTACTACGACAGCAGCGGCCCAGCCTTCGACATCTGGGGCCAGGGCACAATGGTGACCGTGTCCAGC (SEQ ID NO: 41)
             D   Y   Y   D   S   S   G   P   A   F   D   I   W   G   Q   G   T   M   V   T   V   S   S    (SEQ ID NO: 42)

>Antibody B: LV + LC dna
CAGAGCGCCCTGACCCAGCCCCAGAAGCCTGGCCAGCCCAGGCCCAGGAGCGTGTCCGGCAACGTCATCAGCTGCACCGGCACCAGCAGCGACGTGGGCGGCTACAACTACGTGTC
CTGGTATCAGCAGCACCCAGGCAAGGCCCCCAAGCTGATGATCTACGACGTGTCCGTGAATGGTGTCCGTGATCTACCCCAGCGGCGTGCCCGACAGGTTCAGCGGCTCCAGCTCA
CCGCCAGCCTGACCATCTCCGGACTGCAGGCCGAGGACGAGGCCGACTACTACTGTGCCAGCAGCTACTACCGCAGCAGCCTGAGGCTGGTGGTGTTCGGCGGAGGGACCAAGCTG
ACCGTGCTGGGCCAGCCCAAGGCTGCCCCAGCGCTGTTCCCCCCAGCAGCGAGGAACTGCAGGCCAACAAGGCCACACTGGTGTGCCTGATCAGCGACTT
CTACCCAGGGCGCTGTGGCCTGACCGTGGCCTGGAAGGCAGATGGCAGCCCCGTGAAGGCGGCCGTGGAGACCACCACCCCAGCAGGCAGCAACAACAAGTACGCCGCA
GCAGCTACCTGAGCCTGACCCCAGAGCAGGTGACCCACAAGAGCTACTCCCTGCAGGCTCCACAGTCGACCCTGAGCAGCACAAGACCCTCC
TGTCCTGCAGTCCTGCATCCTGAAGCGTGTGACCCACGAAAGCAGCTAG (SEQ ID NO: 43)

>Antibody B: HV + HC dna
GAGGTGCAATTGCTGGAAAGCGGCGGAGGACTGGTGCAGCCAGGCGGCAGCCTGAGGCTGTCCTGCGCCGCCAGCGGCTTCACCTTCAGCACTTACCAGATGGTGTG
GGTGCGCCAGGCCCCAGGCAAGGGCCTGGAATGGGTGTCCGTGATCTACCCCAGCGGCGGACCCACCGTGTACGCCGACAGCGTGAAGGGCAGGTTCACCATCAGCA
GGGACAACAGCAAGAACACCCTGTACCTGCAGATGAACAGCCTGAGGGCCGAGGACACCGCCGTGTACTACTGCGCCAGGGGCGAGGACTACTACGACAGCAGCGGC
CCAGCCTTCGACATCTGGGGCCAGGGCACAATGGTGACCGTGTCCAGCGCCTCCACCAAGGGCCCCAGCGTGTTCCCGCTAGCACCTCTCCAAGTCCACCTC
TGGCGGCACCGCCGCTCTGGGCTGCCTGGTGAAGGACTACTTCCCCGAGCCCGTGACCGTGTCCTGGAACTCTGGCGCCCTGACCTCGGCGTGCATACCTTCCCG
CCGGTCTGCAGTCCTGCAGCCTGTACTCCCTGAGCAGCGTGGTGACCGTGACCTCCAGCAACTTCGGCACCCAGACCTACATCTGCAACGTGAACCACAAGCCTTCC
AACACCAAGGTGGACAAGCGCCGTGGAGCCCAAGAGCTGCGACAAGACCCACACCTGCCCCCCTGCCCGAGCCTGCACCTACCGGTGCCACCTGTGGTCCGACCA
CCCTCCTAAGCCTGCCAGGAGGTCCACAACGCCAAGCCAAGCCAAGCCTGAGCGACGAGGCCACAAAGCCGGCAGGCGCGACAACAAGACCCGCCCTGGAGGCAGCAAAGCCAAGCAAGCC
TGGACGGCGTGGAGGTGCATAATGCCAAAGACCAAGCCAAGCCCGCGTTCAGCCGTTCCCACAACAGCACTTACTCCGTGCTGACCGTGCTGCACCAGGACTGGCTG
AACGGCAAGGAATACAAGTGCAAGGTCTCCAACAAGGCCCTGCCTGCCCCCATCGAGAAAACCATCTCCAAGGCCAAGGGCCAGCCTCGCGAGCCTCAGGTGTACAC
CCTGCCTCCTAGCCGGGAGGAAATGACCAAGAACCAGGTGTCCCTGACCTGCCTGGTCAAGGGCTTCTACCCTTCCGATATCGCCGTGGAGTGGGAGTCCAACGGC
CAGCCTGAGAACAACTACAAGACCACCCCTCCTGTGCTGGACTCCGACGGCTCCTTCTTCCTGTACTCCAAGCTGACCGTGGACAAGTCCCGGTGGCAGCAGGGCAAC
GTGTTCTCCTGCTCCGTGATGCACGAGGCCCTGCACAACCACTACACCCAGAAGTCCCTGTCCCTGAGCCCTGGCAAGTGA (SEQ ID NO: 44)

>Antibody B: LV + LC aa
QSALTQPRSVSGSPGQSVTISCTGTSSDVGGYNYVSWYQQHPGKAPKLMIYDVSKRPSGVPDRFSGSKSGNTASLTISGLQAEDEADYYCCSYAGSYTLVFGGGTKL
TVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTE
CSss (SEQ ID NO: 45)

>Antibody B: HV + HC aa
EVQLLESGGGLVQPGGSLRLSCAASGFTFSTYQMVWVRQAPGKGLEWVSVIYPSGGPTVYADSVKGRFTISRDNSKNTLYLQMNSLRAEDTAVYYCARGEDYDSSG
PGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPS
NTKVDKRVEPKSCDKHTCPPCPAPELLGGPSVFLFPPKPKDTLMISRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGN
VFSCSVMHEALHNHYTQKSLSLSPGKs (SEQ ID NO: 46)

REFERENCES

The contents of all cited references including literature references, issued patents, published or non-published patent applications cited throughout this application are hereby expressly incorporated by reference in their entireties. In case of conflict, the present application, including any definitions herein, will control.

EQUIVALENTS

A number of embodiments of the invention have been described. Nevertheless, it will be understood that various modifications may be made without departing from the spirit and scope of the invention. Accordingly, other embodiments are within the scope of the following claims.

---

The invention claimed is:

1. A method of identifying a subject who may benefit from administration of an MMP-14 binding protein to treat cancer, the method comprising evaluating an expressional ratio of MMP-14 to MMP-9, an expressional ratio of MMP-14 to MMP-2, or an expressional ratio of MMP-2 to MMP-9 in a sample from the subject, and if the expressional ratio of MMP-14 to MMP-9, the expressional ratio of MMP-14 to MMP-2, or the expressional ratio of MMP-2 to MMP-9 is greater than 1, identifying the subject for administration of an MMP-14 binding protein.

2. A method of selecting a therapy for cancer for a subject, the method comprising evaluating an expressional ratio of MMP-14, to MMP-9, an expressional ratio of MMP-14 to MMP-2 or an expressional ratio of MMP-2 to MMP-9 in a sample from the subject, and
   if the expressional ratio of MMP-14 to MMP-9, the expressional ratio of MMP-14 to MMP-2, or the expressional ratio of MMP-2 to MMP-9 is greater than 1, selecting an MMP-14 binding protein as the cancer therapy.

3. The method of any one of claim 1 or 2, wherein the cancer is selected from the group consisting of: osteotropic cancer, breast cancer, lung cancer, colon cancer and prostate cancer.

4. The method of claim 3, wherein the sample is a tumor biopsy.

5. The method of claim 1 or 2, wherein the expressional ratio is the ratio of MMP-14 to MMP-9 expression or the ratio of MMP-14 to MMP-9 protein activity.

6. The method of claim 1 or 2, wherein the expressional ratio is the ratio of MMP-14 to MMP-2 expression or the ratio of MMP-14 to MMP-2 protein activity.

7. The method of claim 1 or 2, wherein the expression ratio is the ratio of MMP-2 to MMP-9 expression or the ratio of MMP-2 to MMP-9 protein activity.

8. The method of claim 1 or 2, wherein the MMP-14 binding protein is an antibody or antibody fragment.

9. The method of claim 8, wherein the antibody fragment is a single chain antibody, a Fab fragment, an sFab fragment, a F(ab')$_2$ fragment, an Fd fragment, an Fv fragment, an scFv fragment, or a domain antibody (dAb) fragment.

10. The method of claim 8, wherein the antibody or antibody fragment competes for binding with DX-2400.

11. The method of claim 5 or 6, wherein the expression is protein expression.

12. The method of claim 11, wherein the level of protein expression is determined using an MMP-14, MMP-9 and/or MMP-2 antibody.

13. The method of claim 8, wherein the antibody or antibody fragment is a human antibody, an effectively human antibody or a humanized antibody.

14. The method of claim 1 or 2, wherein the cancer is melanoma.

15. The method of claim 1 or 2, wherein the cancer is a diffuse large B-cell lymphoma.

16. The method of claim 1 or 2, wherein the MMP-14 binding protein comprises heavy chain CDR1, CDR2 and CDR3 of SEQ ID NO: 13 and light chain CDR1, CDR2 and CDR3 of SEQ ID NO:14.

17. The method of claim 16, wherein the MMP-14 binding protein is DX-2400.

18. The method of claim 16, wherein the MMP-14 binding protein is M0038-F01.

19. The method of claim 1 or 2, wherein the MMP-14 binding protein is DX-2410.

* * * * *